(12) United States Patent
Hung et al.

(10) Patent No.: US 9,822,140 B2
(45) Date of Patent: Nov. 21, 2017

(54) METHODS AND INTERMEDIATES FOR THE PREPARATION OF FONDAPARINUX

(71) Applicant: Academia Sinica, Taipei (TW)

(72) Inventors: Shang-Cheng Hung, Taipei (TW); Cheng-Hsiu Chang, Changhua (TW)

(73) Assignee: Academia Sinica, Taipei (TW)

( * ) Notice: Subject to any disclaimer, the term of this patent is extended or adjusted under 35 U.S.C. 154(b) by 144 days.

(21) Appl. No.: 14/406,074

(22) PCT Filed: Jun. 3, 2013

(86) PCT No.: PCT/US2013/043866
§ 371 (c)(1),
(2) Date: Dec. 5, 2014

(87) PCT Pub. No.: WO2013/184564
PCT Pub. Date: Dec. 12, 2013

(65) Prior Publication Data
US 2015/0126721 A1    May 7, 2015
US 2015/0344513 A9    Dec. 3, 2015

Related U.S. Application Data

(60) Provisional application No. 61/655,852, filed on Jun. 5, 2012.

(51) Int. Cl.
| | |
|---|---|
| *C07H 1/00* | (2006.01) |
| *C07H 15/04* | (2006.01) |
| *C07H 23/00* | (2006.01) |
| *C07H 3/06* | (2006.01) |
| *C07H 15/18* | (2006.01) |
| *C07H 15/203* | (2006.01) |

(52) U.S. Cl.
CPC ............... *C07H 15/04* (2013.01); *C07H 1/00* (2013.01); *C07H 3/06* (2013.01); *C07H 15/18* (2013.01); *C07H 15/203* (2013.01); *C07H 23/00* (2013.01)

(58) Field of Classification Search
CPC ........ C08B 37/0078; C07H 5/04; C07H 5/06; C07H 7/033; C07H 15/04; C07H 23/00
See application file for complete search history.

(56) References Cited

U.S. PATENT DOCUMENTS

| | | |
|---|---|---|
| 2008/0171722 A1 | 7/2008 | Hung et al. |
| 2009/0187013 A1 | 7/2009 | Seifert et al. |
| 2011/0105418 A1 | 5/2011 | Nadji et al. |
| 2012/0116066 A1 | 5/2012 | Patel et al. |
| 2014/0051659 A1* | 2/2014 | Schwoerer ........... A61K 31/737 514/54 |

OTHER PUBLICATIONS

Arungundram et al., Modular Synthesis of Heparan Sulfate Oligosaccharides for Structure-Activity Relationship Studies, Journal of the American Chemical Society, Nov. 11, 2009, vol. 131, No. 47, pp. 17394-17405.
PCT/US2013/043866, Sep. 11, 2013, International Search Report and Written Opinion.
PCT/US2013/043866, Dec. 18, 2014, International Preliminary Report on Patentability.

* cited by examiner

*Primary Examiner* — Leigh C Maier
(74) *Attorney, Agent, or Firm* — Wolf, Greenfield & Sacks, P.C.

(57) ABSTRACT

The present invention relates to methods for the synthesis of fondaparinux and intermediates thereto.

65 Claims, 14 Drawing Sheets

Figure 2    Synthesis of D-Glucosamine Derivatives
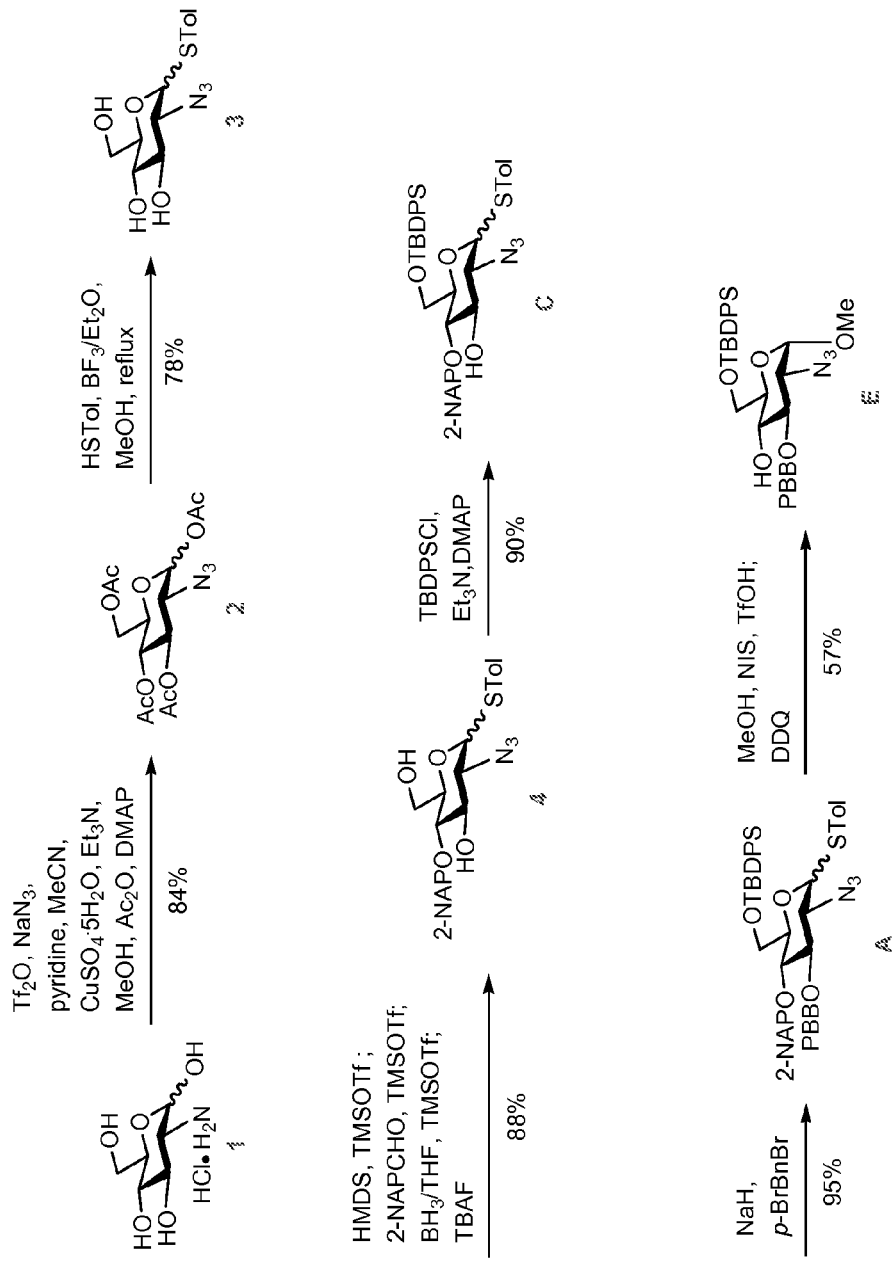

Figure 3    Synthesis of D-Glucose Derivatives
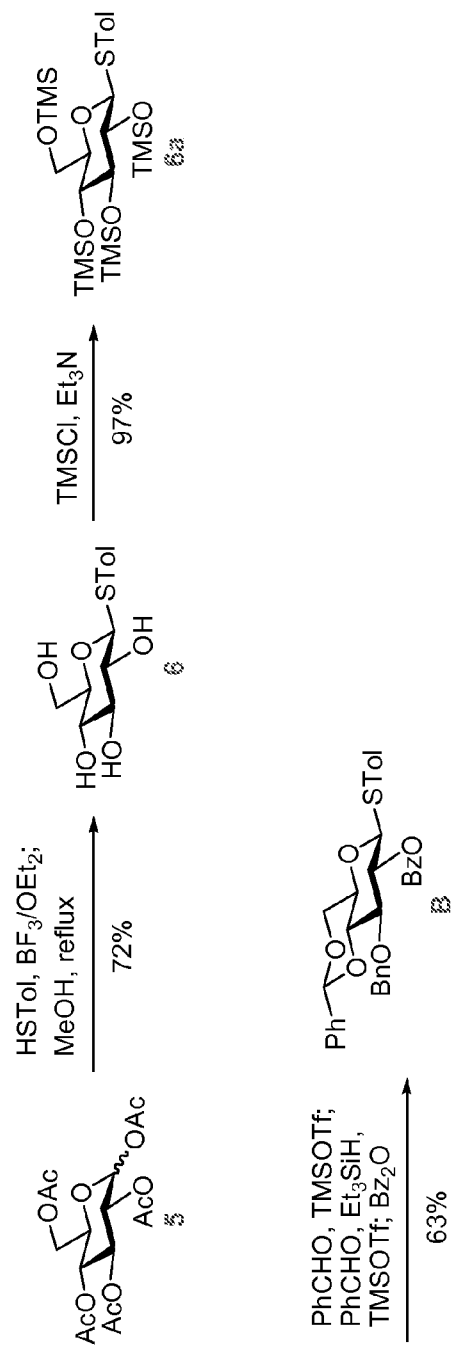

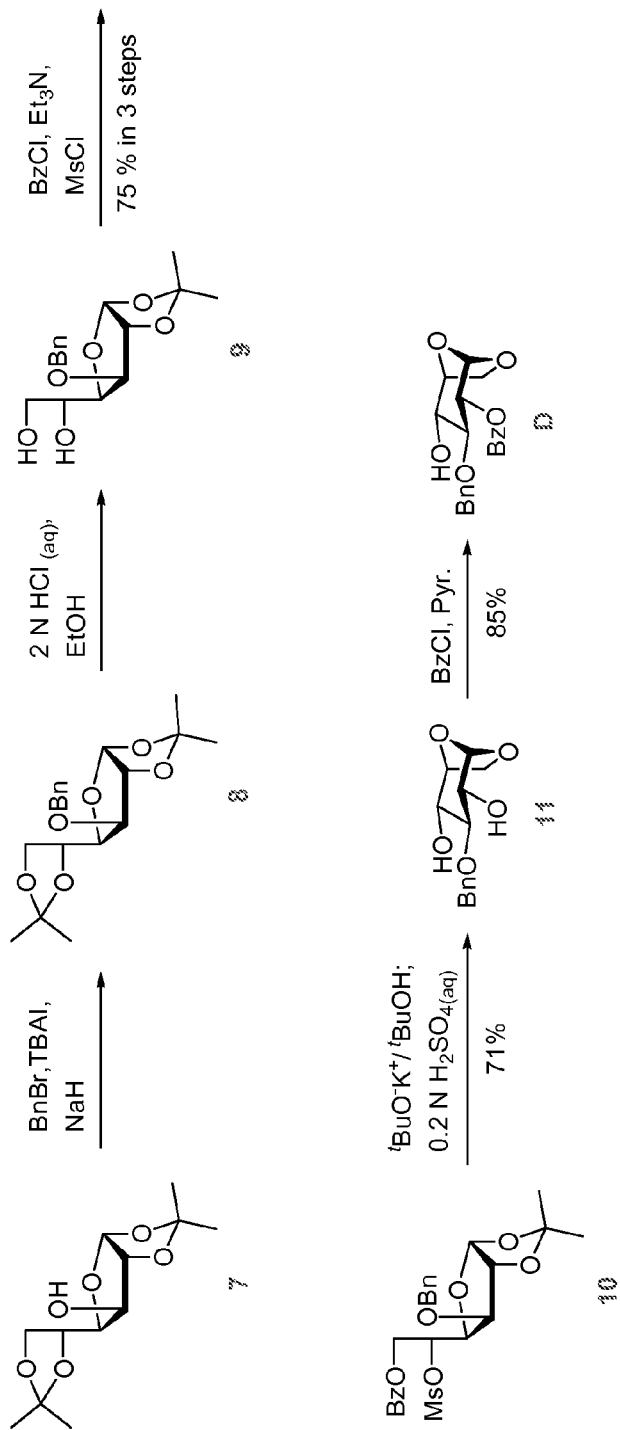
Figure 4  Synthesis of the 1,6-Anhydro-β-L-idopyranosyl Sugar

Figure 5 Synthesis of the Disaccharide Acceptor (CD)
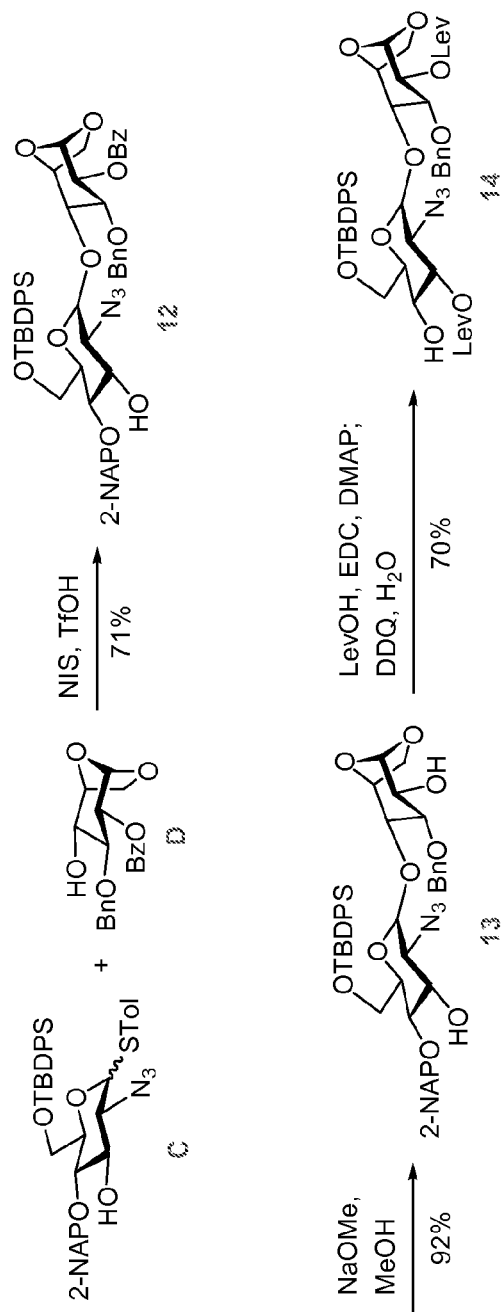

Figure 6 Preparation of the Trisaccharide Acceptor (BCD)
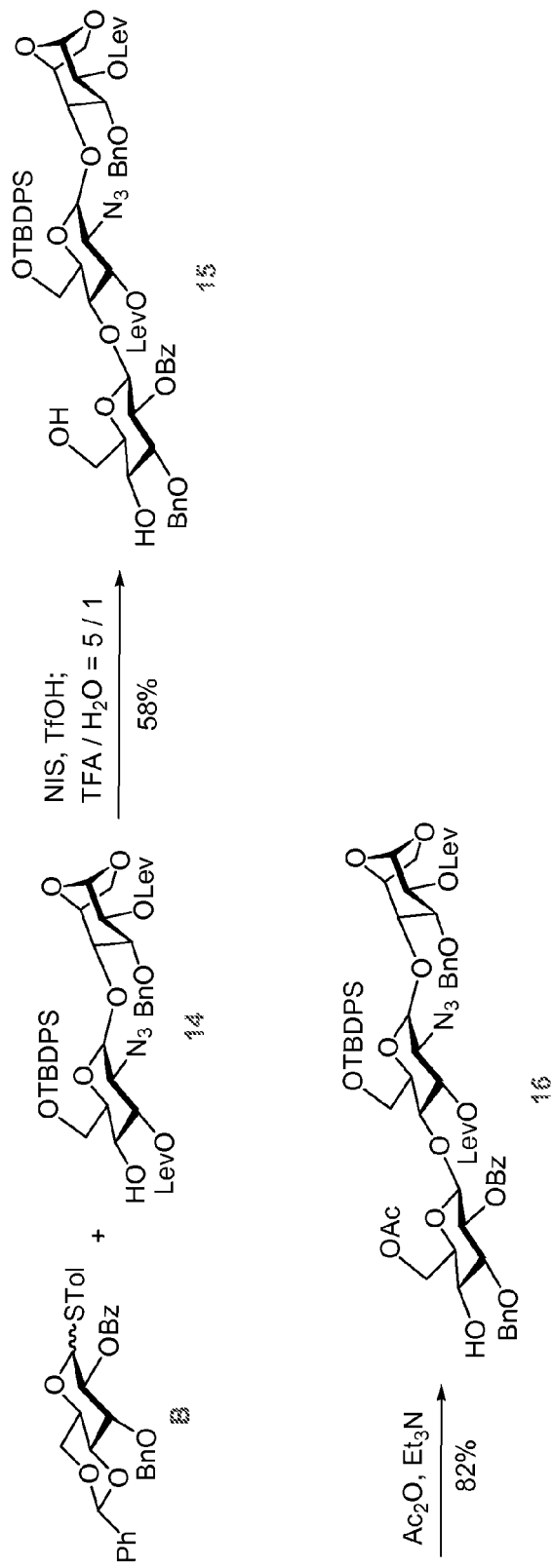

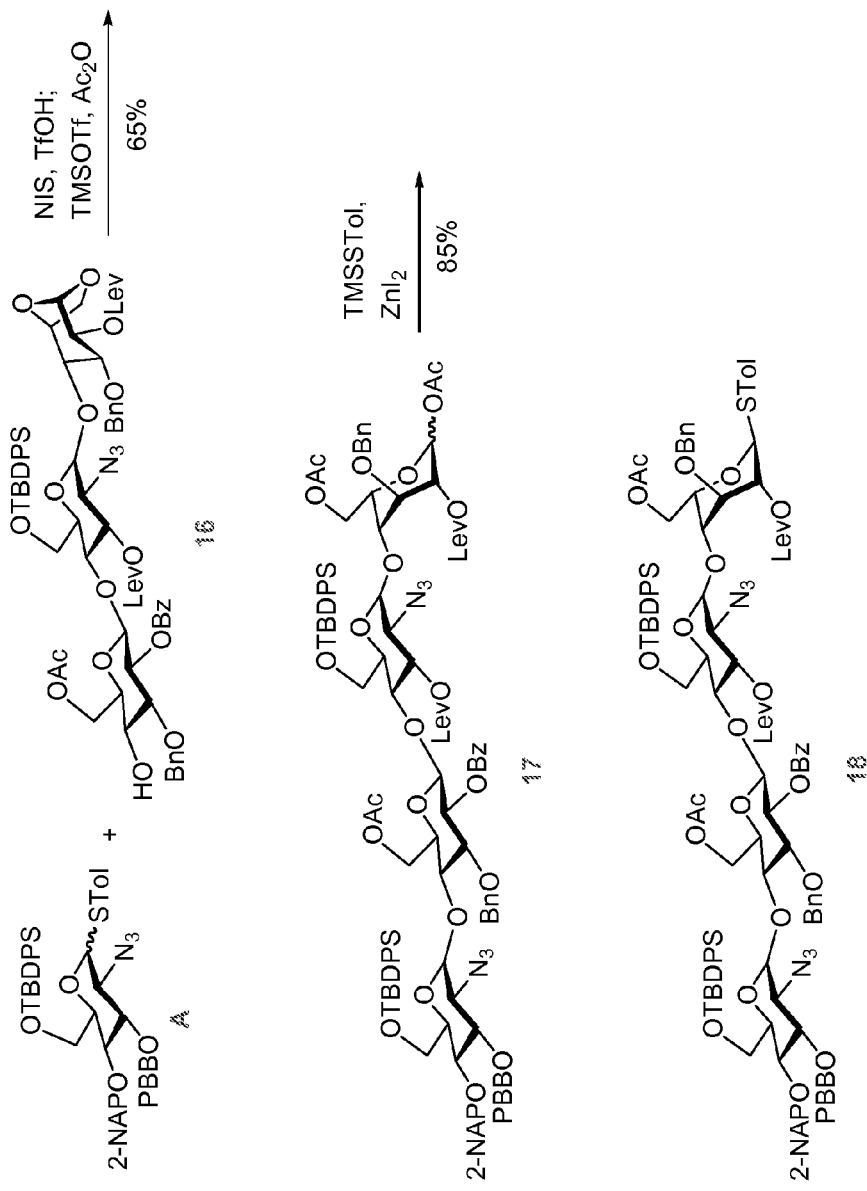
Figure 7  Preparation of the Tetrasaccharide Donor (ABCD)

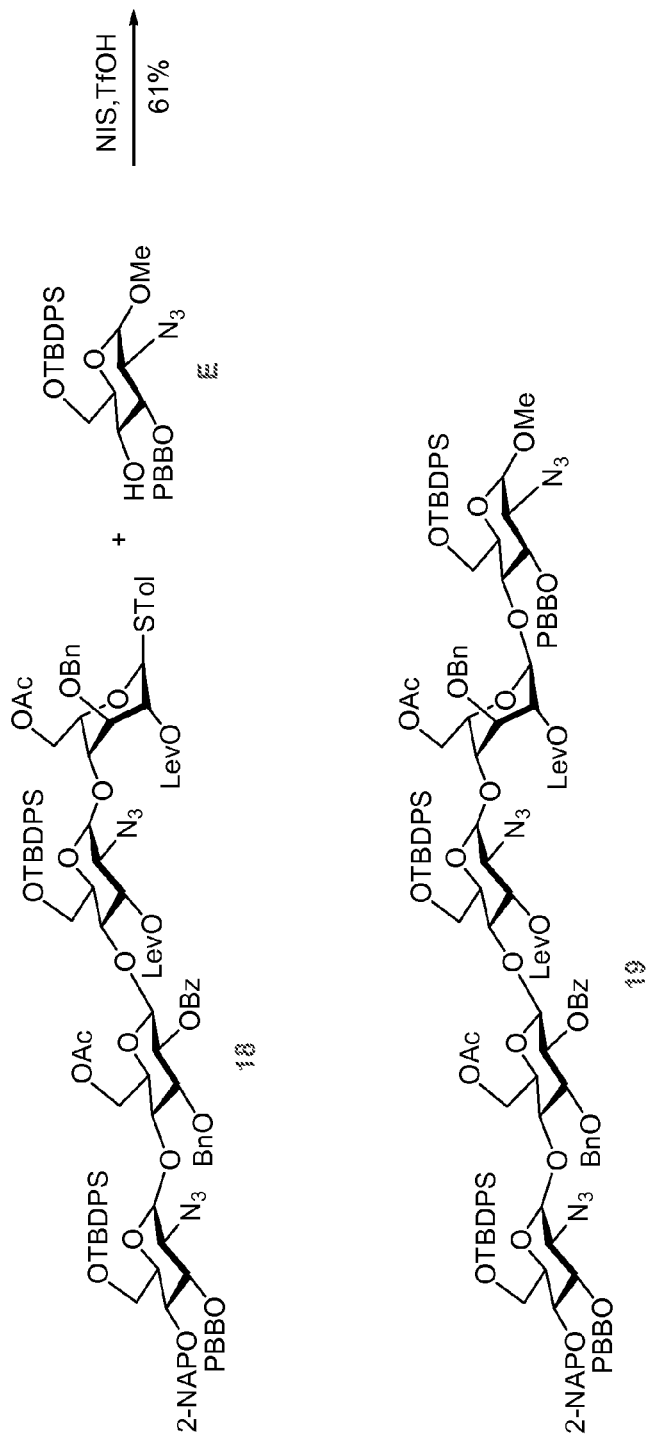
Figure 8 Synthesis of the Pentasaccharide Skeleton (ABCDE)

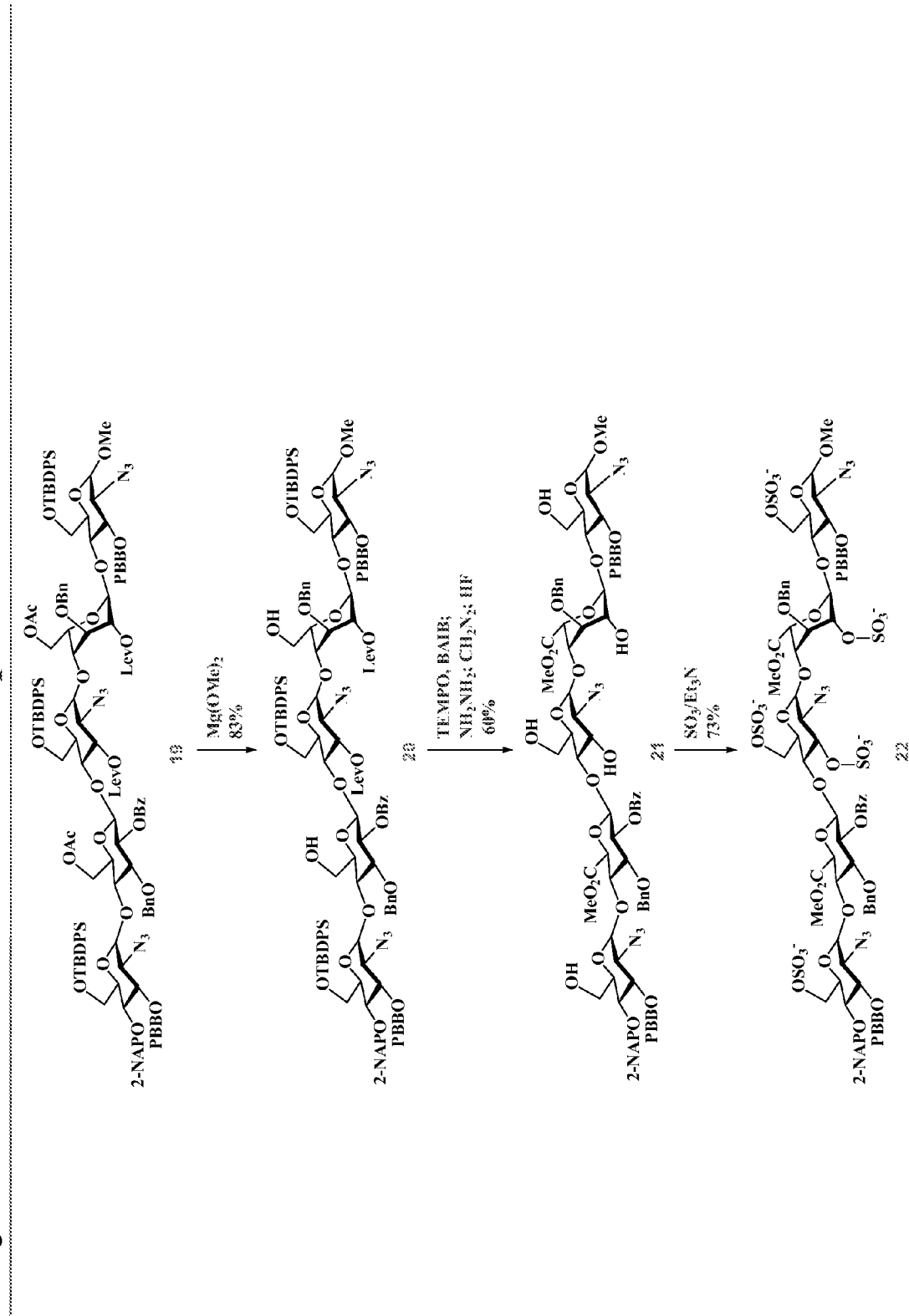
Figure 9A  Functional Group Transformation

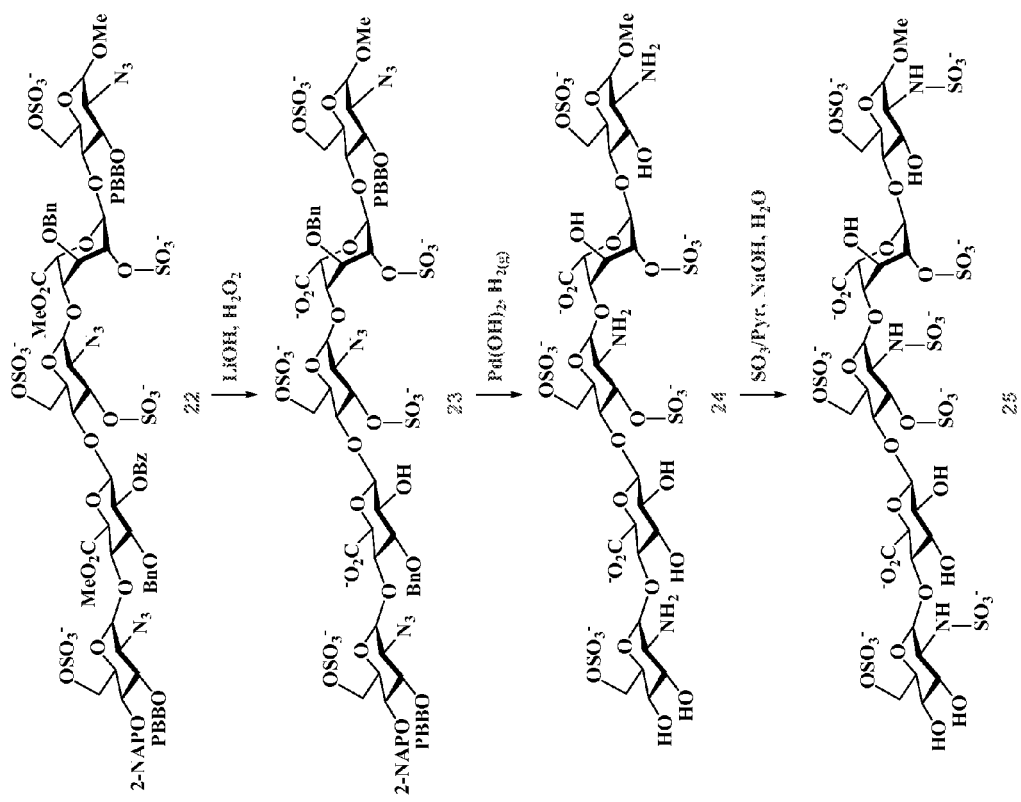
Figure 9B  Functional Group Transformation

Conclusions

Figure 12  Synthesis of the Disaccharide Donor (AB)
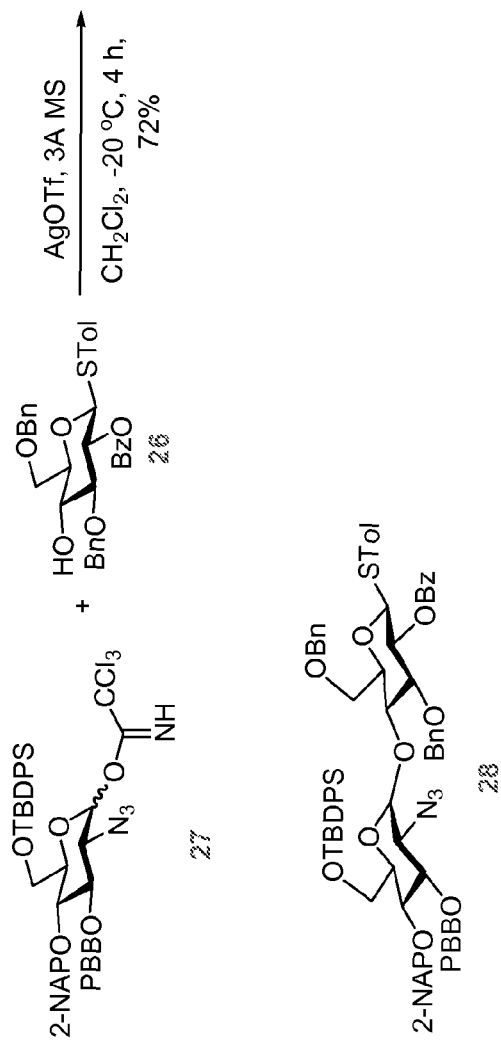

Figure 13 Preparation of the Tetrasaccharide Donor (ABCD)
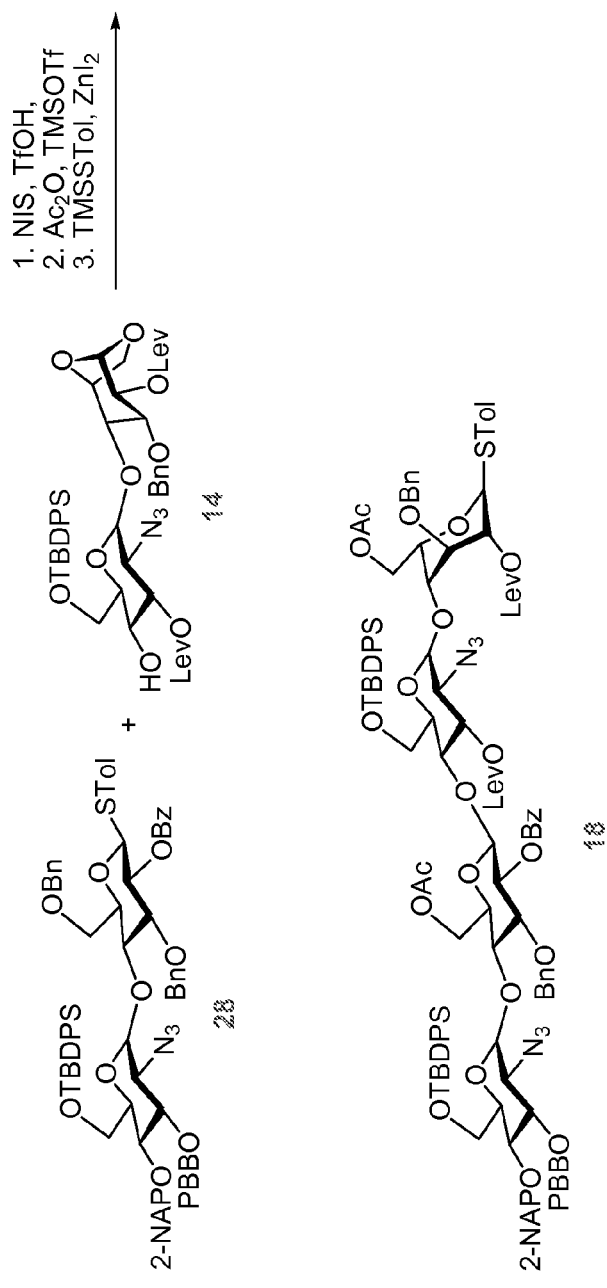

METHODS AND INTERMEDIATES FOR THE PREPARATION OF FONDAPARINUX

RELATED APPLICATION

This application is a national stage filing under 35 U.S.C. §371 of international PCT application PCT/US2013/043866, filed Jun. 3, 2013, which claims priority to U.S. Provisional Patent Application No. 61/655,852, filed Jun. 5, 2012, the contents of each of these applications are hereby incorporated by reference in their entireties.

BACKGROUND OF THE INVENTION

Fondaparinux (Arixtra®) is a synthetic, highly sulfated pentasaccharide, which has a sequence derived from the minimal antithrombin (AT) binding region of heparin. Fondaparinux is the first in a class of antithrombotic agents known as the selective factor Xa inhibitors (*Cardiovasc. Drug Rev.* 2002, 20(1):37-52). The clinical use of fondaparinux as an anticoagulant is known (*Thromb. Res.* 2012, 129(4):407, *Curr. Opin. Pulm. Med.* 2004, 10(5):338). The use of such agents for the prevention and/or treatment of venous thromboembolism has been reported (Walenga et al., *Expert Opin. Investig. Drugs* 2002, 11: 397-407; Bauer, *Best Practice & Research Clinical Hematology* 2004, 17(1): 89-104).

There are several disadvantages of current methods used for the synthesis of fondaparinux sodium. First, published overall yields are low. The synthesis by Sinaÿ's method only provided an overall yield of 0.053% (*Carbohydrate Research*, 1984, 132(2): C5-C9.). Van Boeckel and co-workers provided a method on reasonable scale (156 mg of final product) overall yield of 0.22% (*J. Carbohydrate Chem.* 4(3):293-321). Second, stereoselective formation of the 1,2-cis of the α-D-glucosamine glycosidic bond is challenging. Third, published syntheses of fondaparinux contain over 50 synthetic steps (see, U.S. Pat. No. 7,541,445). Fourth, when glucuronic and iduronic acids are employed as glycosyl acceptors in the synthesis, the glycosylation reaction proceeds in low yield and is accompanied by β-elimination side product.

In summary, there are several limitations to current methods of synthesizing fondaparinux in the art. Thus, there is a need for new synthetic procedures that produce fondaparinux, related compounds, and intermediates thereto in an efficient manner.

SUMMARY OF THE INVENTION

The present invention relates to methods for the synthesis of fondaparinux and intermediates thereto. Methods described herein provide a reliable and scalable synthesis of fondaparinux. The present inventors have applied the strategy of "regioselective one-pot protection" and introduced orthogonal protecting groups. The methods described herein have considerably reduced synthetic effort and require fewer purification steps compared with methods in the art. For example, in certain embodiments, a method described herein allows for synthesis of fondaparinux in 28 steps with highly stereoselective control of all glycosidic bond formations.

In one aspect, the present invention provides a compound of Formula (I):

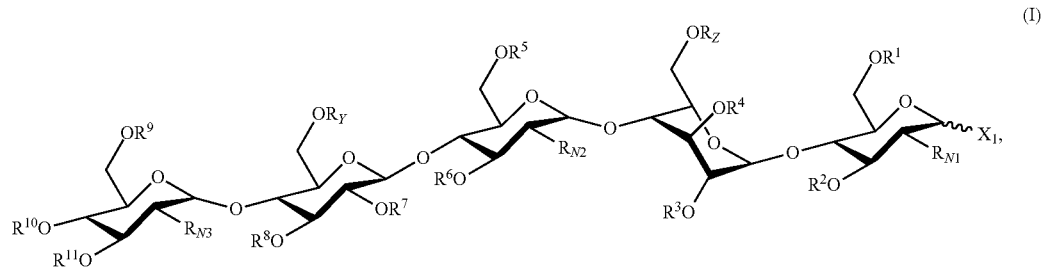

or a salt thereof wherein $X_1$, $R^1$, $R^2$, $R^3$, $R^4$, $R^5$, $R^6$, $R^7$, $R^8$, $R^9$, $R^{10}$, $R^{11}$, $R_Y$, $R_Z$, $R_{N1}$, $R_{N2}$, and $R_{N3}$ are as described herein. In certain embodiments, a compound of Formula (I) is useful in the synthesis of fondaparinux.

In another aspect, the present invention provides a compound of Formula (II):

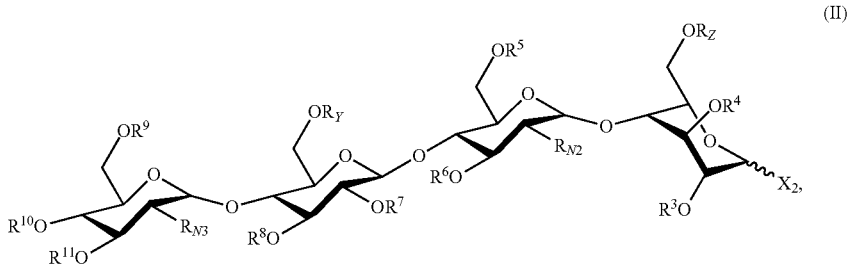

or a salt thereof, wherein $X_1$, $R^3$, $R^4$, $R^5$, $R^6$, $R^7$, $R^8$, $R^9$, $R^{10}$, $R^{11}$, $R_Y$, $R_Z$, $R_{N2}$, and $R_{N3}$ are as described herein. In certain embodiments, a compound of Formula (II) is useful in the synthesis of fondaparinux.

In another aspect, the present invention provides a compound of Formula (III):

(III)

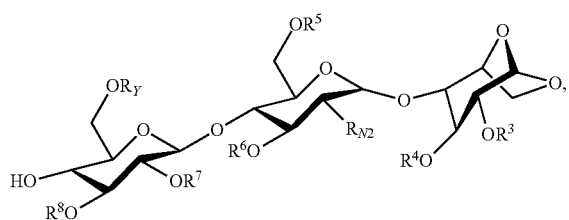

or a salt thereof, wherein $R^3$, $R^4$, $R^5$, $R^6$, $R^7$, $R^8$, $R_Y$, and $R_{N2}$ are as described herein. In certain embodiments, a compound of Formula (III) is useful in the synthesis of fondaparinux.

In another aspect, the present invention provides methods for synthesizing a trisaccharide of formula (III):

(III)

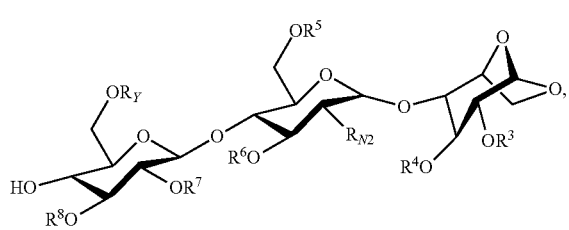

or a salt thereof;

the method comprising:

(a) reacting monosaccharides of formulae C and D;

C

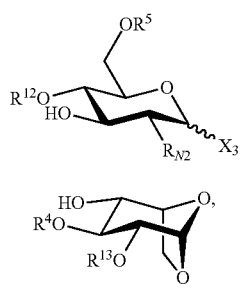

D

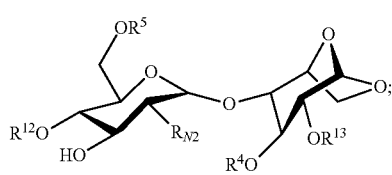

in the presence of an activating agent under suitable conditions to form a disaccharide of formula (IV):

(IV)

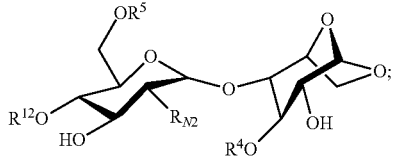

(b) deprotecting the disaccharide of formula (IV) under suitable conditions to form a compound of formula (V):

(V)

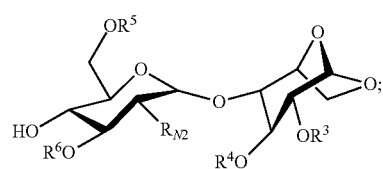

(c) protecting and deprotecting the compound of formula (V) under suitable conditions to form a compound of formula (VI):

(VI)

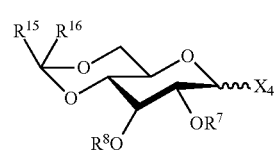

(d) reacting the compound of formula (VI) with a monosaccharide of formula B:

B

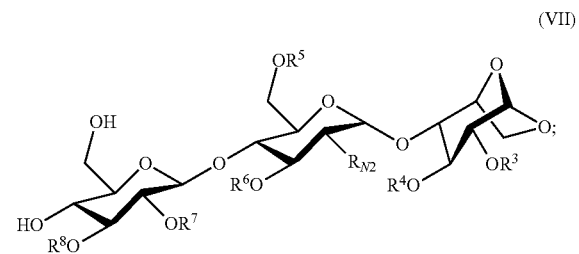

in the presence of an activating agent under suitable conditions to form a trisaccharide of formula (VII):

(VII)

and (e) protecting the trisaccharide of formula (VII) under suitable conditions to form a trisaccharide of formula (III);

wherein $X_3$, $X_4$, $R^3$, $R^4$, $R^5$, $R^6$, $R^7$, $R^8$, $R^{12}$, $R^{13}$, $R^{15}$, $R^{16}$, $R_Y$, and $R_{N2}$ are as described herein.

In another aspect, the present invention provides methods of synthesizing a tetrasaccharide of formula (II):

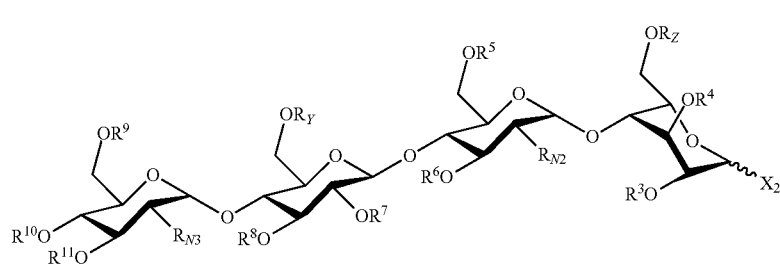
(II)

or a salt thereof;
the method comprising:
(a) reacting a trisaccharide of formula (III):

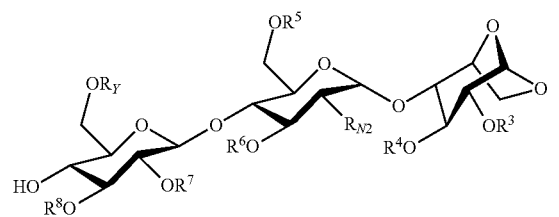
(III)

with a monosaccharide of formula A:

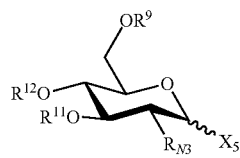
A in the presence of an activating agent under suitable conditions to form a compound of formula (VIIIa):

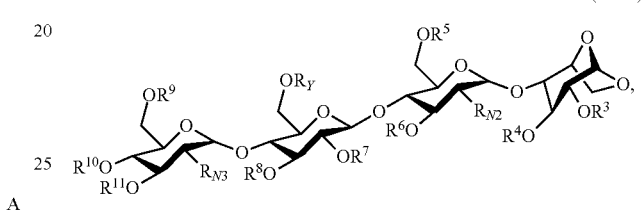
(VIIIa)

(b) ring-opening and protecting the compound of formula (VIIIa) under suitable conditions to form a compound of formula (VIII):

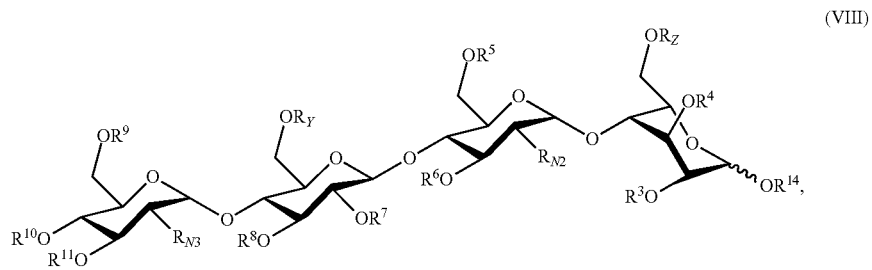
(VIII)

wherein $R^{14}$ is a protecting group; and
(c) converting the —$OR^{14}$ group of the compound of formula (VIII) to a leaving group $X_2$ under suitable conditions to form a compound of formula (II);
wherein $X_2$, $X_5$, $R^3$, $R^4$, $R^5$, $R^6$, $R^7$, $R^8$, $R^9$, $R^{10}$, $R^{11}$, $R^{14}$, $R_Y$, $R_Z$, $R_{N2}$, and $R_{N3}$ are as described herein.

In certain embodiments, the tetrasaccharide of formula (II) is further reacted with monosaccharide E:

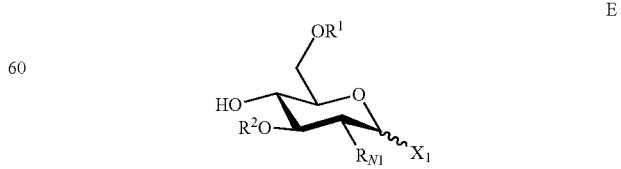
E wherein $X_1$, $R^1$, $R^2$, and $R_{N1}$ are as described herein; under suitable conditions to form a pentasaccharide of formula (I).

In another aspect, the present invention provides methods of synthesizing a tetrasaccharide of Formula (II):

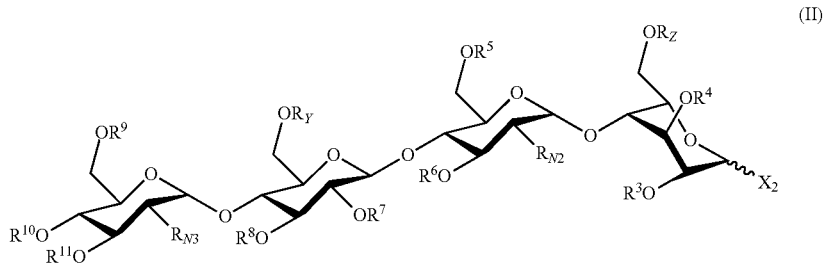

or a salt thereof;
the method comprising:
(a) reacting a disaccharide of formula (VI):

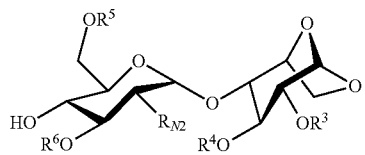

with a disaccharide of formula F:

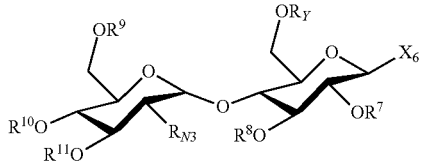

in the presence of an activating agent under suitable conditions to form a compound of formula (VIIIa):

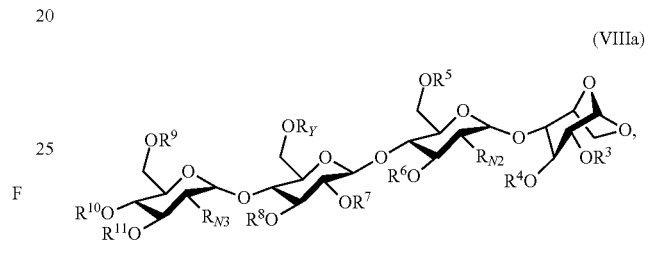

(b) ring-opening and protecting the compound of formula (VIIIa) under suitable conditions to form a compound of formula (VIII):

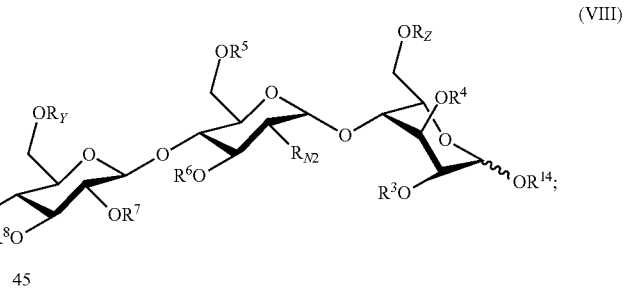

and
(c) converting the —$OR^{14}$ group of the compound of formula (VIII) to a leaving group $X_2$ under suitable conditions to form a compound of formula (II);
wherein $X_2$, $X_6$, $R^3$, $R^4$, $R^5$, $R^6$, $R^7$, $R^8$, $R^9$, $R^{10}$, $R^{11}$, $R^{14}$, $R_Y$, $R_Z$, $R_{N2}$, and $R_{N3}$ are as described herein.

In another aspect, the present disclosure provides methods for synthesizing a pentasaccharide of formula (I):

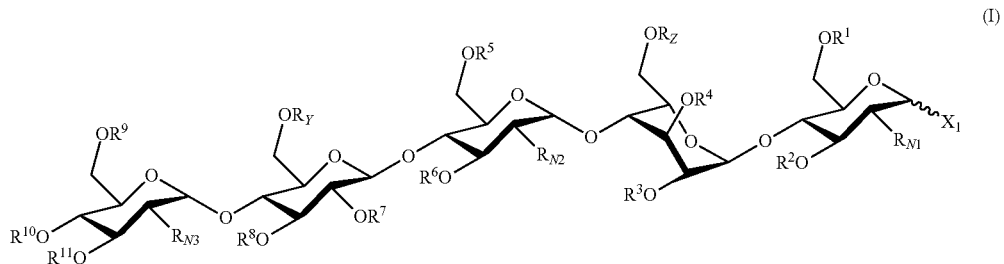

or a salt thereof;

the method comprising:
reacting a tetrasaccharide of formula (II):

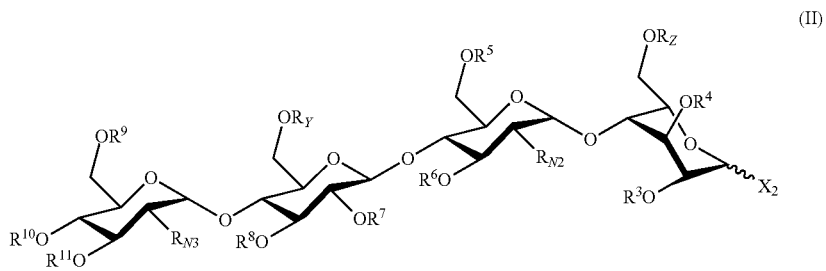

with monosaccharide E:

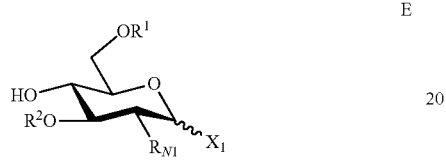

under suitable conditions to form a pentasaccharide of formula (I);
wherein $X_1$, $R^1$, $R^2$, $R^3$, $R^4$, $R^5$, $R^6$, $R^7$, $R^8$, $R^9$, $R^{10}$, $R^{11}$, $R_Y$, $R_Z$, $R_{N1}$, $R_{N2}$, and $R_{N3}$ are as described herein.

In another aspect, the present disclosure provides methods of synthesizing fondaparinux:

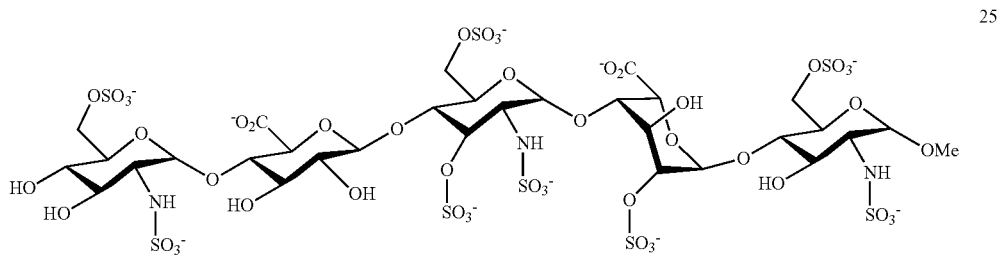

or a salt thereof;
the method comprising:
(a) deprotecting a pentasaccharide of formula (I'):

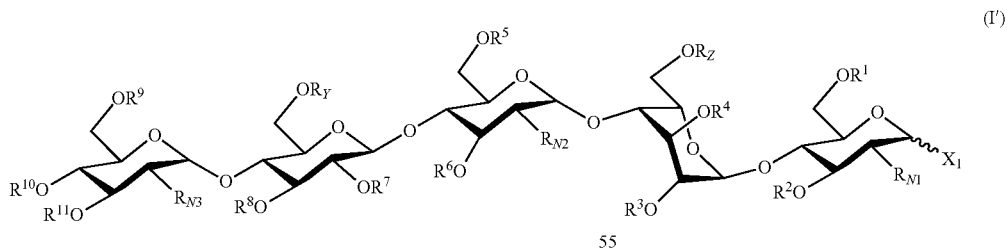

under suitable conditions to form a compound of formula (IX):

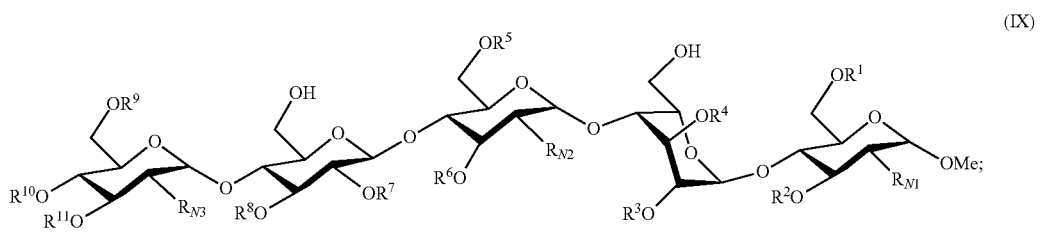

(b) oxidizing, deprotecting, and esterifying the compound of formula (IX) under suitable conditions to form a compound of formula (X):

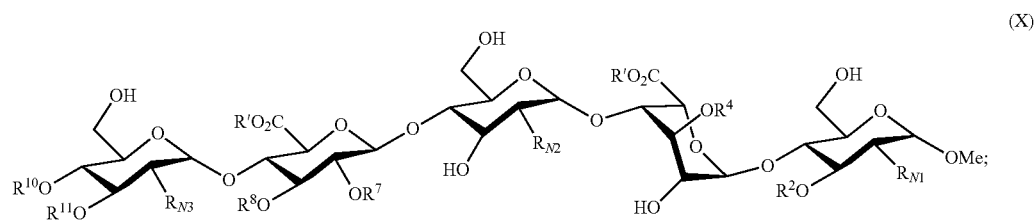

(X)

(c) sulfonating the compound of formula (X) under suitable conditions to form a compound of formula (XI):

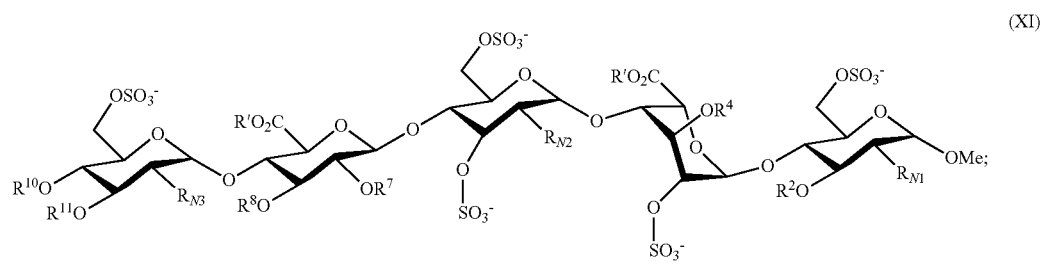

(XI)

(d) converting the compound of formula (XI) to a compound of formula (XII) under suitable conditions:

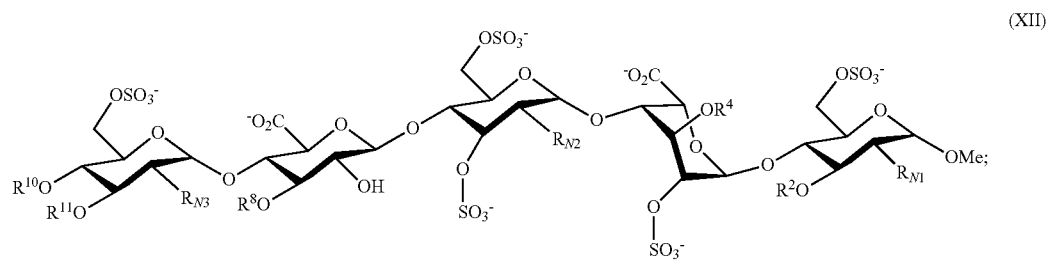

(XII)

(e) deprotecting the compound of formula (XII) under suitable conditions to form a compound of formula (XIII):

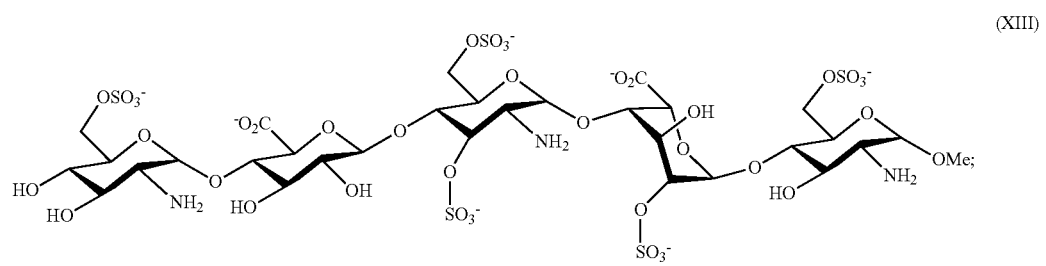

(XIII)

and (f) sulfonating the compound of formula (XIII) under suitable conditions to form fondaparinux 25,
wherein $X_1$, R', $R^1$, $R^2$, $R^3$, $R^4$, $R^5$, $R^6$, $R^7$, $R^8$, $R^9$, $R^{10}$, $R^{11}$, $R_Y$, $R_Z$, $R_{N1}$, $R_{N2}$, and $R_{N3}$ are as describe herein.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and subrange within the range. For example, an "alkyl group having from 1 to 6 carbons" (also referred to herein as "$C_{1-6}$ alkyl") is intended to encompass 1 ($C_1$ alkyl), 2 ($C_2$ alkyl), 3 ($C_3$ alkyl), 4 ($C_4$ alkyl), 5 ($C_5$ alkyl) and 6 ($C_6$ alkyl) carbons, and a range of 1 to 6 ($C_{1-6}$ alkyl), 1 to 5 ($C_{1-5}$ alkyl), 1 to 4 ($C_{1-4}$ alkyl), 1 to 3 ($C_{1-3}$ alkyl), 1 to 2 ($C_{1-2}$ alkyl), 2 to 6 ($C_{2-6}$ alkyl), 2 to 5 ($C_{2-5}$ alkyl), 2 to 4 ($C_{2-4}$ alkyl), 2 to 3 ($C_{2-3}$ alkyl), 3 to 6 ($C_{3-6}$ alkyl), 3 to 5 ($C_{3-5}$ alkyl), 3 to 4 ($C_{3-4}$ alkyl), 4 to 6 ($C_{4-6}$ alkyl), 4 to 5 ($C_{4-5}$ alkyl), and 5 to 6 ($C_{5-6}$ alkyl) carbons.

The term "aliphatic," as used herein, refers to a monoradical of a nonaromatic, saturated or unsaturated, unbranched ("straightchain") or branched, substituted or unsubstituted, acyclic hydrocarbon having 1-50 carbon atoms (i.e., $C_{1-50}$ aliphatic). Thus, as used herein, the term "aliphatic" encompasses the groups "alkyl", "alkynyl", and "alkenyl" as defined herein. In certain embodiments, aliphatic refers to a $C_2$-$C_{30}$ aliphatic group. In certain embodiments, aliphatic refers to a $C_5$-$C_{25}$ aliphatic group. In certain embodiments, aliphatic refers to a $C_1$-$C_{10}$ aliphatic group. In certain embodiments, aliphatic refers to a $C_{10}$-$C_{20}$ aliphatic group. In certain embodiments, aliphatic refers to a $C_{11}$-$C_{15}$ aliphatic group. Unless otherwise specified, each instance of aliphatic is independently unsubstituted ("unsubstituted aliphatic") or substituted ("substituted aliphatic") with 1, 2, 3, 4, 5, 6, 7, 8, 9, 10, or more substituents as described herein. Aliphatic group substituents include, but are not limited to, any of the monovalent or divalent substituents described herein, that result in the formation of a stable moiety.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The term "alkylene" as used herein refers to a bivalent alkyl group. An "alkylene" group is a polymethylene group, i.e., —(CH$_2$)$_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. It will be appreciated that an aryl group may be attached via an alkyl moiety to form an "alkylaryl" group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "imidoyl" as used herein refers to a group of formula —C(=NR*)R*, wherein each occurrence of R* is optionally substituted alkyl, aryl, or heteroaryl.

In some embodiments, aliphatic (e.g., alkyl, alkenyl, alkynyl), heteroaliphatic (e.g., heteroalkyl, heteroalkenyl, heteroalkynyl), carbocyclyl, heterocyclyl, aryl and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" heteroaliphatic, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted" means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Exemplary monovalent carbon atoms substituents include, but are not limited to, halo/halogen (i.e., —F, —Br, —Cl, —I), —NC, —CN, —NO$_2$, —N$_3$, —CO$_2$H, —CHO, —SO$_2$H, —SO$_3$H, —S(=O)OH, acyl (e.g., —C(=O)R$^A$, —CO$_2$R$^A$, —C(=O)—O—C(=O)R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$), amino (e.g., —NH$_2$, —N(OR$^B$)R$^B$, —N(R$^B$)$_2$, —NR$^B$SO$_2$R$^A$, —NR$^B$C(=O)R$^A$, —NR$^B$CO$_2$R$^A$, —NR$^B$C(=O)N(R$^B$)$_2$, —NR$^B$C(=NR$^B$)N(R$^B$)$_2$), thio (e.g., —SH, —SR$^A$, —SSR$^B$), oxy (e.g., —OH, —OR$^A$, —ON(R$^B$)$_2$, —OSO$_2$R$^A$, —OS(=O)R$^A$, —OC(=O)R$^A$, —OCO$_2$R$^A$, —OC(=O)N(R$^B$)$_2$, —OC(=NR$^B$)R$^A$, —OC(=NR$^B$)OR$^A$, —OC(=NR$^B$)N(R$^B$)$_2$), sulfonyl (e.g., —SO$_2$R$^A$, —SO$_2$OR$^A$, —SO$_2$N(R$^B$)$_2$), sulfinyl (e.g., —S(=O)R$^A$), silyl (e.g., —Si(R$^A$)$_3$), $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 $R^D$ groups;

each instance of $R^A$ is, independently, selected from the group consisting of $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 $R^D$ groups;

each instance of $R^B$ is, independently, selected from the group consisting of hydrogen, —OH, —$OR^A$, —$N(R^C)_2$, —CN, —C(=O)$R^A$, —C(=O)N($R^C$)$_2$, —$CO_2R^A$, —$SO_2R^A$, —C(=$NR^C$)$OR^A$, —C(=$NR^C$)N($R^C$)$_2$, —$SO_2$N($R^C$)$_2$, —$SO_2R^C$, —$SO_2OR^C$, —$SOR^A$, —C(=S)N($R^C$)$_2$, —C(=O)$SR^C$, —C(=S)$SR^C$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^B$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 $R^D$ groups;

each instance of $R^C$ is, independently, selected from the group consisting of hydrogen, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^C$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 $R^D$ groups; and each instance of $R^D$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —S(=O)$C_{1-6}$ alkyl, $C_{1-6}$ alkyl, $C_{1-6}$ fluoroalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^D$ substituents are joined to form =O, =S or =$NR^B$.

Exemplary divalent carbon atom substituents include, but are not limited to =O, =S, and =$NR^B$, wherein $R^B$ is as defined herein.

Nitrogen atoms can be substituted or unsubstituted as valency permits, and include primary, secondary, tertiary and quarternary nitrogen atoms. Exemplary nitrogen atom substitutents include, but are not limited to, =$NR^B$, —CHO, —C(=O)$R^A$, —$CO_2R^A$, —C(=O)$SR^A$, —C(=O)N($R^B$)$_2$, —C(=O)$NR^BSO_2R^A$, —C(=$NR^B$)$R^A$, —C(=$NR^B$)$OR^A$, —C(=$NR^B$)N($R^B$)$_2$, —C(=S)$R^A$, —C(=S)N($R^A$)$_2$, —C(=S)$SR^A$, —$NH_2$, —N($OR^B$)$R^B$, —N($R^B$)$_2$, —$NR^BSO_2R^A$, —$NR^BC$(=O)$R^A$, —$NR^BCO_2R^A$, —$NR^BC$(=O)N($R^B$)$_2$, —$NR^BC$(=$NR^B$)N($R^B$)$_2$, —OH, —$OR^A$, —$SO_2R^A$, —$SO_2OR^A$, —$SO_2N(R^B)_2$, —S(=O)$R^A$), —Si ($R^A$)$_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups.

In certain embodiments, nitrogen atom substituents, as described above, are also referred to as "amino protecting groups" or "nitrogen protecting groups". Amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

Exemplary amino protecting groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DBtBOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), pmethoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N-'dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di-(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Exemplary oxygen substituents include, but are not limited to, —C(=O)R$^A$, —CO$_2$R$^A$, —C(=O)—O—C(=O) R$^A$, —C(=O)SR$^A$, —C(=O)N(R$^B$)$_2$, —C(=O) NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$, —SO$_2$R$^A$, —SO$_2$OR$^A$, —SO$_2$N(R$^B$)$_2$, —S(=O)R$^A$, —Si(R$^A$)$_3$, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^D$ groups.

In certain embodiments, oxygen atom substituents, as described above, are also referred to as "hydroxyl protecting groups" or "oxygen protecting groups". Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary hydroxyl protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain embodiments, a compound of the present invention is provided as a salt. Salts are well known in the art. For example, Berge et al., describe pharmaceutically acceptable salts in detail in *J. Pharmaceutical Sciences,* 1977, 66, 1-19, incorporated herein by reference. Salts of the compounds of this invention include those derived from suitable inorganic and organic acids and bases. Examples include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, ptoluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further salts include, when appropriate, ammonium, quaternary ammonium, and amine cations formed using counterions such as halide, hydroxide, carboxylate, sulfate, phosphate, nitrate, loweralkyl sulfonate and aryl sulfonate.

The term "leaving group," as used herein, refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, chloride, bromide, iodide, tosyl, triflate, sulfonate, mesylate, dimethyl sulfonate, fluorosulfonate, methyl tosylate, brosylate, nosylate, or —S-tolyl. Non-limiting characteristics and examples of leaving groups can be found, for example in *Organic Chemistry,* 2d ed., Francis Carey (1992), pages 328-331; *Introduction to Organic Chemistry,* 2d ed., Andrew John McMurry (2000), pages 398 and 408; each of which are incorporated herein by reference for the limited purpose of disclosing characteristics and examples of leaving groups.

Any of the compounds described herein may be in a variety of forms, such as, but not limited to, salts, solvates, hydrates, tautomers, and isomers.

In certain embodiments, the compound described herein may exist in various tautomeric forms. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diasteromers, etc.). For example, "isomer" includes cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables*

*of Resolving Agents and Optical Resolutions* p. 268 (E. L. Eliel, Ed., Univ. of Notre Dame Press, Notre Dame, Ind. 1972).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

It must be noted that as used herein and in the appended claims, the singular forms "a," "and," and "the" include plural referents unless the context clearly dictates otherwise. Thus, for example, reference to "a biomarker" includes a plurality of such biomarkers and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 is a schematic illustration of a synthesis of exemplary monosaccharides of formulae A, C and E.

FIG. 3 is a schematic illustration of a synthesis of an exemplary monosaccharide of formula B.

FIG. 4 is a schematic illustration of a synthesis of an exemplary monosaccharide of formula D.

FIG. 5 is a schematic illustration of a synthesis of disaccharide acceptor 14.

FIG. 6 is a schematic illustration of a synthesis of trisaccharide acceptor 16.

FIG. 7 is a schematic illustration of a synthesis of tetrasaccharide donor 18.

FIG. 8 is a schematic illustration of a synthesis of pentasaccharide building block 19.

FIG. 9 is a schematic illustration of a synthesis of fondaparinux from pentasaccharide building block acceptor 19.

FIG. 12 is a schematic illustration of a synthesis of disaccharide donor 28.

FIG. 13 is a schematic illustration of an alternate synthesis of tetrasaccharide donor 18.

DETAILED DESCRIPTION OF CERTAIN EMBODIMENTS

Fondaparinux is a linear octasulfated pentasaccharide having five O-sulfated moieties and three N-sulfated moieties. In addition, fondaparinux contains six hydroxyl groups that are not sulfated. Fondaparinux contains three glucosamine derivatives, one glucuronic acid, and one L-iduronic acid. The five saccharides are connected to each other in alternate α and β linkages (FIG. 1).

Figure 1:
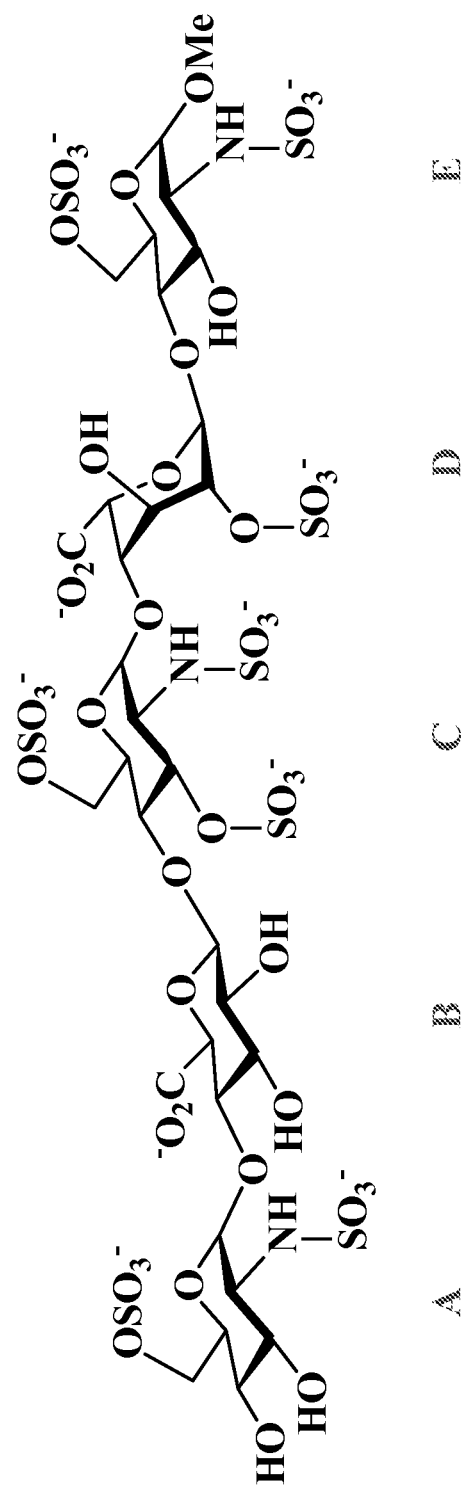
FIG. 1 is a schematic illustration of fondaparinux (Arixtra®)
Figure 10:
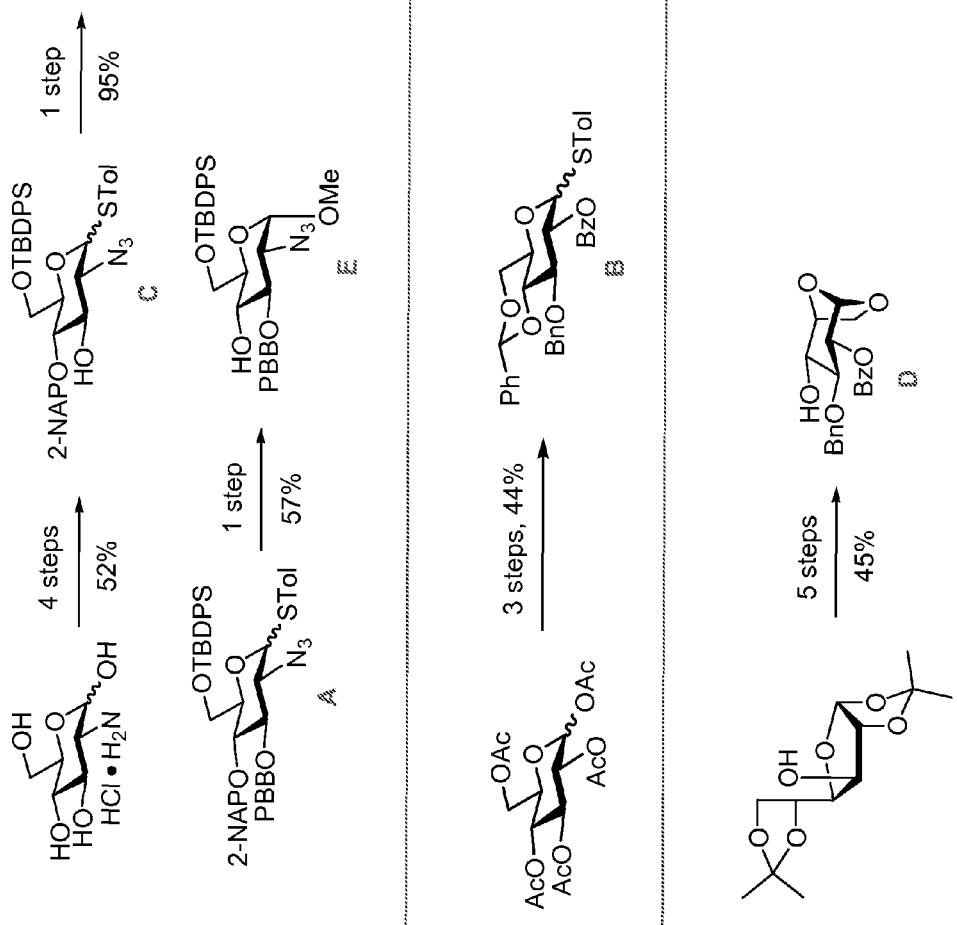
FIG. 10 depicts a summary of exemplary monosaccharide syntheses.
Figure 11:
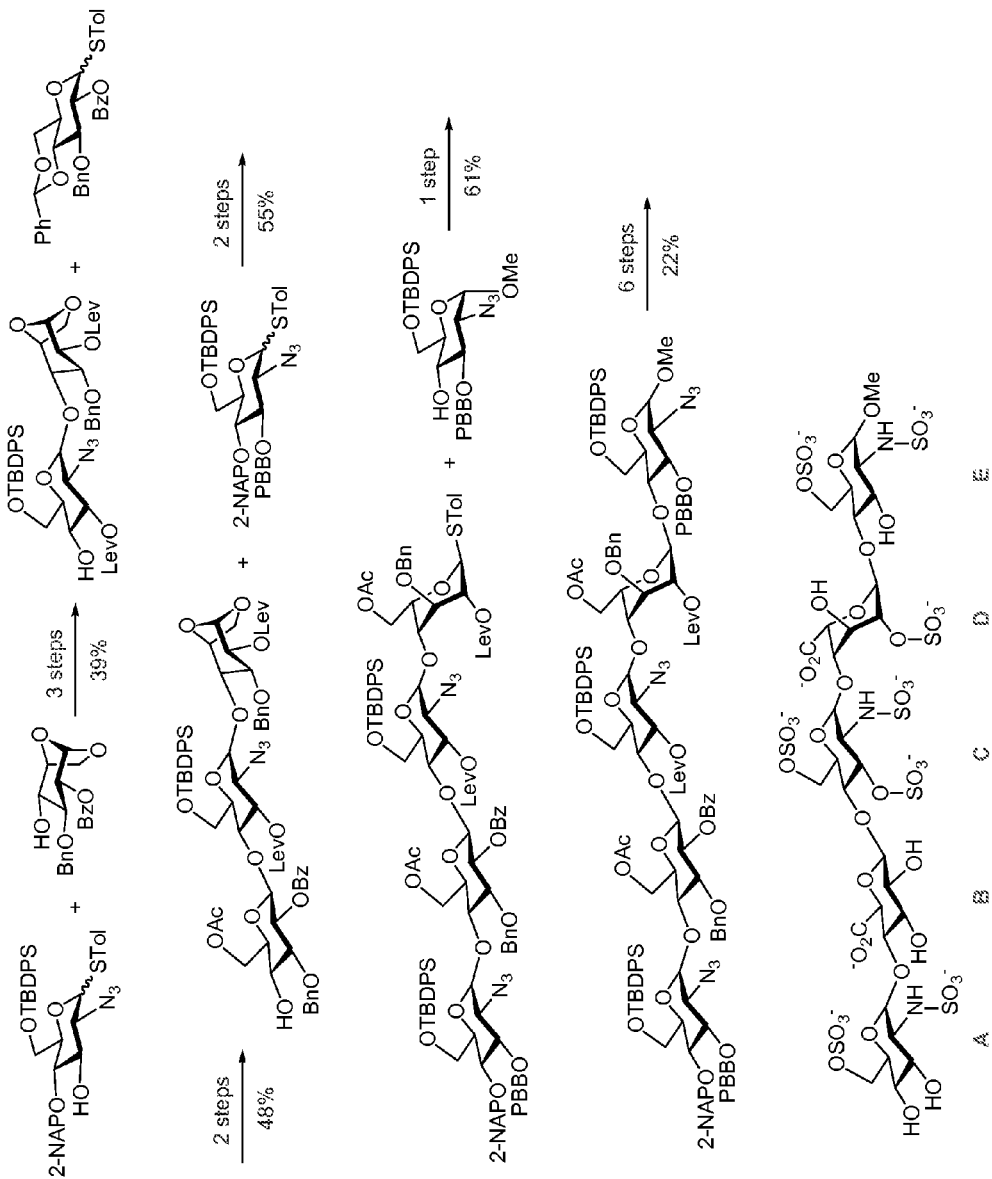
FIG. 11 depicts a summary of an exemplary synthesis of fondaparinux.

The monosaccharide units that form the building blocks for the fondaparinux molecule are labeled with the glucosamine unit on the left referred to as monosaccharide A and the next, an uronic acid unit to its right as B and subsequent monosaccharide units, C, D and E respectively as shown in FIG. 1.

In certain embodiments, the present invention relates to a new synthetic route to fondaparinux. In the synthesis of fondaparinux, the monosaccharides of formulae A, B, C, D and E described herein can be made either by methods described in the art or by methods described herein. In other embodiments, the present invention relates to intermediates useful for the synthesis of fondaparinux. In some embodiments, an compound described herein is also useful as an antithrombotic agent. In certain embodiments, the present invention provides compounds or compositions comprising provided compounds, for use in inhibiting factor Xa.

In some embodiments, the present invention provides a compound of Formula (I):

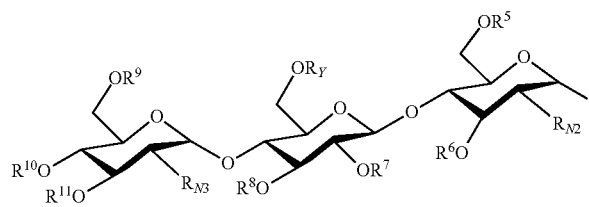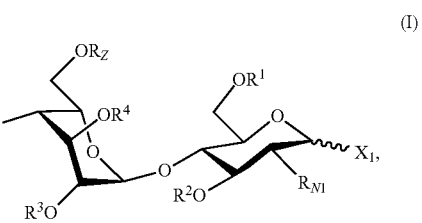

(I)

wherein:
$X_1$ is —$OR^A$ or —$SR^A$, wherein $R^A$ is hydrogen, a oxygen or sulfur protecting group, optionally substituted $C_{1-10}$ alkyl, optionally substituted aryl, optionally substituted acyl, or optionally substituted imidoyl;
$R^2$ and $R^{11}$ are independently optionally substituted arylalkyl;
$R_{N1}$, $R_{N2}$, and $R_{N3}$ are independently —$N_3$ or —$N(R^W)_2$, wherein each $R^W$ is independently hydrogen or an amino protecting group;
$R^3$ and $R^6$ are independently —$C(O)R^D$, wherein each occurrence of $R^D$ is independently optionally substituted alkyl or optionally substituted aryl;
$R^1$, $R^5$, and $R^9$ are independently selected from the group consisting of optionally substituted arylalkyl and —$Si(R^B)_3$, wherein each $R^B$ is independently alkyl or aryl;
$R^{10}$ is optionally substituted arylalkyl;
$R_Y$ and $R_Z$ are independently hydrogen or an oxygen protecting group;
$R^7$ is selected from the group consisting of —$Si(R^B)_3$, optionally substituted arylalkyl, and —$C(O)R^C$, wherein $R^C$ is optionally substituted alkyl, optionally substituted aryl, or optionally substituted arylalkyl; and
$R^4$ and $R^8$ are independently optionally substituted arylalkyl;
or a salt thereof.

In some embodiments, for the formulae described herein, $X_1$ is —$OR^A$ or —$SR^A$, wherein $R^A$ is hydrogen, an oxygen or sulfur protecting group, optionally substituted $C_{1-10}$ alkyl, optionally substituted aryl, optionally substituted acyl, or optionally substituted imidoyl.

In certain embodiments, $X_1$ is in the alpha configuration. In certain embodiments, $X_1$ is in the beta configuration.

In some embodiments, $X_1$ is —$OR^A$. In some embodiments, $X_1$ is —OH. In some embodiments, $X_1$ is —O(protecting group). In some embodiments, $X_1$ is —$OR^A$, wherein $R^A$ is unsubstituted $C_{1-10}$ alkyl. In some embodiments, $X_1$ is —$OR^A$, wherein $R^A$ is substituted $C_{1-10}$ alkyl. In some embodiments, $X_1$ is —$OR^A$, wherein $R^A$ is unsubstituted aryl. In some embodiments, $X_1$ is —$OR^A$, wherein $R^A$ is substituted aryl. In some embodiments, $X_1$ is —$OR^A$, wherein $R^A$ is unsubstituted acyl. In some embodiments, $X_1$ is $OR^A$, wherein $R^A$ is substituted acyl. In some embodiments, $X_1$ is $OR^A$, wherein $R^A$ is unsubstituted imidoyl. In some embodiments, $X_1$ is —$OR^A$, wherein $R^A$ is substituted imidoyl.

In some embodiments, $X_1$ is —$SR^A$. In some embodiments, $X_1$ is —SH. In some embodiments, $X_1$ is —S (protecting group). In some embodiments, $X_1$ is —$SR^A$, wherein $R^A$ is unsubstituted $C_{1-10}$ alkyl. In some embodiments, $X_1$ is —$SR^A$, wherein $R^A$ is substituted $C_{1-10}$ alkyl. In certain embodiments, $X_1$ is —$SCH_3$. In some embodiments, $X_1$ is —$SR^A$, wherein $R^A$ is unsubstituted aryl. In some embodiments, $X_1$ is —$SR^A$, wherein $R^A$ is substituted aryl. In some embodiments, $X_1$ is —$SR^A$, wherein $R^A$ is unsubstituted acyl. In some embodiments, $X_1$ is —$SR^A$, wherein $R^A$ is substituted acyl. In some embodiments, $X_1$ is —$SR^A$, wherein $R^A$ is unsubstituted imidoyl. In some embodiments, $X_1$ is —$SR^A$, wherein $R^A$ is substituted imidoyl.

In some embodiments, $X_1$ is $C_{1-10}$ alkoxy. In some embodiments, $X_1$ is $C_{1-3}$ alkoxy. In certain embodiments, $X_1$ is methoxy. In certain embodiments, $X_1$ is alpha-methoxy.

In some embodiments, $X_1$ is selected from the group consisting of alpha-thiomethyl, beta-thiomethyl, alpha-thiocresyl, beta-thiocresyl, alpha-t-butyldiphenylsilyloxy, beta-t-butyldiphenylsilyloxy, and alpha-methoxy.

In some embodiments, for the formulae described herein, $R^1$ is selected from the group consisting of optionally substituted arylalkyl and —$Si(R^B)_3$, wherein each $R^B$ is independently alkyl or aryl. In some embodiments, $R^1$ is unsubstituted arylalkyl. In some embodiments, $R^1$ is substituted arylalkyl. In some embodiments, $R^1$ is benzyl. In some embodiments, $R^1$ is —$Si(R^B)_3$, wherein each $R^B$ is independently alkyl or aryl. In certain embodiments, $R^1$ is trimethylsilyl, triethylsilyl, dimethylisopropylsilyl, diethylisopropylsilyl, t-butyldimethylsilyl, t-butyldiphenylsilyl, or triisopropylsilyl. In certain embodiments, $R^1$ is t-butyldiphenylsilyl.

In some embodiments, for the formulae described herein, $R^2$ is optionally substituted arylalkyl. In some embodiments, $R^2$ is substituted arylalkyl. In some embodiments, $R^2$ is unsubstituted arylalkyl. In some embodiments, $R^2$ is unsubstituted benzyl. In some embodiments, $R^2$ is substituted benzyl. In some embodiments, $R^2$ is bromobenzyl. In certain embodiments, $R^2$ is p-bromobenzyl.

In some embodiments, for the formulae described herein, $R^3$ is —$C(O)R^D$, wherein $R^D$ is optionally substituted alkyl or optionally substituted aryl. In some embodiments, $R^D$ is optionally substituted alkyl. In some embodiments, $R^D$ is optionally substituted aryl. In some embodiments, $R^D$ is substituted alkyl. In some embodiments, $R^D$ is unsubstituted alkyl. In some embodiments, $R^D$ is substituted aryl. In some embodiments, $R^D$ is unsubstituted aryl. In certain embodiments, $R^3$ is acetyl. In certain embodiments, $R^3$ is chloroacetyl. In certain embodiments, $R^3$ is benzoyl. In certain embodiments, $R^3$ is levulinyl.

In some embodiments, for the formulae described herein, $R^4$ is optionally substituted arylalkyl. In some embodiments, $R^4$ is substituted arylalkyl. In some embodiments, $R^4$ is unsubstituted arylalkyl. In some embodiments, $R^4$ is unsubstituted benzyl. In some embodiments, $R^4$ is substituted benzyl.

In some embodiments, for the formulae described herein, $R^5$ is selected from the group consisting of optionally substituted arylalkyl and —$Si(R^B)_3$, wherein each $R^B$ is independently alkyl or aryl. In some embodiments, $R^5$ is unsubstituted arylalkyl. In some embodiments, $R^5$ is substituted arylalkyl. In some embodiments, $R^5$ is benzyl. In some embodiments, $R^5$ is —$Si(R^B)_3$, wherein each $R^B$ is independently alkyl or aryl. In certain embodiments, $R^5$ is trimethylsilyl, triethylsilyl, dimethylisopropylsilyl, diethylisopropylsilyl, t-butyldimethylsilyl, t-butyldiphenylsilyl, or triisopropylsilyl. In certain embodiments, $R^5$ is t-butyldiphenylsilyl.

In some embodiments, for the formulae described herein, $R^6$ is $C(O)R^D$, wherein $R^D$ is optionally substituted alkyl or optionally substituted aryl. In some embodiments, $R^D$ is optionally substituted alkyl. In some embodiments, $R^D$ is optionally substituted aryl. In some embodiments, $R^D$ is substituted alkyl. In some embodiments, $R^D$ is unsubstituted alkyl. In some embodiments, $R^D$ is substituted aryl. In some embodiments, $R^D$ is unsubstituted aryl. In certain embodiments, $R^6$ is acetyl. In certain embodiments, $R^6$ is chloroacetyl. In certain embodiments, $R^6$ is benzoyl. In certain embodiments, $R^6$ is levulinyl.

In some embodiments, for the formulae described herein, $R^7$ is selected from the group consisting of —Si($R^B$)$_3$, optionally substituted arylalkyl, and —C(O)$R^C$. In some embodiments, $R^7$ is —Si($R^B$)$_3$, wherein each $R^B$ is independently alkyl or aryl. In some embodiments, $R^7$ is optionally substituted arylalkyl. In some embodiments, $R^7$ is —C(O)$R^C$, wherein $R^C$ is optionally substituted alkyl, optionally substituted aryl, or optionally substituted arylalkyl. In some embodiments, $R^7$ is unsubstituted arylalkyl. In some embodiments, $R^7$ is substituted arylalkyl. In some embodiments, $R^7$ is benzyl. In some embodiments, $R^7$ is —Si($R^B$)$_3$, wherein each $R^B$ is independently alkyl or aryl. In certain embodiments, $R^7$ is trimethylsilyl, triethylsilyl, dimethylisopropylsilyl, diethylisopropylsilyl, t-butyldimethylsilyl, t-butyldiphenylsilyl, or triisopropylsilyl. In certain embodiments, $R^7$ is t-butyldiphenylsilyl. In some embodiments, $R^7$ is —C(O)$R^C$, wherein $R^C$ is optionally substituted alkyl. In some embodiments, $R^7$ is —C(O)$R^C$, wherein $R^C$ is unsubstituted alkyl. In some embodiments, $R^7$ is —C(O)$R^C$, wherein $R^C$ is substituted alkyl. In some embodiments, $R^7$ is —C(O)$R^C$, wherein $R^C$ is haloalkyl. In some embodiments, $R^7$ is —C(O)$R^C$, wherein $R^C$ is optionally substituted aryl. In some embodiments, $R^7$ is —C(O)$R^C$, wherein $R^C$ is substituted aryl. In some embodiments, $R^7$ is C(O)$R^C$, wherein $R^C$ is unsubstituted aryl. In certain embodiments, $R^7$ is benzoyl. In some embodiments, $R^7$ is —C(O)$R^C$, wherein $R^C$ is optionally substituted arylalkyl. In some embodiments, $R^7$ is —C(O)$R^C$, wherein $R^C$ is substituted arylalkyl. In some embodiments, $R^7$ is —C(O)$R^C$, wherein $R^C$ is unsubstituted arylalkyl.

In some embodiments, for the formulae described herein, $R^8$ is optionally substituted arylalkyl. In some embodiments, $R^8$ is substituted arylalkyl. In some embodiments, $R^8$ is unsubstituted arylalkyl. In some embodiments, $R^8$ is unsubstituted benzyl. In some embodiments, $R^8$ is substituted benzyl.

In some embodiments, for the formulae described herein, $R^9$ is selected from the group consisting of optionally substituted arylalkyl and Si($R^B$)$_3$, wherein each $R^B$ is independently alkyl or aryl. In some embodiments, $R^9$ is unsubstituted arylalkyl. In some embodiments, $R^9$ is substituted arylalkyl. In some embodiments, $R^9$ is benzyl. In some embodiments, $R^9$ is Si($R^B$)$_3$, wherein each $R^B$ is independently alkyl or aryl. In certain embodiments, $R^9$ is trimethylsilyl, triethylsilyl, dimethylisopropylsilyl, diethylisopropylsilyl, t-butyldimethylsilyl, t-butyldiphenylsilyl, or triisopropylsilyl. In certain embodiments, $R^9$ is t-butyldiphenylsilyl.

In some embodiments, for the formulae described herein, $R^{10}$ is optionally substituted arylalkyl. In some embodiments, $R^{10}$ is substituted arylalkyl. In some embodiments, $R^{10}$ is unsubstituted arylalkyl. In some embodiments, $R^{10}$ is unsubstituted benzyl. In some embodiments, $R^{10}$ is substituted benzyl. In some embodiments, $R^{10}$ is unsubstituted naphthylmethyl. In some embodiments, $R^{10}$ is substituted naphthylmethyl. In certain embodiments, $R^{10}$ is 2-naphthylmethyl (2-NAP).

In some embodiments, for the formulae described herein, $R^{11}$ is optionally substituted arylalkyl. In some embodiments, $R^{11}$ is substituted arylalkyl. In some embodiments, $R^{11}$ is unsubstituted arylalkyl. In some embodiments, $R^{11}$ is unsubstituted benzyl. In some embodiments, $R^{11}$ is substituted benzyl. In some embodiments, $R^{11}$ is bromobenzyl. In certain embodiments, $R^{11}$ is p-bromobenzyl (PBB).

In some embodiments, for the formulae described herein, $R_Y$ is hydrogen or an oxygen protecting group. In some embodiments, $R_Y$ is hydrogen. In some embodiments, $R_Y$ is an oxygen protecting group. In certain embodiments, $R_Y$ is an acyl group. In certain embodiments, $R_Y$ is acetyl. In certain embodiments, $R_Y$ is chloroacetyl. In certain embodiments, $R_Y$ is methoxyacetyl. In certain embodiments, $R_Y$ is trichloroacetyl.

In some embodiments, for the formulae described herein, $R_Z$ is hydrogen or an oxygen protecting group. In some embodiments, $R_Z$ is hydrogen. In some embodiments, $R_Z$ is an oxygen protecting group. In certain embodiments, $R_Z$ is an acyl group. In certain embodiments, $R_Z$ is acetyl. In certain embodiments, $R_Z$ is chloroacetyl. In certain embodiments, $R_Z$ is methoxyacetyl. In certain embodiments, $R_Z$ is trichloroacetyl.

In some embodiments, for the formulae described herein, $R_{N1}$ is —$N_3$ or —N($R^W$)$_2$, wherein each $R^W$ is independently hydrogen or a nitrogen protecting group. In certain embodiments, $R_{N1}$ is —$N_3$. In certain embodiments, $R_{N1}$ is —N($R^W$)$_2$, wherein each $R^W$ is independently hydrogen or a nitrogen protecting group. In certain embodiments, $R_{N1}$ is —$NH_2$. In certain embodiments, $R_{N1}$ is —$NHR^W$, wherein $R^W$ is a nitrogen protecting group. In certain embodiments, $R_{N1}$ is —N($R^W$)$_2$, wherein each $R^W$ is a nitrogen protecting group. In certain embodiments, $R_{N1}$ is selected from the group consisting of —$N_3$, —NH(Cbz), —NH(Boc), —NH(Fmoc), —NHC(O)CCl$_3$, —NHC(O)CH$_3$, and —N(C(O)CH$_3$)$_2$. In certain embodiments, $R_{N1}$ is —NH(Cbz). In certain embodiments, $R_{N1}$ is —NH(Fmoc). In certain embodiments, $R_{N1}$ is —NHC(O)CCl$_3$. In certain embodiments, $R_{N1}$ is —NHC(O)CH$_3$. In certain embodiments, $R_{N1}$ is —N(C(O)CH$_3$)$_2$.

In some embodiments, for the formulae described herein, $R_{N2}$ is —$N_3$ or —N($R^W$)$_2$, wherein each $R^W$ is independently hydrogen or a nitrogen protecting group. In certain embodiments, $R_{N2}$ is —$N_3$. In certain embodiments, $R_{N2}$ is —N($R^W$)$_2$, wherein each $R^W$ is independently hydrogen or a nitrogen protecting group. In certain embodiments, $R_{N2}$ is —$NH_2$. In certain embodiments, $R_{N2}$ is —$NHR^W$, wherein $R^W$ is a nitrogen protecting group. In certain embodiments, $R_{N2}$ is —N($R^W$)$_2$, wherein each $R^W$ is a nitrogen protecting group. In certain embodiments, $R_{N2}$ is selected from the group consisting of —$N_3$, —NH(Cbz), —NH(Boc), —NH(Fmoc), —NHC(O)CCl$_3$, —NHC(O)CH$_3$, and —N(C(O)CH$_3$)$_2$. In certain embodiments, $R_{N2}$ is —NH(Cbz). In certain embodiments, $R_{N2}$ is —NH(Fmoc). In certain embodiments, $R_{N2}$ is —NHC(O)CCl$_3$. In certain embodiments, $R_{N2}$ is —NHC(O)CH$_3$. In certain embodiments, $R_{N2}$ is —N(C(O)CH$_3$)$_2$.

In some embodiments, for the formulae described herein, $R_{N3}$ is —$N_3$ or —N($R^W$)$_2$, wherein each $R^W$ is independently hydrogen or a nitrogen protecting group. In certain embodiments, $R_{N3}$ is —$N_3$. In certain embodiments, $R_{N3}$ is —$N(R^W)_2$, wherein each $R^W$ is independently hydrogen or a nitrogen protecting group. In certain embodiments, $R_{N3}$ is —$NH_2$. In certain embodiments, $R_{N3}$ is —$NHR^W$, wherein $R^W$ is a nitrogen protecting group. In certain embodiments, $R_{N3}$ is —$N(R^W)_2$, wherein each $R^W$ is a nitrogen protecting group. In certain embodiments, $R_{N3}$ is selected from the group consisting of —$N_3$, —NH(Cbz), —NH(Boc), —NH(Fmoc), —NHC(O)CCl$_3$, —NHC(O)CH$_3$, and —N(C(O)CH$_3$)$_2$. In certain embodiments, $R_{N3}$ is —NH(Cbz). In certain embodiments, $R_{N3}$ is —NH(Fmoc). In certain embodiments, $R_{N3}$ is —NHC(O)CCl$_3$. In certain embodiments, $R_{N3}$ is —NHC(O)CH$_3$. In certain embodiments, $R_{N3}$ is —N(C(O)CH$_3$)$_2$.

In some embodiments, $R_{N1}$, $R_{N2}$, and $R_{N3}$ are the same. In some embodiments, $R_{N1}$, $R_{N2}$, and $R_{N3}$ are —$N_3$.

In some embodiments, $R^1$, $R^5$, and $R^9$ are the same. In some embodiments, $R^1$, $R^5$, and $R^9$ are each —Si($R^B$)$_3$. In some embodiments, $R^1$, $R^5$ and $R^9$ are t-butyldiphenylsilyl.

In some embodiments, $R^2$ and $R^{11}$ are the same. In some embodiments, $R^2$ and $R^{11}$ are each optionally substituted benzyl. In some embodiments, $R^2$ and $R^{11}$ are p-bromobenzyl.

In some embodiments, $R^1$, $R^5$ and $R^9$ are t-butyldiphenylsilyl; and $R^2$ and $R^{11}$ are p-bromobenzyl.

In some embodiments, $R^3$ and $R^6$ are the same. In some embodiments, $R^3$ and $R^6$ are levulinyl.

In some embodiments, $R^1$, $R^5$ and $R^9$ are t-butyldiphenylsilyl; and $R^3$ and $R^6$ are levulinyl.

In some embodiments, $R^1$, $R^5$ and $R^9$ are t-butyldiphenylsilyl; and $R^7$ is benzoyl.

In some embodiments, $R_Y$ and $R_Z$ are the same. In some embodiments, $R_Y$ and $R_Z$ are each a protecting group. In some embodiments, $R_Y$ and $R_Z$ are each an acyl protecting group. In some embodiments, $R_Y$ and $R_Z$ are acetyl.

In some embodiments, $R^1$, $R^5$ and $R^9$ are t-butyldiphenylsilyl; and $R_Y$ and $R_Z$ are acetyl.

In some embodiments, a provided compound is of Formula (I-a):

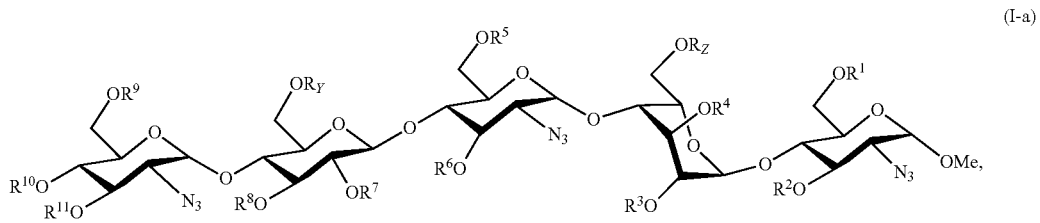

(I-a)

wherein $R^1$, $R^2$, $R^3$, $R^4$, $R^5$, $R^6$, $R^7$, $R^8$, $R^9$, $R^{10}$, $R^{11}$, $R_Y$, and $R_Z$ are as described herein.

In some embodiments, a provided compound is of Formula (I-b):

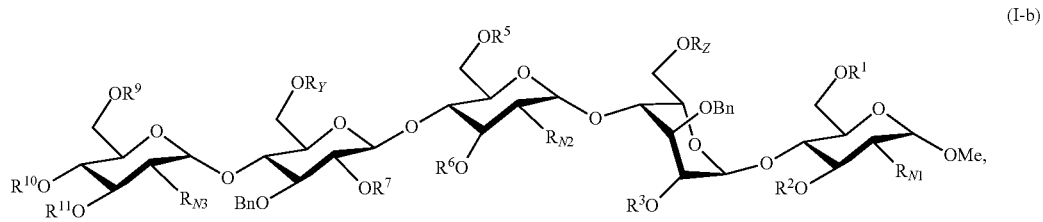

(I-b)

wherein $R^1$, $R^2$, $R^3$, $R^5$, $R^6$, $R^7$, $R^9$, $R^{10}$, $R^{11}$, $R_Y$, $R_Z$, $R_{N1}$, $R_{N2}$, and $R_{N3}$ are as described herein.

In some embodiments, a provided compound is of the formula:

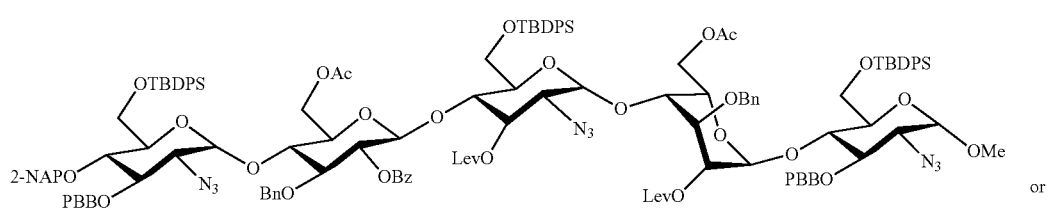

19 or

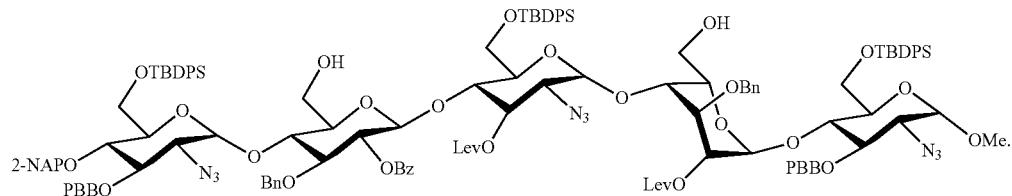

In some embodiments, the present invention provides a compound of Formula (II):

(II)

[structure of Formula (II)]

wherein:
$X_2$ is selected from the group consisting of a leaving group, —$OR^A$, or —$SR^A$, wherein $R^A$ is hydrogen, an oxygen or sulfur protecting group, optionally substituted $C_{1-10}$ alkyl, optionally substituted aryl, optionally substituted acyl, or optionally substituted imidoyl;
$R^{11}$ K is optionally substituted arylalkyl;
$R_{N2}$ and $R_{N3}$ are independently —$N_3$ or —$N(R^W)_2$, wherein each $R^W$ is independently hydrogen or a nitrogen protecting group;
$R^3$ and $R^6$ are independently —$C(O)R^D$, wherein each occurrence of $R^D$ is independently optionally substituted alkyl or optionally substituted aryl;
$R^5$ and $R^9$ are independently selected from the group consisting of optionally substituted arylalkyl and —Si$(R^B)_3$, wherein each $R^B$ is independently alkyl or aryl;
$R^{10}$ is optionally substituted arylalkyl;
$R_Y$ and $R_Z$ are independently hydrogen or an oxygen protecting group; or
$R_Z$ and $X_2$ are taken together with their intervening atoms to form a five-membered ring;
$R^7$ is selected from the group consisting of —Si$(R^B)_3$, optionally substituted arylalkyl, and —$C(O)R^C$, wherein $R^C$ is optionally substituted alkyl, optionally substituted aryl, or optionally substituted arylalkyl; and
$R^4$ and $R^8$ are independently optionally substituted arylalkyl; or a salt thereof.
$R^3$, $R^4$, $R^5$, $R^6$, $R^7$, $R^8$, $R^9$, $R^{10}$, $R^{11}$, $R_Y$, $R_Z$, $R_{N2}$, and $R_{N3}$ are further described in embodiments herein.

In some embodiments, $X_2$ is selected from the group consisting of a leaving group, —$OR^A$, or —$SR^A$, wherein $R^A$ is hydrogen, an oxygen or sulfur protecting group, optionally substituted $C_{1-10}$ alkyl, optionally substituted aryl, optionally substituted acyl, or optionally substituted imidoyl. In some embodiments, $X_2$ is —$OR^A$ or —$SR^A$, wherein $R^A$ is hydrogen, an oxygen or sulfur protecting group, optionally substituted $C_{1-10}$ alkyl, optionally substituted aryl, optionally substituted acyl, or optionally substituted imidoyl.

In certain embodiments, $X_2$ is in the alpha configuration. In certain embodiments, $X_2$ is in the beta configuration. In certain embodiments, $X_2$ is racemic.

In some embodiments, $X_2$ is —$OR^A$. In some embodiments, $X_2$ is —OH. In some embodiments, $X_2$ is —O(protecting group). In some embodiments, $X_2$ is —$OR^A$, wherein $R^A$ is unsubstituted $C_{1-10}$ alkyl. In some embodiments, $X_2$ is —$OR^A$, wherein $R^A$ is substituted $C_{1-10}$ alkyl. In some embodiments, $X_2$ is —$OR^A$, wherein $R^A$ is unsubstituted aryl. In some embodiments, $X_2$ is —$OR^A$, wherein $R^A$ is substituted aryl. In some embodiments, $X_2$ is —$OR^A$, wherein $R^A$ is unsubstituted acyl. In some embodiments, $X_2$ is —$OR^A$, wherein $R^A$ is substituted acyl. In some embodiments, $X_2$ is —$OR^A$, wherein $R^A$ is unsubstituted imidoyl. In some embodiments, $X_2$ is —$OR^A$, wherein $R^A$ is substituted imidoyl.

In some embodiments, $X_2$ is —$SR^A$. In some embodiments, $X_2$ is —SH. In some embodiments, $X_2$ is —S(protecting group). In some embodiments, $X_2$ is —$SR^A$, wherein $R^A$ is unsubstituted $C_{1-10}$ alkyl. In some embodiments, $X_2$ is —$SR^A$, wherein $R^A$ is substituted $C_{1-10}$ alkyl. In certain embodiments, $X_2$ is —$SCH_3$. In some embodiments, $X_2$ is —$SR^A$, wherein $R^A$ is unsubstituted aryl. In some embodiments, $X_2$ is —$SR^A$, wherein $R^A$ is substituted aryl. In some embodiments, $X_2$ is —$SR^A$, wherein $R^A$ is unsubstituted acyl. In some embodiments, $X_2$ is —$SR^A$, wherein $R^A$ is substituted acyl. In some embodiments, $X_2$ is —$SR^A$, wherein $R^A$ is unsubstituted imidoyl. In some embodiments, $X_2$ is —$SR^A$, wherein $R^A$ is substituted imidoyl.

In some embodiments, $X_2$ is $C_{1-10}$ alkoxy. In some embodiments, $X_2$ is $C_{1-3}$ alkoxy. In certain embodiments, $X_2$ is methoxy. In certain embodiments, $X_2$ is alpha-methoxy.

In some embodiments, $X_2$ is selected from the group consisting of alpha-thiomethyl, beta-thiomethyl, alpha-thiocresyl, beta-thiocresyl, alpha-t-butyldiphenylsilyloxy, beta-t-butyldiphenylsilyloxy, and alpha-methoxy.

In some embodiments, $X_2$ is a leaving group. In some embodiments, $X_2$ is selected from the group consisting of halogen, optionally substituted thioalkyl, optionally substituted thioaryl, —OC(=N)CCl$_3$, —OP(O)(OR$^F$)$_2$, and n-pentenyl, wherein $R^F$ is hydrogen, optionally substituted alkyl, or optionally substituted acyl.

In certain embodiments, $X_2$ is

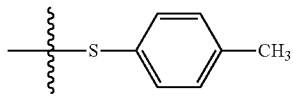

(abbreviated —S-tolyl). In certain embodiments, $X_2$ is —OH. In certain embodiments, $X_2$ is —OAc.

In certain embodiments, a provided compound is of Formula (II-a):

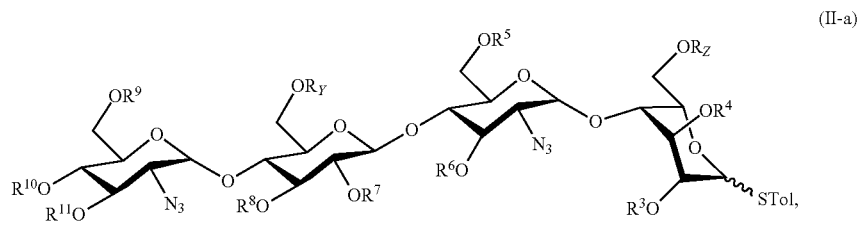

wherein $R^3$, $R^4$, $R^5$, $R^6$, $R^7$, $R^8$, $R^9$, $R^{10}$, $R^{11}$, $R_Y$, and $R_Z$ are as described herein.

In certain embodiments, a provided compound is of Formula (II-b):

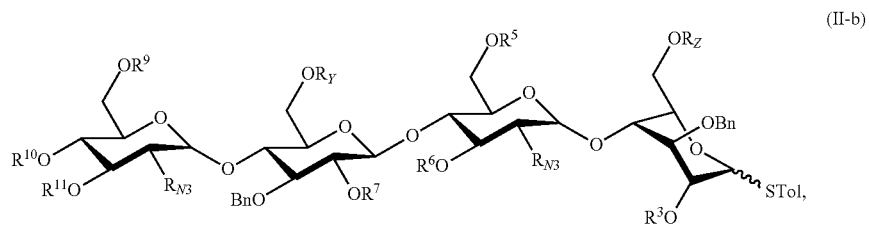

wherein $R^3$, $R^5$, $R^6$, $R^7$, $R^9$, $R^{10}$, $R^{11}$, $R_Y$, $R_Z$, $R_{N2}$, and $R_{N3}$ are as described herein.

In certain embodiments, a provided compound is of the formula:

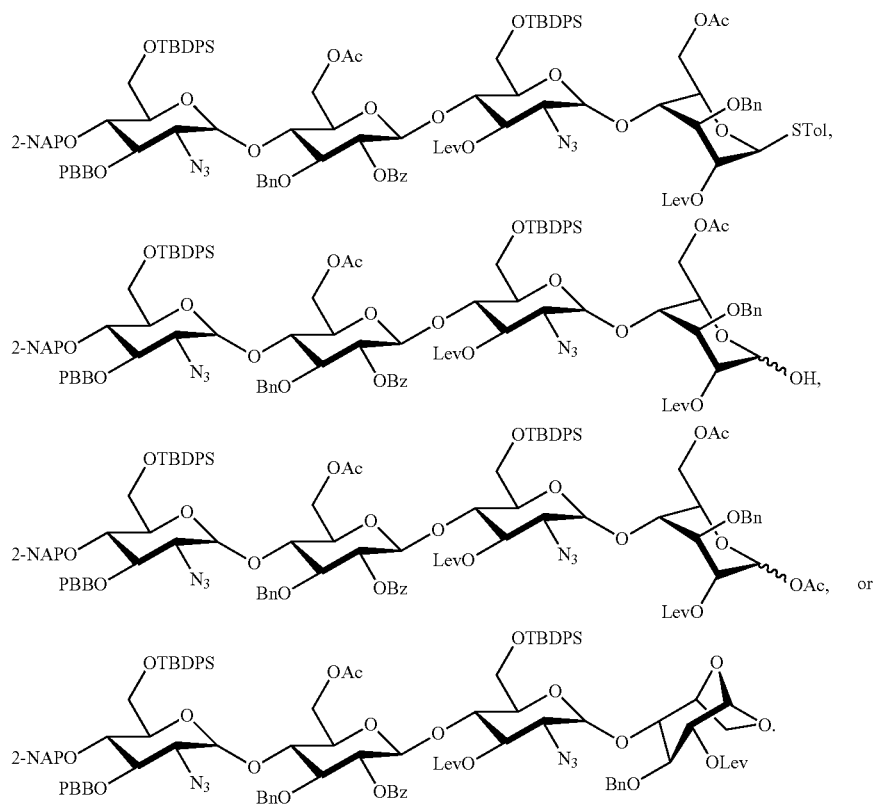

In another aspect, the present invention provides a compound of Formula (III):

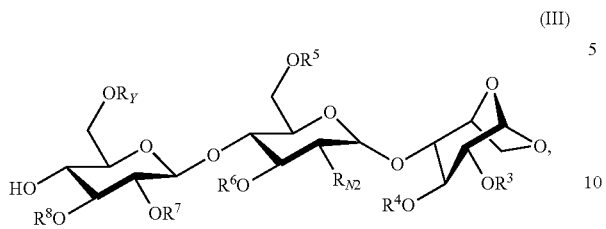
(III)

wherein:
$R_{N2}$ is —$N_3$ or —$N(R^W)_2$, wherein each $R^W$ is independently hydrogen or a nitrogen protecting group;
$R^3$ and $R^6$ are independently —$C(O)R^D$, wherein each occurrence of $R^D$ is independently optionally substituted alkyl or optionally substituted aryl;
$R^5$ is selected from the group consisting of optionally substituted arylalkyl and —$Si(R^B)_3$, wherein each $R^B$ is independently alkyl or aryl;
$R_Y$ is hydrogen or an oxygen protecting group;
$R^7$ is selected from the group consisting of —$Si(R^B)_3$, optionally substituted arylalkyl, and —$C(O)R^C$, wherein $R^C$ is optionally substituted alkyl, optionally substituted aryl, or optionally substituted arylalkyl; and
$R^4$ and $R^8$ are independently optionally substituted arylalkyl; or a salt thereof.
$R^3$, $R^4$, $R^5$, $R^6$, $R^7$, $R^8$, $R_Y$, and $R_{N2}$ are further described in embodiments herein.

In certain embodiments, a provided compound is of the formula:

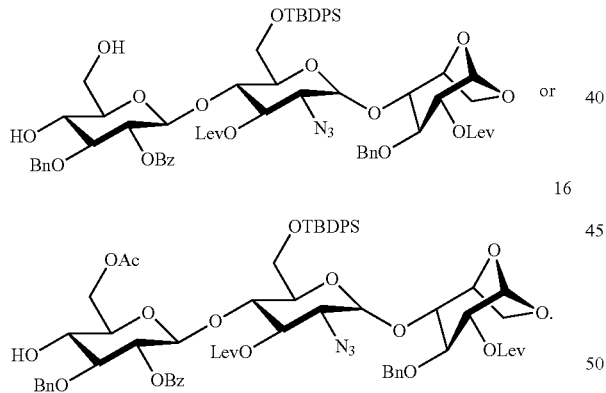
15
or
16

In another aspect, the present invention provides methods (Method A) for synthesizing a trisaccharide of formula (III):

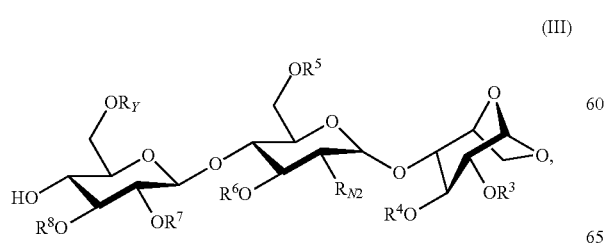
(III)

or a salt thereof;

the method comprising:
(a) reacting monosaccharides of formulae C and D;

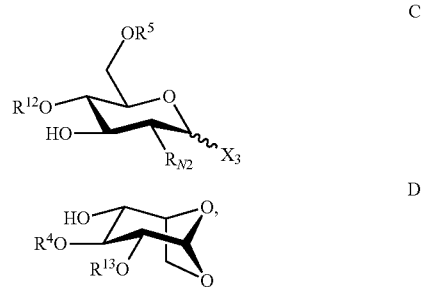
C

D wherein $R^{12}$ and $R^{13}$ are each independently an oxygen protecting group; and
$X_3$ is a leaving group;
in the presence of an activating agent under suitable conditions to form a disaccharide of formula (IV):

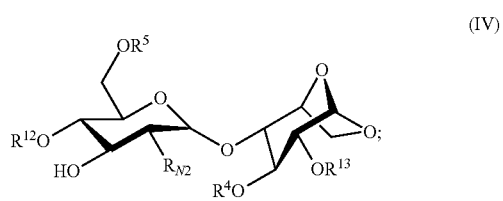
(IV)

(b) deprotecting the disaccharide of formula (IV) under suitable conditions to form a compound of formula (V):

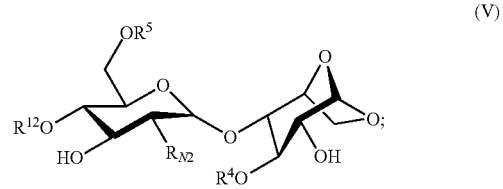
(V)

(c) protecting and deprotecting the compound of formula (V) under suitable conditions to form a compound of formula (VI):

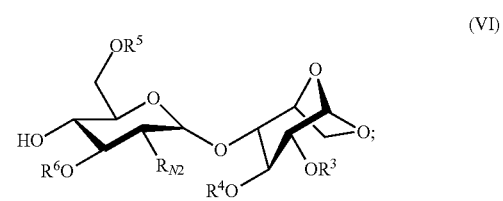
(VI)

(d) reacting the compound of formula (VI) with a monosaccharide of formula B:

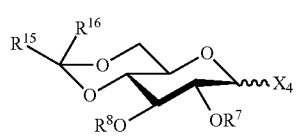
B wherein $R^{15}$ and $R^{16}$ are independently hydrogen, alkyl or aryl, wherein at least one of $R^{15}$ and $R^{16}$ is not hydrogen; and
$X_4$ is a leaving group;
in the presence of an activating agent under suitable conditions to form a trisaccharide of formula (VII):

(VII)

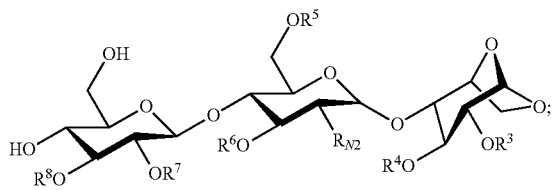

and (e) protecting the trisaccharide of formula (VII) under suitable conditions to form a trisaccharide of formula (III);
wherein $R^3$, $R^4$, $R^5$, $R^6$, $R^7$, $R^8$, $R_Y$, and $R_{N2}$ are as described herein.

In certain embodiments, the compound of formula (III) is compound 16:

16

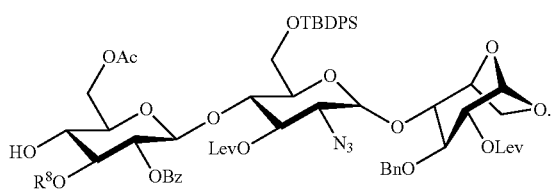

In certain embodiments, the compound of formula (IV) is compound 12:

12

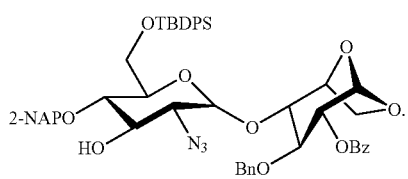

In certain embodiments, the compound of formula (V) is compound 13:

13

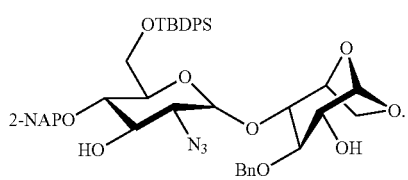

In certain embodiments, the compound of formula (VI) is compound 14:

14

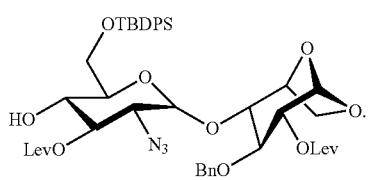

In certain embodiments, the compound of formula (VII) is compound 15:

15

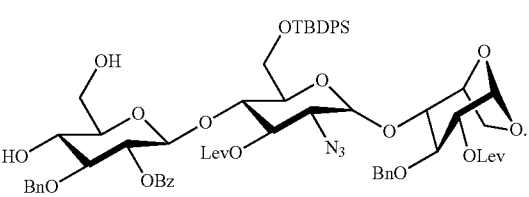

In certain embodiments, step (a) of Method A takes place in the presence of an electrophile. In certain embodiments, step (a) of Method A takes place in the presence of N-iodosuccinimide. In certain embodiments, step (a) of Method A takes place in the presence of acid. In certain embodiments, step (a) of Method A takes place in the presence of a catalytic amount of acid. In certain embodiments, step (a) of Method A takes place in the presence of triflic acid.

In some embodiments, step (a) of Method A takes place in a polar solvent. In certain embodiments, the solvent is a polar aprotic solvent. In certain embodiments, the solvent is a halogenated solvent. In certain embodiments, step (a) of Method A takes place in dichloromethane.

In some embodiments, the deprotection step (b) of Method A comprises treating the compound of formula (IV) with base. In certain embodiments, the base is an alkoxide. In certain embodiments, the base is a methoxide. In certain embodiments, the deprotection step (b) of Method A comprises treating the compound of formula (IV) with sodium methoxide in methanol. In certain embodiments, $R_Y$ in Method A is acetyl. In certain embodiments, $R^3$ in Method A is levulinyl.

In certain embodiments, step (c) of Method A comprises protecting the compound of formula (V) using 4-oxopentanoic acid (LevOH). In certain embodiments, step (c) of Method A comprises protecting the compound of formula (V) with EDC, DMAP, and 4-oxopentanoic acid.

In certain embodiments, $R^{12}$ of Method A is 2-napththylmethyl.

In certain embodiments, step (c) of Method A comprises deprotecting the compound of formula (V) with 2,3-dichloro-5,6-dicyano-1,4-benzoquinone (DDQ).

In certain embodiments, $R^4$ and $R^8$ of Method A are benzyl. In certain embodiments, $R_{N2}$ of Method A is $-N_3$.

In certain embodiments, step (d) of Method A takes place in the presence of an electrophile. In certain embodiments, step (d) of Method A takes place in the presence of N-iodosuccinimide. In certain embodiments, step (d) of Method A takes place in the presence of acid. In certain embodiments, step (d) of Method A takes place in the presence of a catalytic amount of acid. In certain embodiments, step (d) of Method A takes place in the presence of triflic acid.

In some embodiments, step (d) of Method A takes place in a polar solvent. In certain embodiments, the solvent is a polar aprotic solvent. In certain embodiments, the solvent is a halogenated solvent. In certain embodiments, step (d) of Method A takes place in dichloromethane.

In some embodiments, the protecting group of step (e) of Method A is an acetyl group.

In some embodiments, the present invention provides methods (Method B) of synthesizing a tetrasaccharide of formula (II):

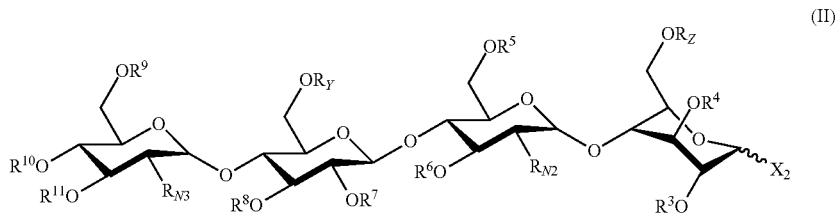

or a salt thereof;

the method comprising:

(a) reacting a trisaccharide of formula (III):

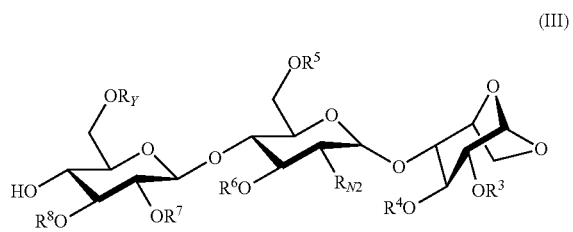

with a monosaccharide of formula A:

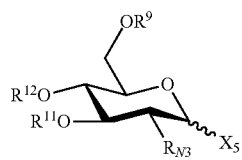

wherein $X_5$ is a leaving group;

in the presence of an activating agent under suitable conditions to form a compound of formula (VIIIa):

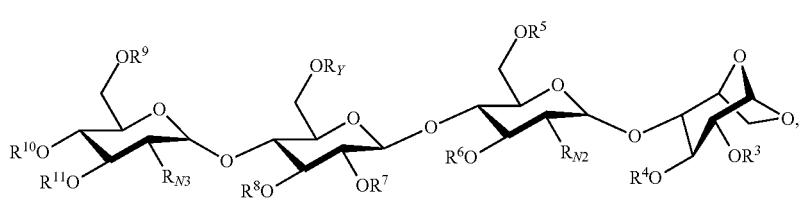

(b) ring-opening and protecting the compound of formula (VIIIa) under suitable conditions to form a compound of formula (VIII):

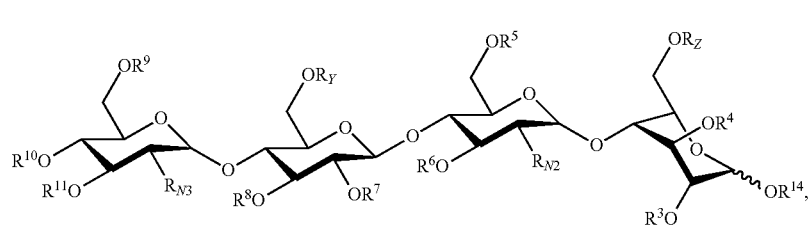

wherein $R^{14}$ is a protecting group; and (c) converting the —$OR^{14}$ group of the compound of formula (VIII) to a leaving group $X_2$ under suitable conditions to form a compound of formula (II);

wherein $X_2$, $X_5$, $R^3$, $R^4$, $R^5$, $R^6$, $R^7$, $R^8$, $R^9$, $R^{10}$, $R^{11}$, $R^{14}$, $R_Y$, $R_Z$, $R_{N2}$, and $R_{N3}$ are as described herein.

In certain embodiments, the compound of formula (II) is compound 18:

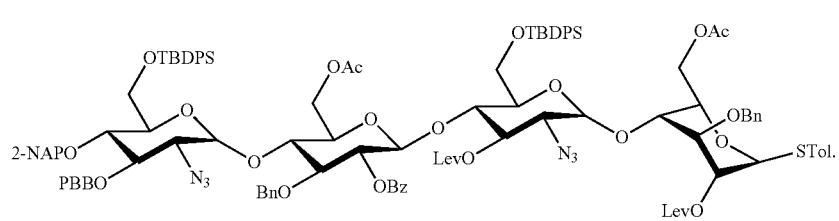

18

In certain embodiments, the compound of formula (III) is compound 16:

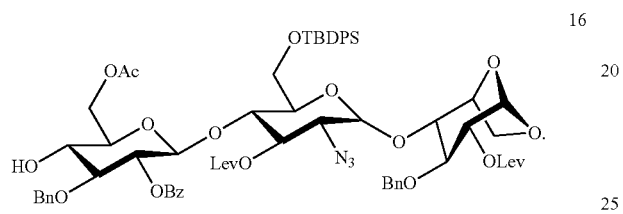

16

In certain embodiments, the compound of formula (VIII) is compound 17:

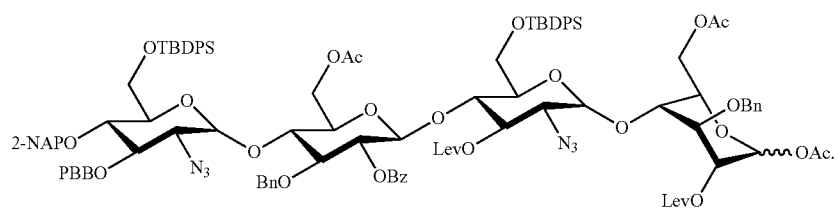

17

In certain embodiments, the compound of formula (III) used in Method B is prepared by Method A.

In certain embodiments, step (a) of Method B takes place in the presence of an electrophile. In certain embodiments, step (a) of Method B takes place in the presence of N-iodosuccinimide. In certain embodiments, step (a) of Method B takes place in the presence of acid. In certain embodiments, step (a) of Method B takes place in the presence of a catalytic amount of acid. In certain embodiments, step (a) of Method B takes place in the presence of triflic acid.

In some embodiments, step (a) of Method B takes place in a polar solvent. In certain embodiments, the solvent is a polar aprotic solvent. In certain embodiments, the solvent is a halogenated solvent. In certain embodiments, step (a) of Method B takes place in dichloromethane.

In certain embodiments, the $R^{14}$, $R_Y$, and $R_Z$ of Method B are acetyl. In certain embodiments, step (b) of Method B takes place in the presence of acetic anhydride. In certain embodiments, ring-opening is effected by a Lewis acid. In certain embodiments, the Lewis acid is trimethylsilyl trifluoromethanesulfonate (TMSOTf).

In some embodiments, $X_2$ of Method B is —S-tolyl. In certain embodiments, step (c) of Method B takes place in the presence of trimethyl(4-methylphenylthio)silane (TMSS-Tol). In certain embodiments, step (c) of Method B takes place in the presence of $ZnI_2$.

In certain embodiments, Method B further comprises reacting the tetrasaccharide of formula (II) with monosaccharide E:

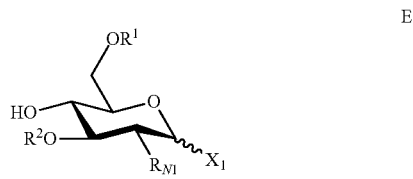

E wherein $X_1$, $R^1$, $R^2$, and $R_{N1}$ are as described herein; under suitable conditions to form a pentasaccharide of formula (I) as described herein.

In some embodiments, the present invention provides methods (Method C) of synthesizing a tetrasaccharide of Formula (II):

(II)

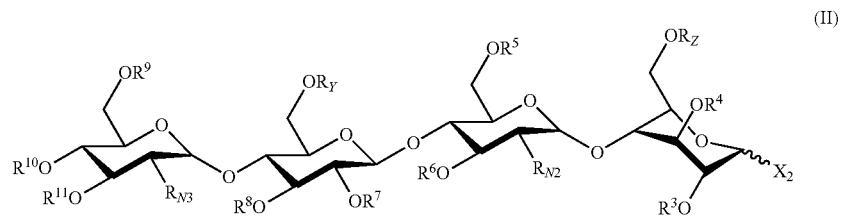

or a salt thereof;

the method comprising:

(a) reacting a disaccharide of formula (VI):

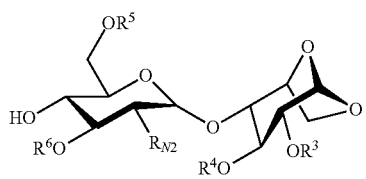

with a disaccharide of formula F:

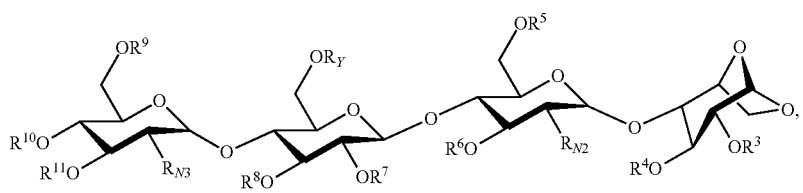

wherein $X_6$ is a leaving group;

in the presence of an activating agent under suitable conditions to form a compound of formula (VIIIa):

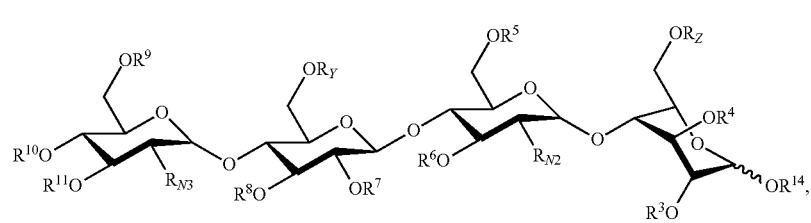

(b) ring-opening and protecting the compound of formula (VIIIa) under suitable conditions to form a compound of formula (VIII):

(VIII)

wherein $R^{14}$ is an oxygen protecting group; and (c) converting the $-OR^{14}$ group of the compound of formula (VIII) to a leaving group $X_2$ under suitable conditions to form a compound of formula (II);

wherein $X_2$, $R^3$, $R^4$, $R^5$, $R^6$, $R^7$, $R^8$, $R^9$, $R^{10}$, $R^{11}$, $R_Y$, $R_Z$, $R_{N2}$, and $R_{N3}$ are as described herein.

In certain embodiments, the compound of formula (II) is compound 18:

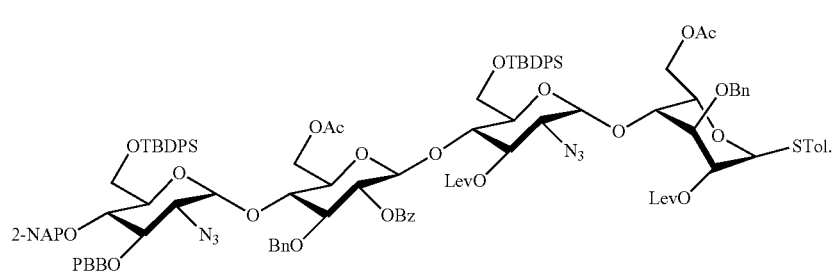

18

In certain embodiments, the compound of formula (VI) is compound 14:

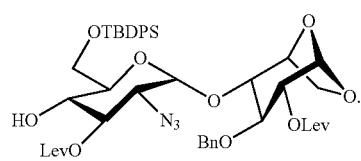

14

In certain embodiments, the compound of formula (VIII) is compound 17:

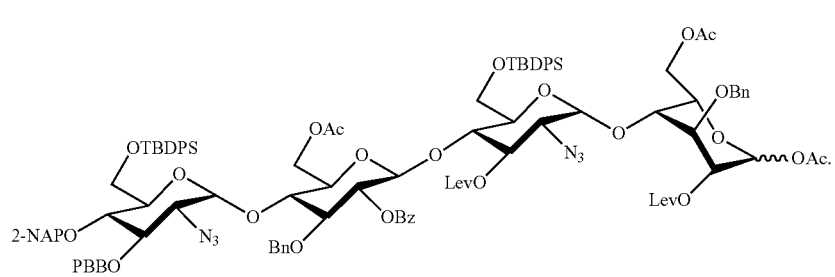

17

In certain embodiments, $R^{14}$, $R_Y$, and $R_Z$ of Method C are acetyl.

In certain embodiments, the compound of formula F is compound 28:

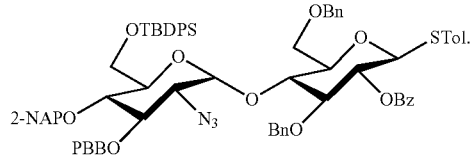

28

In certain embodiments, the present invention provides methods of synthesizing a tetrasaccharide of formula (VIIIa):

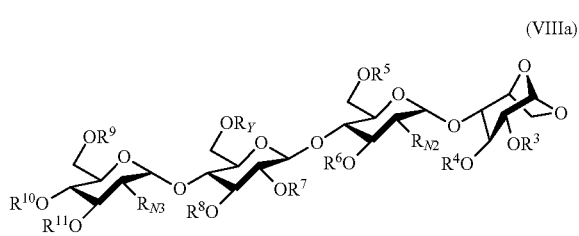

(VIIIa)

or a salt thereof;

wherein:

$R^{11}$ is optionally substituted arylalkyl;

$R_{N2}$ and $R_{N3}$ are independently —$N_3$ or —$N(R^W)_2$, wherein each $R^W$ is independently hydrogen or a nitrogen protecting group;

$R^3$ and $R^6$ are independently —$C(O)R^D$, wherein each occurrence of $R^D$ is independently optionally substituted alkyl or optionally substituted aryl;

$R^5$ and $R^9$ are independently selected from the group consisting of optionally substituted arylalkyl and —$Si(R^B)_3$, wherein each $R^B$ is independently alkyl or aryl;

$R^{10}$ is optionally substituted arylalkyl;

$R_Y$ is independently hydrogen or an oxygen protecting group; or $R_Z$ and $X_2$ are taken together with their intervening atoms to form a five-membered ring;

$R^7$ is selected from the group consisting of —$Si(R^B)_3$, optionally substituted arylalkyl, and —$C(O)R^C$, wherein $R^C$ is optionally substituted alkyl, optionally substituted aryl, or optionally substituted arylalkyl; and $R^4$ and $R^8$ are independently optionally substituted arylalkyl; the method comprising:

reacting a disaccharide of formula (VI):

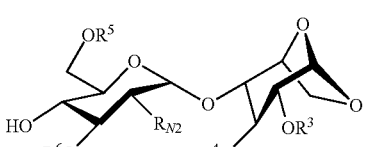

(VI)

with a disaccharide of formula F:

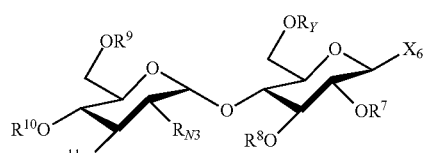

F wherein $X_6$ is a leaving group;

in the presence of an activating agent under suitable conditions to form a compound of formula (VIIIa).

In certain embodiments, the compound of formula (VIIIa) is

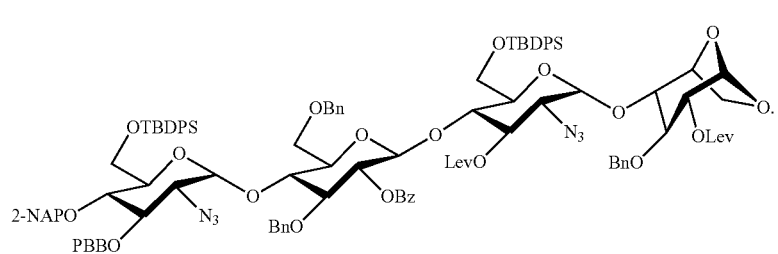

In certain embodiments, step (a) of Method C takes place in the presence of an electrophile. In certain embodiments, step (a) of Method C takes place in the presence of N-iodosuccinimide. In certain embodiments, step (a) of Method C takes place in the presence of acid. In certain embodiments, step (a) of Method C takes place in the presence of a catalytic amount of acid. In certain embodiments, step (a) of Method C takes place in the presence of triflic acid.

In some embodiments, step (a) of Method C takes place in a polar solvent. In certain embodiments, the solvent is a polar aprotic solvent. In certain embodiments, the solvent is a halogenated solvent. In certain embodiments, step (a) of Method C takes place in dichloromethane.

In certain embodiments, the $R^{14}$, $R_Y$, and $R_Z$ of Method C are acetyl. In certain embodiments, step (b) of Method C takes place in the presence of acetic anhydride. In certain embodiments, ring-opening is effected by a Lewis acid. In certain embodiments, the Lewis acid is trimethylsilyl trifluoromethanesulfonate (TMSOTf).

In some embodiments, $X_2$ of Method C is S-tolyl. In certain embodiments, step (c) of Method C takes place in the presence of trimethyl(4-methylphenylthio)silane (TMSS-Tol). In certain embodiments, step (c) of Method C takes place in the presence of $ZnI_2$.

In certain embodiments, Method C further comprises reacting the tetrasaccharide of formula (II) with monosaccharide E:

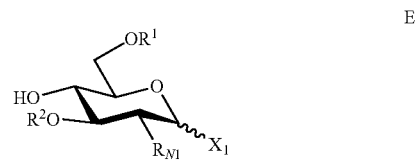

wherein $X_1$, $R^1$, $R^2$, and $R_{N1}$ are as described herein; under suitable conditions to form a pentasaccharide of formula (I) as described herein.

In some embodiments, the present invention provides methods (Method D) for synthesizing a pentasaccharide of formula (I):

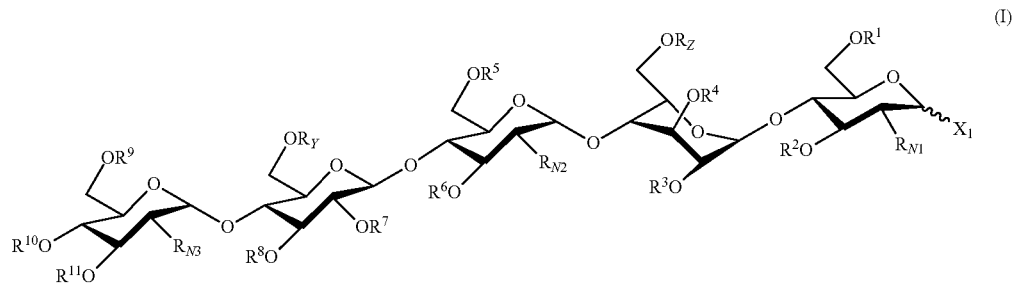

or a salt thereof;
the method comprising:
reacting a tetrasaccharide of formula (II):

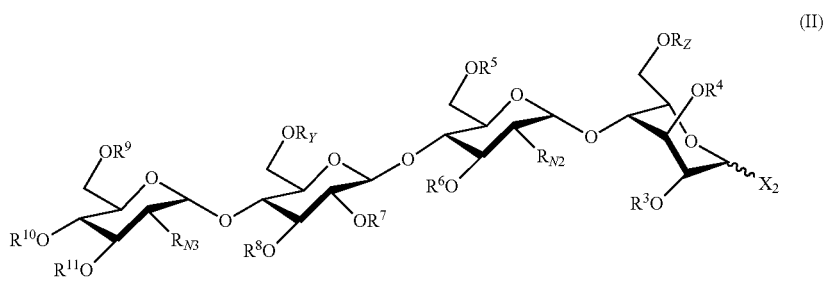

with monosaccharide E:

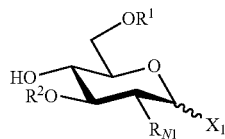

under suitable conditions to form a pentasaccharide of formula (I);

wherein $X_1$, $X_2$, $R^1$, $R^2$, $R^3$, $R^4$, $R^5$, $R^6$, $R^7$, $R^8$, $R^9$, $R^{10}$, $R^{11}$, $R_Y$, $R_Z$, $R_{N1}$, $R_{N2}$, and $R_{N3}$ are as described herein.

In some embodiments, Method D described above further comprises a deprotection step.

In certain embodiments, the reaction between the tetrasaccharide of formula (II) and monosaccharide E of Method D takes place in the presence of an electrophile. In certain embodiments, the electrophile is N-iodosuccinimide. In certain embodiments, the reaction between the tetrasaccharide of formula (II) and monosaccharide E of Method D takes place in the presence of an acid. In certain embodiments, the reaction between the tetrasaccharide of formula (II) and monosaccharide E of Method D takes place in the presence of a catalytic amount of acid. In certain embodiments, the reaction between the tetrasaccharide of formula (II) and monosaccharide E of Method D takes place in the presence of triflic acid.

In some embodiments, the reaction between the tetrasaccharide of formula (II) and monosaccharide E of Method D takes place in a polar solvent. In certain embodiments, the solvent is a polar aprotic solvent. In certain embodiments, the solvent is a halogenated solvent. In certain embodiments, the halogenated solvent is dichloromethane.

In another aspect, the present disclosure provides a method (Method E) of synthesizing fondaparinux:

or a salt thereof;
the method comprising:
  (a) deprotecting a pentasaccharide of formula (I'):

(I')

wherein:
  $X_1$ is alpha-methoxy;
  $R^2$ and $R^{11}$ are independently optionally substituted arylalkyl;
  $R_{N1}$, $R_{N2}$, and $R_{N3}$ are independently —$N_3$ or —$N(R^W)_2$, wherein each $R^W$ is independently hydrogen or a nitrogen protecting group;
  $R^3$ and $R^6$ are independently —$C(O)R^D$, wherein each occurrence of $R^D$ is independently optionally substituted alkyl or optionally substituted aryl;
  $R^1$, $R^5$, and $R^9$ are independently selected from the group consisting of optionally substituted arylalkyl and —$Si(R^B)_3$, wherein each $R^B$ is independently alkyl or aryl;
  $R^{10}$ is optionally substituted arylalkyl;
  $R_Y$ and $R_Z$ are independently hydrogen or an oxygen protecting group;
  $R^7$ is selected from the group consisting of $Si(R^B)_3$, optionally substituted arylalkyl, and —$C(O)R^C$, wherein $R^C$ is optionally substituted alkyl, optionally substituted aryl, or optionally substituted arylalkyl; and
  $R^4$ and $R^8$ are independently optionally substituted arylalkyl;

under suitable conditions to form a compound of formula (IX):

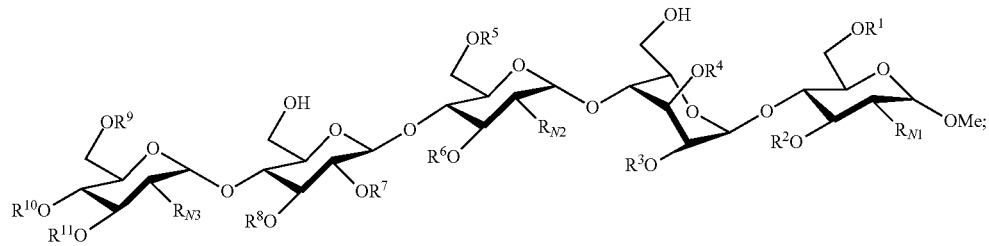

(IX)

(b) oxidizing, deprotecting, and esterifying the compound of formula (IX) under suitable conditions to form a compound of formula (X):

(X)

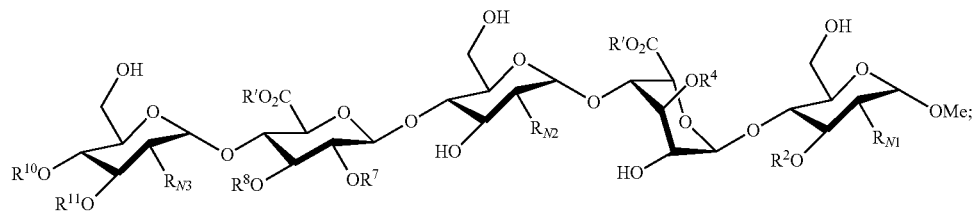

wherein R' is $C_{1-6}$ alkyl or optionally substituted benzyl;

(c) sulfonating the compound of formula (X) under suitable conditions to form a compound of formula (XI):

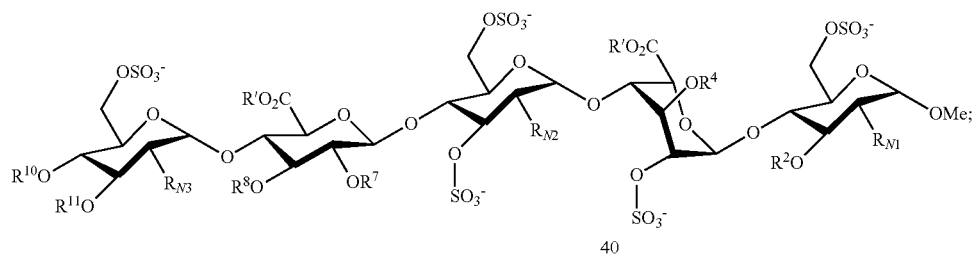

(XI)

(d) converting the compound of formula (XI) to a compound of formula (XII) under suitable conditions:

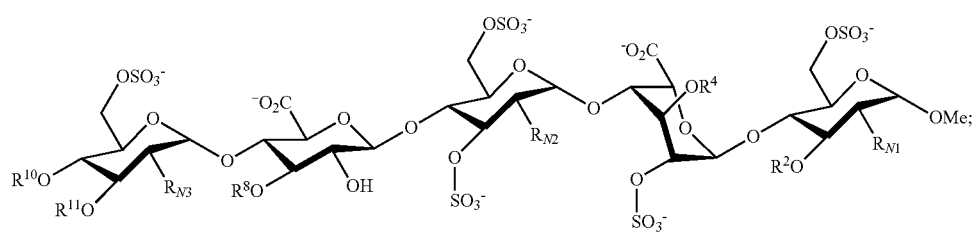

(XII)

(e) deprotecting the compound of formula (XII) under suitable conditions to form a compound of formula (XIII):

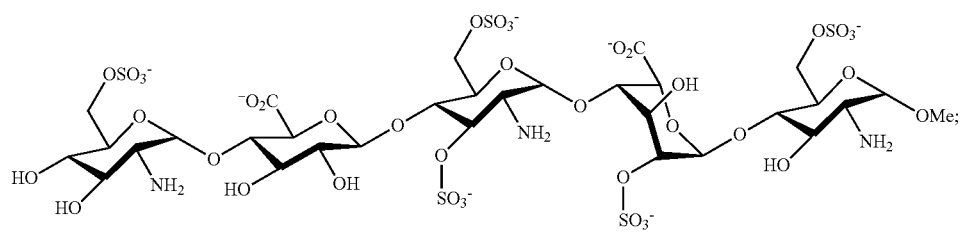

(XIII)

and (f) sulfonating the compound of formula (XIII) under suitable conditions to form fondaparinux 25.

$X_1$, R', $R^1$, $R^2$, $R^3$, $R^4$, $R^5$, $R^6$, $R^7$, $R^8$, $R^9$, $R^{10}$, $R^{11}$, $R_Y$, $R_Z$, $R_{N1}$, $R_{N2}$, and $R_{N3}$ are further described in embodiments herein.

In certain embodiments, $R_{N1}$, $R_{N2}$, and $R_{N3}$ of formula (I') of Method E are independently selected from the group consisting of —$N_3$, —NH(Cbz), —NHC(O)CH$_3$, and —N(C(O)CH$_3$)$_2$.

In certain embodiments, the pentasaccharide of formula (I') is compound 19:

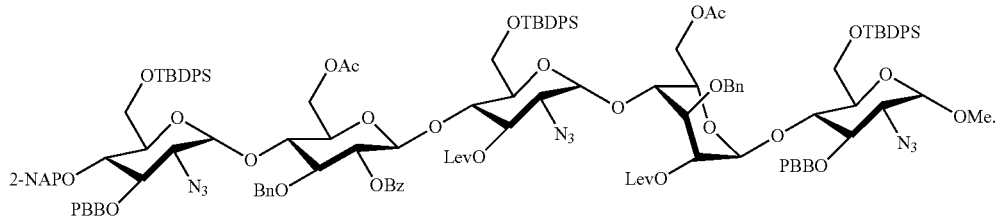

19

In certain embodiments, the compound of formula (IX) is compound 20:

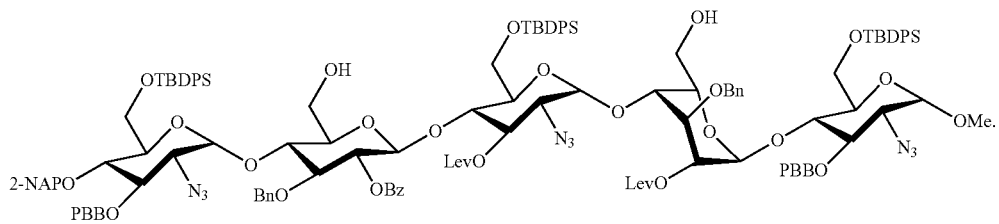

20

In certain embodiments, the compound of formula (X) is compound 21:

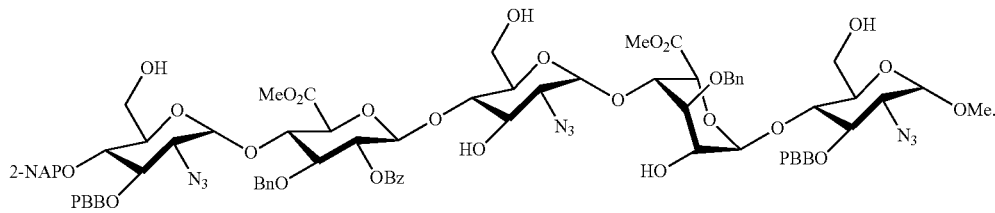

21

In certain embodiments, the compound of formula (XI) is compound 22:

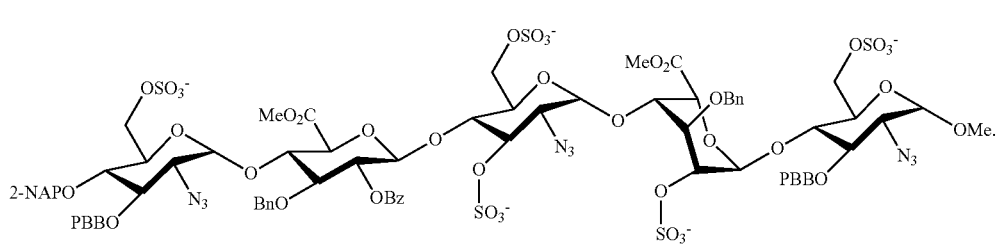

22

In certain embodiments, the compound of formula (XII) is compound 23:

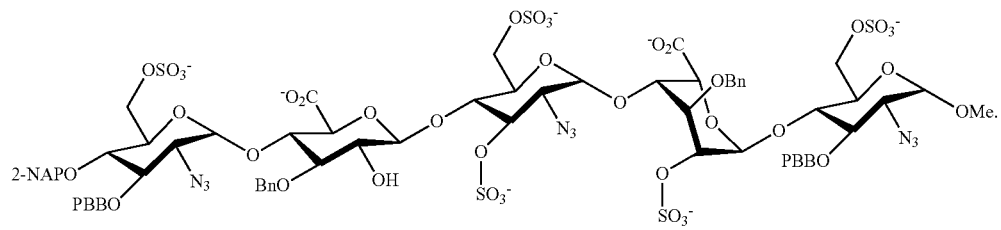

23

In certain embodiments, the compound of formula (I') is prepared by Method B, C, or D.

In some embodiments, the deprotection step (a) of Method E comprises treating the compound of formula (I') with base. In certain embodiments, the base is an alkoxide. In certain embodiments, the base is a methoxide. In certain embodiments, the deprotection step (a) of Method E comprises treating the compound of formula (I') with Mg(OMe)$_2$. In certain embodiments, R$_{Y'}$ in Method A is acetyl.

In certain embodiments, the oxidizing of step (b) of Method E comprises using 2,2,6,6-tetramethylpiperidine-1-oxyl (TEMPO). In certain embodiments, the oxidizing of step (b) of Method E comprises using bisacetoxyiodobenzene (BAIB). In certain embodiments, the oxidizing of step (b) of Method E comprises using 2,2,6,6-tetramethylpiperidine-1-oxyl (TEMPO)/bisacetoxyiodobenzene (BAIB).

In certain embodiments, the esterifying of step (b) of Method E comprises using diazomethane. In certain embodiments, the esterifying of step (b) of Method E comprises using hydrazine. In certain embodiments, the esterifying of step (b) of Method E comprises transesterification with an alcohol. In certain embodiments, the esterifying of step (b) of Method E comprises using t-butylene. In certain embodiments, the esterifying of step (b) of Method E comprises using an alkyl halide. In certain embodiments, the deprotection of step (b) of Method E comprises using a fluoride reagent. In certain embodiments, the deprotection of step (b) of Method E comprises using HF.

In certain embodiments, the sulfonating step (c) of Method E comprises using SO$_3$-pyridine complex. In certain embodiments, the sulfonating step (c) of Method E comprises using SO$_3$ and triethylamine. In certain embodiments, the sulfonating step (f) of Method E comprises using SO$_3$-pyridine complex. In certain embodiments, the sulfonating step (e) of Method E comprises using SO$_3$ and triethylamine. In certain embodiments, the sulfonating step (c) of Method E comprises using SO$_3$ and triethylamine in DMF. In certain embodiments, the sulfonating step (f) of Method E comprises using SO$_3$-pyridine complex in aqueous sodium hydroxide.

In certain embodiments, step (d) of Method E comprises using a base. In certain embodiments, the base is hydroxide. In certain embodiments, the base is sodium hydroxide. In certain embodiments, the base is lithium hydroxide. In certain embodiments, step (d) of Method E employs a peroxide in addition to a base. In certain embodiments, the peroxide is hydrogen peroxide.

In certain embodiments, the deprotecting step (e) of Method E comprises using PdOH/carbon and hydrogen gas. In certain embodiments, the deprotecting step (e) of Method E takes place in a buffer. In certain embodiments, the buffer is a phosphate buffer.

In certain embodiments, the present invention provides a method of synthesizing fondaparinux comprising Methods A, B, D, and E. In certain embodiments, the present invention provides a method of synthesizing fondaparinux comprising Methods C, D, and E.

EXAMPLES

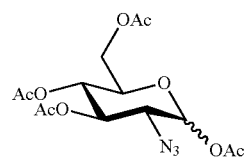

2

3,4,6-tri-O-acetyl-2-azido-2-deoxy-D-glucopyranosyl acetate (2)

Trifluoromethanesulfonic anhydride (0.94 mL, 5.57 mmol) was slowly added dropwise from an addition funnel to a solution of sodium azide (1.80 g, 27.8 mmol) in a mixture of water (4.7 mL) and dichloromethane (7.6 mL) at 0° C. After stirring at the same temperature for 2 h, the organic layer was separated, and the aqueous layer was extracted with dichloromethane. The combined organic layers were neutralized with saturated NaHCO3(aq). The generated trifluoromethanesulfonicazide (TfN$_3$) was directly used without further purification for the ensuing reaction. Sodium carbonate (0.59 g, 5.57 mmol) was added to a solution of D-glucosamine hydrochloride 1 (1.00 g, 4.60 mmol) in water (10 mL) until the pH value was around 10-11. After immersing this mixture in an ice-bath, CuSO4.5H2O (12.0 mg, 0.05 mmol) and the TfN3 solution in dichloromethane were added sequentially. MeOH (10 mL) was added to the mixture until the phase became homogeneous. The ice-bath was then removed and the reaction was kept stirring at room temperature for 2 d. After that, acetic anhydride (4.0 mL), DMAP (0.01 g, 0.09 mmol) were added and stirred for 1 d. The mixture was filtered through celite, and the filtrate was concentrated in vacuo. The residue was purified by flash column chromatography (EtOAc/Hex=1/1) to afford the azido compound 2.

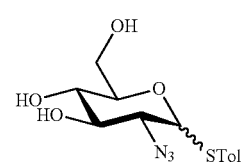

3 p-Methylphenyl 2-azido-2-deoxy-1-thio-D-glucopyranoside (3)

To a solution of 2 (1.00 g, 2.68 mmol) and p-thiocresol (0.41 g, 3.30 mmol) in BF$_3$/OEt$_2$ (5.0 mL) was stirred for 8 h at room temperature, and the reaction was added with MeOH (5.0 mL), and refluxed for 16 h. Et$_3$N was added to quench the reaction, and was evaporated at reduced pressure. The residue was purified by flash column chromatography (MeOH/CH$_3$Cl=1/9) to afford compound 3 in 78% yield.

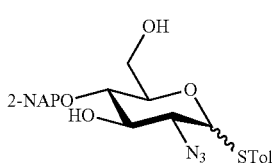

4 p-Methylphenyl 2-azido-2-deoxy-4-O-(2-naphthylmethyl)-1-thio-D-glucopyranoside (4)

TMSOTf (58.0 μL, 0.32 mmol) was added at room temperature under nitrogen to a suspension of 3 (1.00 g, 3.20 mmol) and HMDS (1.14 mL, 5.12 mmol) in CH$_2$Cl$_2$ (10 mL). After the system had been stirred for 1 h, CH$_2$Cl$_2$ (10 mL), 4 Å molecular sieves (1.00 g) and 2-NAPCHO (0.56 g, 3.36 mmol) were added and stirred for 1 h. The mixture was then cooled to 0° C. and TMSOTf (0.12 mL, 0.64 mmol) was added. After the system had been stirred for 2 h, BH$_3$/THF (17.0 mL, 16.0 mmol), and TMSOTf (0.3 mL, 1.6 mmol) were added. After the reaction had been stirred at 0° C. for another 8 h, TBAF (3.20 mL) was added. The mixture was stirred at room temperature for 16 h and filtered through a pad of celite. The filtrate was washed with saturated NaHCO$_{3(aq)}$, extracted with ethyl acetate. The organic layer was dried over anhydrous MgSO$_4$, filtered, and concentrated in vacuo. The residue was purified by flash column chromatography (EtOAc/Hex=1/3) to afford compound 4 (1.27 g, 88%). $^1$H NMR (600 MHz, CDCl$_3$) δ 7.84-7.75 (m, 9H, Ar—H), 7.48-7.45 (m, 5.6H, Ar—H), 7.42 (t, J=6.3 Hz, 3.5H, Ar—H), 7.35 (d, J=7.9 Hz, 3H, Ar—H), 7.12 (dd, 4.6H, J=11.9, 8.0 Hz, Ar—H), 5.43 (d, J=5.5 Hz, 1.2H, H-1), 4.95 (d, J=11.5 Hz, 1.2H, CH$_2$Ph), 4.91 (d, J=11.5 Hz, 1.2H, CH$_2$Ph), 4.89 (d, J=8.5 Hz, 1H, CH$_2$Ph), 4.84 (d, J=8.5 Hz, 1H, CH$_2$Ph), 4.38 (d, J=9.7 Hz, 1H, H-1), 4.25 (d, J=9.4 Hz, 1.2H, H-5), 3.96 (t, J=9.6 Hz, 1.2H, H-3), 3.91 (d, J=10.4 Hz, 1H, H-6a), 3.83-3.80 (m, 2.4H, H-6ab), 3.76-3.71 (m, 2.2H, H-2, H-6b), 3.60 (t, J=9.7 Hz, 1H, H-3), 3.56 (t, J=9.4 Hz, 1.2H, H-4), 3.44 (t, J=9.7 Hz, 1H, H-4), 3.33-3.31 (m, 1H, H-5), 3.21 (t, J=9.7 Hz, 1H, H-2), 2.93 (brs, 2H, OH), 2.33 (s, 3H), 2.31 (s, 3.6H).

immersed in an ice-water bath. TBDPSCl (2.9 mL, 12.0 mmol) was added to the solution, the ice-water bath was removed, and the mixture was kept stirring for 1 day. The reaction was quenched by adding MeOH and the solvents were evaporated under reduced pressure. The reaction was extracted with ethyl acetate and water. The combined organic layer was dried over MgSO$_4$, filtered and concentrated in vacuo to give a residue, which was further purified by flash column chromatography (EtOAc/Hex=1/7) to afford compound C (6.88 g, 90%).

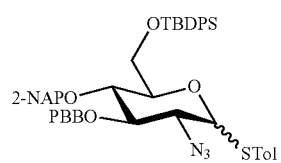

A p-Methylphenyl 2-azido-3-O-(p-bromobenzyl)-6-O-tert-butyldiphenylsilyl-2-deoxy-4-O-(2-naphthylmethyl)-1-thio-D-glucopyranoside (A)

To a solution of C (10.00 g, 14.5 mmol) in THF (100.0 mL) was consecutively added with parabromobenzylbromide (4.75 g, 15.23 mmol) and NaH (0.56 g, 17.4 mmol) at 0° C. under nitrogen. After stirring for 8 h at room tempracture, the reaction was quenched with MeOH, and the solvent was evaporated at reduced pressure. The mixture was dissolved in EtOAc, and the solution was sequentially washed with water, and brine. The organic layer was dried over anhydrous MgSO$_4$, filtered, and concentrated in vacuo. The mixture was further purified by flash column chromatography (EtOAc/Hex=1/9) to afford compound A (11.8 g, 90%). $^1$H NMR (400 MHz, CDCl$_3$) δ 7.94-7.89 (m, 5.5H, Ar—H), 7.86-7.76 (m, 18.0H, Ar—H), 7.69-7.65 (m, 3.6H, Ar—H), 7.59-7.55 (m, 6.2H, Ar—H), 7.54-7.44 (m, 19.3H, Ar—H), 7.42-7.34 (m, 12.3H, Ar—H), 7.31-7.26 (m, 4.8H, Ar—H), 7.14-7.12 (m, 5.4H, Ar—H), 5.68 (d, J=5.3 Hz, 1.6H, αH-1), 5.10 (d, J=11.1 Hz, 1.7H, ArCH$_2$), 5.05-5.00 (m, 2.7H, ArCH$_2$), 4.98 (s, 1.0H, ArCH$_2$), 4.95 (s, 3.3H, ArCH$_2$), 4.89 (s, 2.0H, ArCH$_2$), 4.48 (d, J=10.1 Hz, 1.0H, βH-1), 4.43 (d, J=9.4, 1.5H, αH-5), 4.18-4.14 (m, 2.7H, αH-6a, βH-6a), 4.10-3.91 (m, 8.7H, αH-2, αH-6b, αH-3, αH-4, βH-2, βH-6b), 3.65-3.60 (m, 1.4H, βH-3), 3.50-3.45 (m, 2.1H, βH-4, βH-5), 2.40 (s, 7.6H, CH$_3$), 1.22 (s, 9.9H, t-Bu), 1.18 (s, 13.7H, t-Bu).

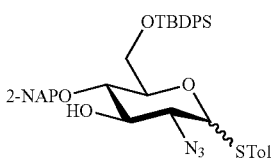

C p-Methylphenyl 2-azido-6-O-tert-butyldiphenylsilyl-2-deoxy-4-O-(2-naphthylmethyl)-1-thio-D-glucopyranoside (C)

Compound 4 (5.00 g, 10.9 mmol), Et$_3$N (4.6 mL, 21.8 mmol) and DMAP (0.13 g, 1.1 mmol) were dissolved in CH$_2$Cl$_2$ (50.0 mL) under nitrogen and the reaction flask was

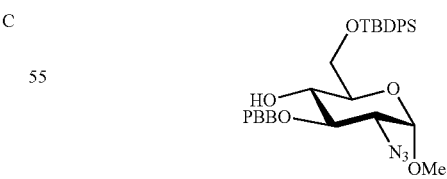

E

Methyl 2-azido-3-O-(p-bromobenzoyl)-6-O-tert-butyldiphenylsilyl-2-deoxy-α-D-glucopyranoside (E)

A mixture of the thioglycoside A (2.00 g, 2.33 mmol) and MeOH (0.13 mL, 2.8 mmol) in dry Et$_2$O (20.0 mL) was added to a reaction flask containing freshly dried 3 Å molecular sieves under nitrogen. The mixture was stirred at room temperature for 1 h, and the solution was cooled to −60° C. N-Iodosuccinimide (NIS, 0.64 g, 2.8 mmol) and trifluoromethanesulfonic acid (100.0 μL, 1.17 mmol) were added to the reaction flask, and the mixture was gradually warmed up to −40° C. The resulting solution was kept stirring for 3 h, and DDQ (1.61 g, 11.65 mmol), CH$_3$CN (20.0 mL) were added to the reaction. The mixture was stirred for 2 days and the whole mixture was filtered through Celite followed by washing with CH$_2$Cl$_2$, and the filtrate was sequentially washed with 10% Na$_2$S$_2$O$_{3(aq)}$ and brine. The organic layer was dried over anhydrous MgSO$_4$. The residue was filtered and concentrated in vacuo to give the crude product which was purified by flash column chromatography (EtOAc/Hex=1/8) to give the compound E (0.83 g, 57%). $^1$H NMR (600 MHz, CDCl$_3$) δ 7.70-7.65 (m, 6H, Ar—H), 7.48-7.35 (m, 11H, Ar—H), 7.27 (d, J=8.2 Hz, 1H, Ar—H), 4.82 (d, J=11.4 Hz, 1H, ArCH$_2$), 4.79 (d, J=11.4 Hz, 1H, ArCH$_2$), 4.72 (d, J=3.2 Hz, 1H, H-1), 3.86-3.85 (m, 2H, H-6a, H-6b), 3.79 (t, J=9.3 Hz, 1H, H-3), 3.71 (t, J=9.3 Hz, 1H, H-4), 3.64-3.62 (m, 1H, H-5), 3.34 (s, 3H, CH$_3$), 3.31 (dd, J=9.3, 3.2 Hz, 1H, H-2), 2.62 (s, 1H, OH), 1.05 (s, 9H, t-Bu).

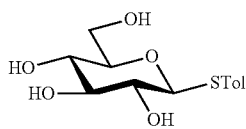

6 p-Methylphenyl 1-thio-β-D-glucopyranoside (6)

To a solution of 5 (1.00 g, 2.56 mmol) and p-thiocresol (0.41 g, 3.30 mmol) in BF$_3$/OEt$_2$ (5.0 mL) was stirred for 8 h at room temperature, and the reaction was added with MeOH (5.0 mL), and refluxed for 16 h. Et$_3$N was added to quench the reaction, and was evaporated at reduced pressure. The residue was purified by flash column chromatography (MeOH/CH$_3$Cl=1/9) to afford compound 6 in 72% yield.

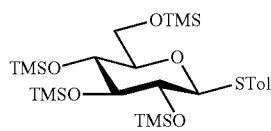

6a p-Methylphenyl 2,3,4,6-tri-O-methylsilyl-1-thio-β-D-glucopyranoside (6a)

Compound 6 (29.0 g, 101 mmol) was dissolved in CH$_2$Cl$_2$ (300 mL) under N$_2$ atmosphere, the reaction flask was immersed in an ice bath, Et$_3$N (140 mL, 1.01 mol) and TMSCl (64.7 mL, 506 mmol) were sequentially added to the solution, and the mixture was stirred at room temperature for 16 h. The reaction was quenched with water, and the crude target material was extracted with ethyl acetate. The combined organic layer was dried over MgSO$_4$, filtered and concentrated in vacuo to give a residue, which was further recrystallized via vapor diffusion method to provide 6a (56.00 g, 97%) as colorless crystals.

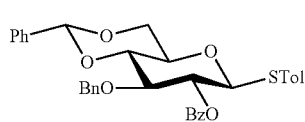

B p-Methylphenyl 2-O-benzoyl-3-O-benzyl-4,6-O-benzylidene-1-thio-β-D-glucopyranoside (B)

TMSOTf (47.0 μL, 0.26 mmol) was added at 0° C. under nitrogen to a solution of 6a (1.00 g, 1.74 mmol), 4 Å molecular sieves (1.00 g) and benzaldehyde (0.18 mL, 1.77 mmol) in CH$_2$Cl$_2$ (10 mL). After the system had been stirred for 2 h, triethylsilane (0.30 mL, 1.91 mmol), benzaldehyde (0.18 mL, 1.77 mmol) and TMSOTf (30.0 μL, 0.17 mmol) were added. After the reaction had been stirred for another 4 h, benzoic anhydride (1.00 mL, 8.70 mmol) and TMSOTf (0.12 mL, 0.7 mmol) were successively added at 0° C. The mixture was stirred at room temperature for 16 h and filtered through a pad of celite. The filtrate was washed with saturated NaHCO$_{3(aq)}$, extracted with ethyl acetate. The organic layer was dried over anhydrous MgSO4, filtered, and concentrated in vacuo. The residue was purified by flash column chromatography (EtOAc/Hex=1/8) to afford compound B (0.62 g, 63%). $^1$H NMR (400 MHz, CDCl$_3$) δ 8.05 (dd, J=8.4, 1.3 Hz, 2H, Bz-H), 7.63 (tt, J=7.4, 1.3 Hz, 1H, Ar—H), 7.53-7.47 (m, 4H, Ar—H), 7.44-7.35 (m, 5H, Ar—H), 7.16-7.06 (m, 7H, Ar—H), 5.62 (s, 1H, PhCH), 5.29 (dd, J=10.0, 8.6 Hz, 1H, H-2), 4.83 (d, J=12.0 Hz, 1H, CH$_2$Ph), 4.81 (d, J=10.0 Hz, 1H, H-1), 4.68 (d, J=12.0 Hz, 1H, CH$_2$Ph), 4.44 (dd, J=10.3, 5.0 Hz, 1H, H-6a), 3.90 (dd, J=9.2, 8.6 Hz, 1H, H-3), 3.86 (t, J=10.3 Hz, 1H, H-6b), 3.82 (t, J=9.2 Hz, 1H, H-4), 3.57 (ddd, J=10.3, 9.2, 5.0 Hz, 1H, H-5), 2.34 (s, 3H, CH$_3$).

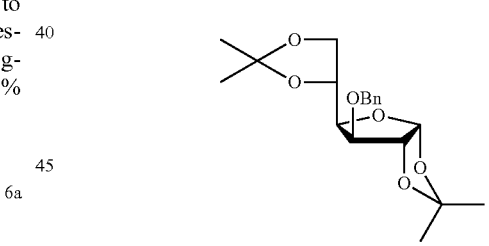

8

3-O-Benzyl 1,2:5,6,-di-O-isopropylidene-α-D-glucofuranose (8)

To a solution of 7 (1,2:5,6,-di-O-isopropylidene-α-D-glucofuranose, commercially available, 50.0 g, 192 mmol) in THF (500 mL) was consecutively added benzyl bromide (39.4 g, 230 mmol) and NaH (11.5 g, 288 mmol) at 0° C. under nitrogen. After stirring for 8 h at room temprature, the reaction was quenched with MeOH, and the solvent was evaporated at reduced pressure. The mixture was dissolved in EtOAc, and the solution was sequentially washed with water, and brine. The organic layer was dried over anhydrous MgSO$_4$, filtered, and concentrated in vacuo to afford compound 8. $^1$H NMR (400 MHz, CDCl$_3$) δ 7.36-7.25 (m, 5H, Ar—H), 5.88 (d, J=3.7 Hz, 1H, H-1), 4.66, 4.62 (ABq, J=11.8 Hz, 2H, CH$_2$Ph), 4.57 (d, 1H, J=3.7 Hz, H-2), 4.35 (m, 1H, H-5), 4.13 (dd, J=7.8, 3.0 Hz, 1H, H-4), 4.10 (dd, J=8.6, 6.0 Hz, 1H, H-6a), 4.01 (d, J=3.0 Hz, 1H, H-3), 3.99 (dd, J=8.5, 6.0 Hz, 1H, H-6b), 1.48 (s, 3H, CH$_3$), 1.41 (s, 3H, CH$_3$), 1.36 (s, 3H, CH$_3$), 1.29 (s, 3H, CH$_3$).

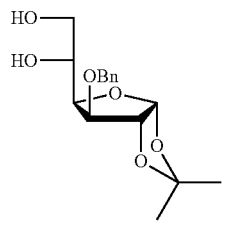

9

3-O-Benzyl 1,2-O-isopropylidene-α-D-glucofuranose (9)

To a solution of 8 in 64% AcOH (250 mL) was stirred for 16 h at room temperature and the reaction was quenched with saturated NaHCO$_{3(aq)}$. The mixture was dissolved in EtOAc, and the solution was sequentially washed with water, and brine. The organic layer was dried over anhydrous MgSO$_4$, filtered, and concentrated in vacuo. The residue was purified by flash column chromatography (EtOAc/Hex=1/5) to afford compound 9. $^1$H-NMR (400 MHz, CDCl$_3$) δ 7.33-7.21 (m, 1H, Ar—H), 5.87 (d, J=3.8 Hz, 1H, H-1), 4.64, 4.56 (ABq, J=11.7 Hz, 2H, CH$_2$Ph), 4.56 (d, J=3.8 Hz, 1H, H-2), 4.12-4.04 (m, 2H, H-3, H-4), 4.02-3.94 (m, 1H, H-5), 3.76 (dd, 1H, J=11.6, 2.9 Hz, H-6a), 3.64 (dd, 1H, J=11.6, 5.5 Hz, H-6b), 3.34 (brs, 2H, OH-5, OH-6), 1.44 (s, 3H, CH$_3$), 1.26 (s, 3H, CH$_3$).

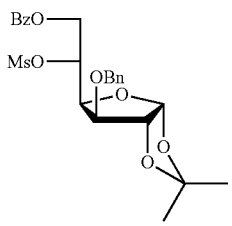

10

6-O-Benzoyl-3-O-benzyl-5-O-methylsulfonyl-1,2-O-isopropylidene-α-D-glucofuranose (10)

Compound 9 was dissolved in CH$_2$Cl$_2$ (500 mL) under N$_2$ atmosphere, the reaction flask was immersed in an ice bath, Et$_3$N (90.0 mL, 644 mmol) and benzoyl chloride (14.2 mL, 122 mmol) were sequentially added to the solution, and the mixture was stirred at the same temperature for 2 h. Methyl chloride (9.48 mL, 122 mmol) was added to the solution, the ice bath was removed, and then, the mixture was stirred at room temperature for 16 h. The reaction was quenched with water, and the crude target material was extracted with ethyl acetate. The combined organic layer was sequentially washed with 1 N HCl$_{(aq)}$, saturated NaHCO$_{3(aq)}$ and brine. The organic phase was dried over MgSO$_4$, filtered and concentrated in vacuo to get a residue, which was purified by flash column chromatography on silica gel (EtOAc/Hex=1/3) to provide 10 (70.9 g, 75% in three steps) as a white solid. $^1$H NMR (400 MHz, CDCl$_3$) δ 8.06 (dd, J=7.5, 1.5 Hz, 2H, Bz-H), 7.56 (t, J=7.5 Hz, 1H, Bz-H), 7.45-7.26 (m, 7H, Ar—H), 5.91 (d, J=3.4 Hz, 1H, H-1), 5.40 (ddd, J=8.0, 6.2, 2.0 Hz, 1H, H-5), 4.91 (dd, J=12.8, 2.0 Hz, 1H, H-6a), 4.70 (d, J=11.0 Hz, 1H, CH$_2$Ph), 4.60 (d, J=3.4 Hz, 1H, H-2), 4.599 (d, J=11.0 Hz, 1H, CH$_2$Ph), 4.49 (dd, J=12.8, 6.2 Hz, 1H, H-6b), 4.46 (dd, J=8.0, 3.4 Hz, 1H, H-4), 4.13 (d, J=3.4 Hz, 1H, H-3), 2.98 (s, 3H, CH$_3$), 1.49 (s, 3H, CH$_3$), 1.31 (s, 3H, CH$_3$).

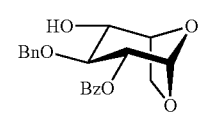

11

3-O-Benzyl-1,6-anhydro-β-L-idopyranose (11)

To a solution of 10 (1.20 g, 2.44 mmol) in a mixed solvent of CH$_2$Cl$_2$ and t-BuOH (2/1 ratio, 18 mL) was added potassium t-butoxide (0.60 g, 5.36 mmol) at 0° C. under nitrogen. After stirring for 16 h, the reaction was acidified with 0.6 N H$_2$SO$_{4(aq)}$ (ca. 4.5 mL) and the flask was equipped with a simple distillation head to evaporate CH$_2$Cl$_2$ and t-BuOH under reduced pressure. 0.6 N H$_2$SO$_{4(aq)}$ (5 mL) and diglyme (10 mL) were added to the resulting solution, and the mixture was kept stirring at 160° C. for another 16 h. After cooling to room temperature, the reaction was neutralized with 3 N NaOH$_{(aq)}$ (2 mL), and the solvent was removed on rotary evaporator under vacuum. Water (10 mL) was added to the residue, and the mixture was extracted with EtOAc (3×10 mL). The combined organic layers were washed with brine, dried over MgSO$_4$, filtered, and concentrated in vacuo. The residue was purified by flash column chromatography (EtOAc/Hex=1/1) to give a white solid, which was further recrystallized via vapor diffusion method to provide 11 (0.32 g, 52%) as colorless crystals. $^1$H NMR (400 MHz, CDCl$_3$) δ 7.36-7.28 (m, 5H, Ar—H), 5.27 (d, J=1.8 Hz, 1H, H-1), 4.93 (d, J=11.7 Hz, 1H, CH$_2$Ph), 4.72 (d, J=11.7 Hz, 1H, CH$_2$Ph), 4.41 (t, J=4.9 Hz, 1H, H-5), 4.01 (d, J=7.8 Hz, 1H, H-6a), 3.85 (ddd, J=7.8, 4.9, 3.3 Hz, 1H, H-4), 3.71 (dd, J=7.8, 4.9 Hz, 1H, H-6b), 3.64 (td, J=7.8, 1.8 Hz, 1H, H-2), 3.37 (t, J=7.8 Hz, 1H, H-3), 2.09 (d, J=3.3 Hz, 1H, OH-4), 1.89 (d, J=7.8 Hz, 1H, OH-2).

D

2-O-Benzoyl-3-O-benzyl-1,6-anhydro-β-L-idopyranose (D)

To a solution of 11 (3.00 g, 11.9 mmol) in dichloromethane (35 mL) was consecutively added pyridine (3.0 mL, 35.7 mmol) and benzoyl chloride (1.4 mL, 12.5 mmol) at 0° C. under nitrogen. After stirring for 4 h, the reaction was quenched with MeOH, and the solvent was evaporated at reduced pressure. The mixture was dissolved in EtOAc, and the solution was sequentially washed with 2 N HCl$_{(aq)}$, saturated NaHCO$_{3(aq)}$, water, and brine. The organic layer was dried over anhydrous MgSO$_4$, filtered, and concentrated in vacuo. The residue was recrystallized from EA/Hex=1/4 to afford the 4-alcohol D (3.60 g, 85%) as a white solid. $^1$H NMR (400 MHz, CDCl$_3$) δ 8.08 (dd, J=7.6, 1.3 Hz, 2H, Bz-H), 7.59 (tt, J=7.6, 1.3 Hz, 1H, Bz-H), 7.46 (t, J=7.6 Hz, 2H, Bz-H), 7.29-7.24 (m, 5H, Ar—H), 5.53 (d, J=1.6 Hz, 1H, H-1), 5.07 (dd, J=8.2, 1.6 Hz, 1H, H-2), 4.80 (d, J=11.6 Hz, 1H, CH$_2$Ph), 4.65 (d, J=11.6 Hz, 1H, CH$_2$Ph), 4.51 (t, J=4.6 Hz, 1H, H-5), 4.15 (d, J=7.5 Hz, 1H, H-6a), 4.00 (ddd, J=8.2, 4.6, 3.0 Hz, 1H, H-4), 3.87 (t, J=8.2 Hz, 1H, H-3), 3.76 (dd, J=7.5, 4.6 Hz, 1H, H-6b), 2.22 (d, J=3.0 Hz, 1H, OH-4).

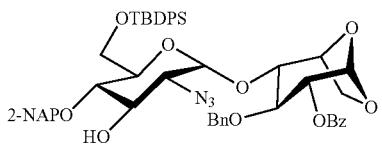

12

1,6-Anhydro-4-O-(2-azido-6-O-tertbutyldiphenylsilyl-2-deoxy-4-O-(2-naphthylmethyl)-α-D-glucopyranosyl)-2-O-benzoyl-3-O-benzyl-β-L-idopyranose (12)

A mixture of the thioglycoside C (4.30 g, 6.23 mmol) and acceptor D (3.33 g, 9.34 mmol) in dry CH$_2$Cl$_2$ (70.0 mL) was added to a reaction flask containing freshly dried 4 Å molecular sieves under nitrogen. The mixture was stirred at room temperature for 1 h, and the solution was cooled to −60° C. N-Iodosuccinimide (NIS, 1.74 g, 8.10 mmol) and trifluoromethanesulfonic acid (TfOH, 220.0 μL, 2.49 mmol) were added to the reaction flask, and the mixture was gradually warmed up to −40° C. The resulting solution was kept stirring for 3 h, and Et$_3$N was added to quench the reaction. The whole mixture was filtered through Celite followed by washing with CH$_2$Cl$_2$, and the filtrate was sequentially washed with 10% Na$_2$S$_2$O$_{3(aq)}$ and brine. The organic layer was dried over anhydrous MgSO$_4$. The residue was filtered and concentrated in vacuo to give the crude product which was purified by flash column chromatography (EtOAc/Hex=1/5) to give the disaccharide 12 (4.00 g, 70%).

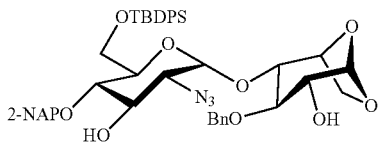

13

1,6-Anhydro-4-O-(2-azido-6-O-tertbutyldiphenylsilyl-2-deoxy-4-O-(2-naphthylmethyl)-α-D-glucopyranosyl)-3-O-benzyl-β-L-idopyranose (13)

NaOMe (6.00 mg, 0.11 mmol) was added to a solution of compound 12 (0.10 g, 0.11 mmol) in MeOH (5 mL) ar room temperature under nitrogen atomsphere. After stirring for 3 h, the reaction was neutralized by adding DOWEX 50WX4-200 resin. The mixture was filtered, and the filtrate was concentrated under reduced pressure, purified by flash column chromatography (EtOAc/Hex=1/2) to give the disaccharide 13 (0.08 g, 92%). $^1$H NMR (400 MHz, CDCl$_3$) δ 7.82 (dd, J=3.4, 6.0 Hz, 1H, Ar—H), 7.79-7.76 (m, 2H, Ar—H), 7.70-7.67 (m, 5H, Ar—H), 7.51-7.48 (m, 2H, Ar—H), 7.44-7.40 (m, 4H, Ar—H), 7.39-7.30 (m, 8H, Ar—H), 5.27-5.24 (m, 2H, H-1, H-1'), 4.94 (d, J=11.2 Hz, 1H, CH$_2$Ph), 4.90 (s, 2H, CH$_2$Ph), 4.83 (d, J=11.2 Hz, 1H, CH$_2$Ph), 4.51 (t, J=4.6 Hz, 1H, H-5), 4.11 (dd, J=10.1, 8.3 Hz, 1H, H-3'), 3.98 (d, J=7.7 Hz, 1H, H-6a), 3.90-3.85 (m, 3H, H-6'a, H-6'b, H-4), 3.65-3.56 (m, 5H, H-2, H-3, H-6b, H-4', H-5'), 3.24 (dd, J=3.8, 10.1 Hz, 1H, H-2'), 1.09 (s, 9H, t-Bu).

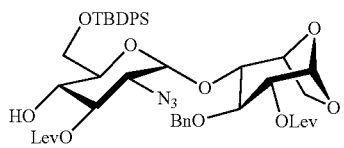

14

1,6-Anhydro-4-O-(2-azido-6-O-tert-butyldiphenylsilyl-2-deoxy-3-O-levulinyl-α-D-glucopyranosyl)-3-O-benzyl-2-O-levulinyl-β-L-idopyranose (14)

Disaccharide 13 (0.23 g, 0.28 mmol) and the residue, EDC (0.27 g, 1.40 mmol) and DMAP (4.0 mg, 0.03 mmol) were dissolved in CH$_2$Cl$_2$ (4 mL) and the reaction flask was cooled to 0° C. LevOH (0.32 g, 2.80 mmol) was slowly added to the solution and the mixture was stirred for another 16 h. After that, DDQ (0.2 g, 0.84 mmol) in three equal portions in half-hour intervals and H$_2$O (0.2 ml) was added. After 4 h of stirring, the reaction was quenched by sat. NaHCO$_{3(aq)}$ followed by extraction with CH$_2$Cl$_2$. The combined organic layer was sequentially washed with saturated NaHCO$_{3(aq)}$, brine, dried over anhydrous MgSO$_4$, filtered, and concentrated under reduced pressure. The residue was purified by flash column chromatography (EtOAc/Hex=1/2) on silica gel to provide 4'-alcohol 14 (0.17 g, 70%). $^1$H NMR (600 MHz, CDCl$_3$) δ 7.65-7.62 (m, 4H, Ar—H), 7.42-7.23 (m, 11H, Ar—H), 5.34-5.31 (m, 2H, H-1, H-3'), 5.29 (d, J=3.5 Hz, 1H, H-1'), 4.81-4.78 (m, 2H, H-2, ArCH$_2$), 4.71 (d, J=11.1 Hz, 1H, ArCH$_2$), 4.54 (t, J=4.1 Hz, 1H, H-5), 4.10 (d, J=7.8 Hz, 1H, H-6a), 3.94-3.89 (m, 3H, H-3, H-5', H-6'a), 3.82-3.80 (m, 1H, H-6'b), 3.70-3.66 (m, 3H, H-4, H-4', H-6b), 3.27 (s, 1H, OH), 3.22 (dd, J=10.8, 3.5 Hz, 1H, H-2'), 2.95-2.89 (m, 1H), 2.81-2.76 (m, 1H), 2.72-2.61 (m, 3H), 2.58-2.45 (m, 3H), 2.17 (s, 3H, CH$_3$), 2.16 (s, 3H, CH$_3$), 1.03 (s, 9H, t-Bu).

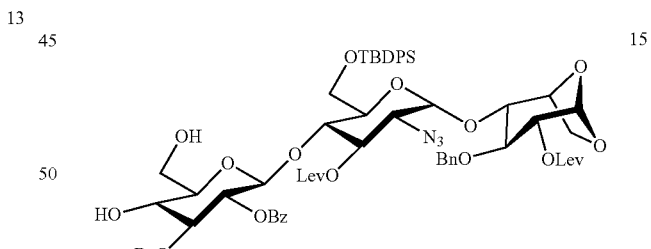

15

O-[2-O-Benzoyl-3-O-benzyl-β-D-glucopyranosyl]-(1→4)-O-[2-azido-6-O-tert-butyldiphenylsilyl-2-deoxy-3-O-levulinyl-α-D-glucopyranosyl]-(1→4)-O-1,6-anhydro-3-O-benzyl-2-O-levulinyl-β-L-idopyranose (15)

A mixture of the thioglycoside B (0.16 g, 0.28 mmol) and acceptor 14 (0.19 g, 0.21 mmol) in dry CH$_2$Cl$_2$ (3.0 mL) was added to a reaction flask containing freshly dried 3 Å molecular sieves under nitrogen. The mixture was stirred at room temperature for 1 h, and the solution was cooled to −60° C. N-Iodosuccinimide (NIS, 0.23 g, 0.32 mmol) and trifluoromethanesulfonic acid (TfOH, 4.0 μL, 42.0 μmol)

were added to the reaction flask, and the mixture was gradually warmed up to −40° C. The resulting solution was kept stirring for 3 h and warmed up to 0° C. TFA (0.5 mL), H$_2$O (0.1 mL) was added and stirred for 1 h. Saturated NaHCO$_{3(aq)}$ was added to quench the reaction and the whole mixture was filtered through Celite followed by washing with CH$_2$Cl$_2$, and the filtrate was sequentially washed with 10% Na$_2$S$_2$O$_{3(aq)}$ and brine. The organic layer was dried over anhydrous MgSO$_4$. The residue was filtered and concentrated in vacuo to give the crude product which was purified by flash column chromatography (EtOAc/Hex=1/3) to give the disaccharide 15 (0.15 g, 58%). $^1$H NMR (600 MHz, CDCl$_3$) δ 7.73-7.71 (m, 4H, Ar—H), 7.64-7.62 (m, 2H, Ar—H), 7.49-7.40 (m, 5H, Ar—H), 7.36-7.25 (m, 6H, Ar—H), 7.71-7.14 (m, 5H, Ar—H), 5.32 (t, J=10.0 Hz, 1H, H-3'), 5.28-5.26 (m, 2H, H-1, H-1'), 5.12 (dd, J=9.2, 8.5 Hz, 1H, H-2"), 4.79-4.76 (m, 2H, H-1", ArCH2), 4.74 (dd, J=8.1, 1.5 Hz, 1H, H-2), 4.70-4.63 (m, 3H, ArCH$_2$), 4.10-4.07 (m, 2H, H-5, H-4'), 3.99-3.91 (m, 4H, H-4", H-6"a, H-6"b, H-6a), 3.86-3.78 (m, 3H, H-3, H-6'a, OH), 3.63 (d, J=11.3 Hz, 1H, H-6'b), 3.51 (m, 2H, H-3", OH), 3.40-3.38 (m, 2H, H-4, H-6b), 3.33-3.31 (m, 1H, H-5), 3.26-3.24 (m, 1H, H-5'), 3.23 (dd, J=10.0, 3.6 Hz, 1H, H-2') 2.93-2.87 (m, 1H), 2.81-2.76 (m, 1H), 2.71-2.63 (m, 2H), 2.56-2.44 (m, 4H), 2.22 (s, 3H, CH$_3$), 2.14 (s, 3H, CH$_3$), 1.07 (s, 9H, t-Bu).

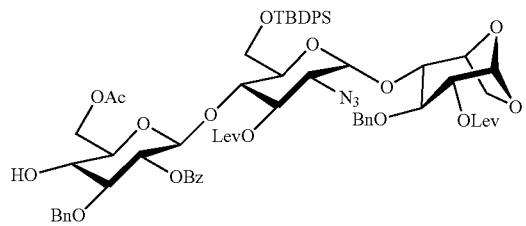

16

O-[6-O-Acetyl-2-O-benzoyl-3-O-benzyl-β-D-glucopyranosyl]-(1→4)-O-[2-azido-6-O-tert-butyldiphenylsilyl-2-deoxy-3-O-levulinyl-α-D-glucopyranosyl]-(1→4)-O-1,6-anhydro-3-O-benzyl-2-O-levulinyl-β-L-idopyranose (16)

A solution of compound 15 (0.20 g, 0.16 mmol) in dichloromethane (4.0 mL) were sequentially added Et$_3$N (0.30 mL, 2.08 mmol), Ac$_2$O (0.03 mL, 0.32 mmol) and at 0° C. under nitrogen and warmed up to room temperature. After 16 h, MeOH was added and stirred for 10 min to quench the reaction and the solvents were evaporated under reduced pressure. EtOAc and water were added to the residue, and the desired material was extracted with EtOAc. The combined organic layer was washed with brine, dried over anhydrous MgSO$_4$, filtered, and concentrated under reduced pressure. The residue was purified by flash column chromatography (EtOAc/Hex=1/3) on silica gel to furnish the desired product 16 (0.17 g, 82%). $^1$H NMR (600 MHz, CDCl$_3$) δ 7.76-7.71 (m, 4H, Ar—H), 7.63-7.62 (m, 2H, Ar—H), 7.49-7.39 (m, 5H, Ar—H), 7.35-7.24 (m, 9H, Ar—H), 7.18-7.13 (m, 5H, Ar—H), 5.33 (t, J=10.1 Hz, 1H, H-3'), 5.30 (d, J=3.5 Hz, 1H, H-1'), 5.27 (m, 1H, H-1), 5.14 (t, J=8.8 Hz, 1H, H-2"), 4.81-4.54 (m, 7H, ArCH$_2$, H-1", H-2, H-6"a), 4.23-4.21 (m, 1H, H-6"b), 4.10-4.07 (m, 2H, H-5, H-4'), 3.95 (d, J=7.9 Hz, 1H, H-6a), 3.87 (t, J=8.1 Hz, 1H, H-3), 3.80-3.79 (m, 2H, H-4, H-6'a), 3.64 (d, J=11.6 Hz, 1H, H-6'b), 3.60 (t, J=9.3 Hz, 1H, H-4"), 3.48-3.42 (m, 2H, H-3", H-6b), 3.35-3.34 (m, 1H, H-5"), 3.28-3.26 (m, 1H, H-5'), 3.20 (dd, J=10.1, 3.5 Hz, 1H, H-2'), 3.01 (brs, 1H, OH), 2.83-2.63 (m, 6H), 2.56-2.44 (m, 2H), 2.20 (s, 3H, CH$_3$), 2.14 (s, 3H, CH$_3$), 2.12 (s, 3H, CH$_3$), 1.06 (s, 9H, t-Bu).

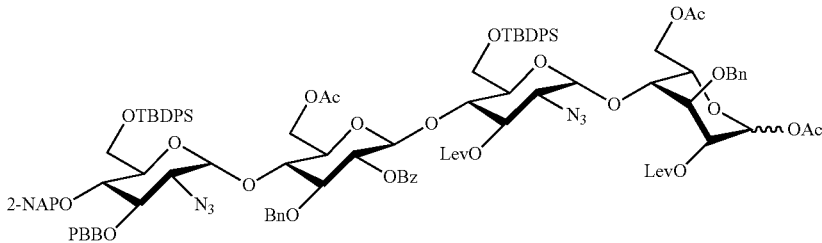

17

O-[2-Azido-3-O-(p-bromobenzyl)-6-O-tert-butyldiphenyl-2-deoxy-4-O-(2-naphthylmethyl)-α-D-glucopyranosyl]-(1→4)-O-[6-O-acetyl-2-O-benzoyl-3-O-benzyl-β-D-glucopyranosyl]-(1→4)-O-[2-azido-6-O-tert-butyldiphenylsilyl-2-deoxy-3-O-levulinyl-α-D-glucopyranosyl]-(1→4)-O-6-O-acetyl-3-O-benzyl-2-O-levulinyl-α,β-L-idopyranosyl acetate (17)

A mixture of the thioglycoside A (0.15 g, 0.17 mmol) and acceptor 16 (0.11 g, 0.08 mmol) in dry CH$_2$Cl$_2$ (3 mL) was added to a reaction flask containing freshly dried AW 300 molecular sieves under nitrogen. The mixture was stirred at room temperature for 1 h, and the solution was cooled to −78° C. N-Iodosuccinimide (NIS, 47.0 mg, 0.20 mmol) and trifluoromethanesulfonic acid (1.50 μL, 17.0 μmol) were added to the reaction flask, and the mixture was gradually warmed up to −20° C. The resulting solution was kept stirring for 4 h and acetic anhydride (3 mL), trimethylsilyltrifluoromethanesulfonate (8.00 μL, 42.5 μmol) were added and stirred for another 8 h. Et$_3$N was added to quench the reaction. The whole mixture was filtered through celite followed by washing with CH$_2$Cl$_2$, and the filtrate was sequentially washed with 10% Na$_2$S$_2$O$_{3(aq)}$ and brine. The organic layer was dried over anhydrous MgSO$_4$. The residue was filtered and concentrated in vacuo to get the crude product which was purified by flash column chromatography (EtOAc/Hex=1/2) to get the tetrasaccharide 17 (0.12 g, 65%). $^1$H NMR (600 MHz, CDCl$_3$) δ 7.82-7.80 (m, 2.2H, Ar—H), 7.76-7.75 (m, 8.3H, Ar—H), 7.70-7.67 (m, 4.8H, Ar—H), 7.65-7.60 (m, 15.6H, Ar—H), 7.49-7.45 (m, 13.8H, Ar—H), 7.41-7.13 (m, 71.5H, Ar—H), 6.03 (d, J=2.2 Hz, 1H), 5.84 (s, 1H), 5.56-5.54 (m, 1.9H), 5.28-5.17 (m, 4.4H), 5.03 (s, 1.3H), 4.94-4.85 (m, 9.9H), 4.81-4.68 (m, 10.6H), 4.58-4.54 (m, 3.5H), 4.30-4.28 (m, 2.6H), 4.17-3.87 (m, 23.4H), 3.80-3.67 (m, 10.6H), 3.61-3.60 (m, 3.3H), 3.52-3.46 (m, 4.4H), 3.30-3.28 (m, 1.2H), 3.23-3.22 (m, 2.9H), 2.76-2.52 (m, 18.1H), 2.17 (s, 3.9H), 2.14 (s, 3.2H), 2.10 (s, 6.2H), 2.07 (s, 3.6H), 2.00 (s, 3.7H), 1.85 (s, 3.5H), 1.75 (s, 10.2H), 1.07 (s, 21.3H), 1.02 (s, 19.3H).

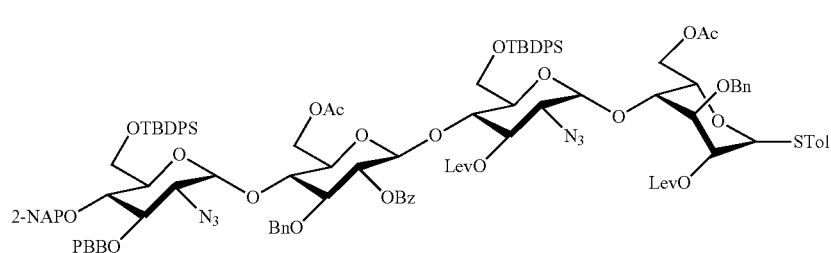

p-Methylphenyl [2-azido-3-O-(p-bromobenzyl)-6-O-tert-butyldiphenyl-2-deoxy-4-O-(2-naphthylmethyl)-α-D-glucopyranosyl]-(1→4)-O-[6-O-acetyl-2-O-benzoyl-3-O-benzyl-β-D-glucopyranosyl]-(1→4)-O-[2-azido-6-O-tert-butyldiphenylsilyl-2-deoxy-3-O-levulinyl-α-D-glucopyranosyl]-(1→4)-O-6-O-acetyl-3-O-benzyl-2-O-levulinyl-α-L-idopyranose (18)

Trimethyl(p-tolylthio)silane (TMSSTol, 0.26 g, 0.81 mmol) and ZnI$_2$ (92.0 mg, 0.48 mmol) were added to a was gradually warmed up to 0° C. The resulting solution was 6.0 mL). After 1 h of stirring at room temperature, the mixture was diluted with CH$_2$Cl$_2$ (15 mL). The organic layer was washed with saturated NaHCO$_{3(aq)}$, dried over anhydrous MgSO$_4$, filtered and concentrated in vacuo. Purification of the residue via flash column chromatography (EtOAc/Hex=1/5) provided the product 18 (0.29 g, 85%). $^1$H NMR (600 MHz, CDCl$_3$) δ 7.82-7.80 (m, 1H, Ar—H), 7.76-7.74 (m, 4H, Ar—H), 7.70-7.60 (m, 10H, Ar—H), 7.51-7.45 (m, 5H, Ar—H), 7.41-7.39 (m, 4H, Ar—H), 7.38-7.30 (m, 10H, Ar—H), 7.29-7.24 (m, 6H, Ar—H), 7.23-7.17 (m, 6H, Ar—H), 7.16-7.13 (m, 2H, Ar—H), 7.05 (d, J=8.0 Hz, 2H, Ar—H), 5.56 (d, J=3.8 Hz, 1H, H-1″′), 5.52-5.16 (m, 3H, H-2″, H-3′, H-1), 5.10 (t, J=2.5 Hz, 1H, H-2), 4.95-4.91 (m, 2H, ArCH$_2$), 4.86 (d, J=11.1 Hz, 1H, ArCH$_2$), 4.82-4.80 (m, 3H, H-1′, ArCH$_2$), 4.76 (d, J=10.0 Hz, 1H, ArCH$_2$), 4.72 (d, J=8.1 Hz, 1H, H-1″), 4.66-4.58 (m, 1H, H-5), 4.56-4.53 (m, 2H, ArCH$_2$), 4.30-4.28 (m, 1H, H-6″a), 4.16 (dd, J=12.0, 4.9 Hz, 1H, H-6″b), 4.10-3.99 (m, 4H, H-4′, H-6a, H-6b, H-6′a), 3.96-3.92 (m, 2H, H-4, H-3″′), 3.90-3.86 (m, 2H, H-3, H-4″), 3.79-3.72 (m, 4H, H-3″, H-6′b, H-6″′a, H-6″′b), 3.62-3.60 (m, 1H, H-4″), 3.55 (m, 1H, H-5″′), 3.52-3.49 (m, 1H, H-5′), 3.47-3.44 (m, 1H, H-5″), 3.33 (dd, J=10.6, 3.4 Hz, 1H, H-2′), 3.24 (dd, J=9.7, 3.8 Hz, 1H, H-2″), 2.78-2.68 (m, 3H), 2.63-2.58 (m, 2H), 2.54-2.49 (m, 3H), 2.29 (s, 3H, CH$_3$), 2.17 (s, 3H, CH$_3$), 2.10 (s, 3H, CH$_3$), 1.78 (s, 3H, CH$_3$), 1.76 (s, 3H, CH$_3$), 1.08 (s, 9H, t-Bu), 1.03 (s, 9H, t-Bu).

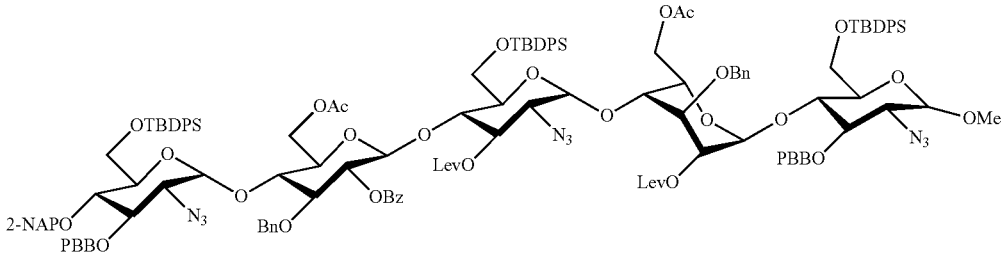

Methyl [2-azido-3-O-(p-bromobenzyl)-6-O-tert-butyldiphenyl-2-deoxy-4-O-(2-naphthylmethyl)-α-D-glucopyranosyl]-(1→4)-O-[6-O-acetyl-2-O-benzoyl-3-O-benzyl-β-D-glucopyranosyl]-(1→4)-O-[2-azido-6-O-tert-butyldiphenylsilyl-2-deoxy-3-O-levulinyl-α-D-glucopyranosyl]-(1→4)-O-[6-O-acetyl-3-O-benzyl-2-O-levulinyl-α-L-idopyranosyl]-(1→4)-2-azido-3-O-(p-bromobenzyl)-6-O-tert-butyldiphenylsilyl-2-deoxy-α-D-glucopyranoside (19)

A mixture of the tetrasaccharide 18 (0.16 g, 74.0 µmol) and acceptor E (55.0 mg, 88.0 µmol) in dry CH$_2$Cl$_2$ (4.0 mL) was added to a reaction flask containing freshly dried AW 300 molecular sieves under nitrogen. The mixture was stirred at room temperature for 1 h, and the solution was cooled to −20° C. N-Iodosuccinimide (NIS, 22.0 mg, 96.0 µmol) and trifluoromethanesulfonic acid (TfOH, 2.00 µL, 15.0 μmol) were added to the reaction flask, and the mixture was gradually warmed up to 0° C. The resulting solution was kept stirring for 4 h and Et$_3$N was added to quench the reaction. The whole mixture was filtered through Celite followed by washing with CH$_2$Cl$_2$, and the filtrate was sequentially washed with 10% Na$_2$S$_2$O$_{3(aq)}$ and brine. The organic layer was dried over anhydrous MgSO$_4$. The residue was filtered and concentrated in vacuo to give the crude product which was purified by flash column chromatography (EtOAc/Hex=1/3) to give the pentasaccharide 19 (0.11 g, 61%). $^1$H NMR (600 MHz, CDCl$_3$) δ 7.82-7.77 (m, 3H, Ar—H), 7.76-7.72 (m, 5H, Ar—H), 7.68-7.64 (m, 7H, Ar—H), 7.62-7.59 (m, 6H, Ar—H), 7.50-7.46 (m, 6H, Ar—H), 7.41-7.24 (m, 31H, Ar—H), 7.23-7.17 (m, 7H, Ar—H), 7.15-7.13 (m, 2H, Ar—H), 7.06-7.05 (m, 2H, Ar—H), 6.92-6.91 (m, 2H, Ar—H), 5.55-5.54 (m, 1H), 5.26 (t, J=10.0 Hz, 1H), 5.21 (t, J=8.7 Hz, 1H), 5.01 (s, 1H), 4.95-4.90 (m, 3H), 4.87-4.86 (m, 1H), 4.84 (s, 1H), 4.80-4.75 (m, 3H), 4.68-4.63 (m, 3H), 4.56 (d, J=10.7 Hz, 1H), 4.40 (d, J=11.1 Hz, 1H), 4.29 (d, J=11.7 Hz, 1H), 4.17 (dd, J=11.8, 4.5 Hz, 1H), 4.07 (t, J=9.8 Hz, 1H), 4.01-3.99 (m, 2H), 3.97-3.81 (m, 9H), 3.78-3.66 (m, 7H), 3.61-3.56 (m, 2H), 3.53-3.51 (m, 1H), 3.49-3.45 (m, 2H), 3.30-3.27 (m, 4H), 3.24-3.21 (m, 1H), 3.18-3.16 (m, 1H), 2.76-2.70 (m, 1H), 2.65-2.58 (m, 3H), 2.55-2.52 (m, 2H), 2.50-2.45 (m, 1H), 2.30-2.26 (m, 1H), 2.10-2.09 (m, 6H), 1.76 (s, 3H, CH$_3$), 1.57-1.55 (m, 4H), 1.07 (s, 9H, t-Bu), 1.02 (s, 9H, t-Bu), 0.97 (s, 9H, t-Bu).

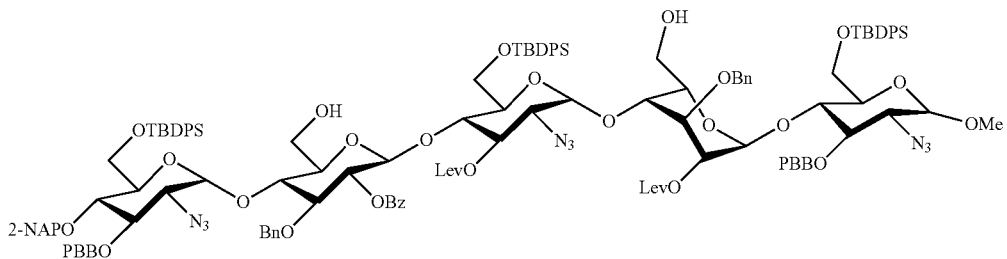

Methyl O-[2-azido-3-O-(p-bromobenzyl)-2-deoxy-4-O-(2-naphthylmethyl)-6-O-tert-butyldiphenyl-α-D-glucopyranosyl]-(1→4)-O-[2-O-benzoyl-3-O-benzyl-β-D-glucopyranosyl]-(1→4)-O-[2-azido-6-O-tert-butyldiphenylsilyl-2-deoxy-3-O-levulinyl-α-D-glucopyranosyl]-(1→4)-O-[3-O-benzyl-2-O-levulinyl-α-L-idopyranosyl]-(1→4)-2-azido-3-O-(p-bromobenzyl)-6-O-tert-butyldiphenylsilyl-2-deoxy-α-D-glucopyranoside (20)

Mg(OMe)$_2$ (1 mL) was added to a solution of compound 19 (0.13 g, 48.6 μmol) in CH$_2$Cl$_2$ (2 mL) at room temperature under nitrogen atomsphere. After stirring for 16 h, the reaction was neutralized by adding acetic acid. The mixture was concentrated under reduced pressure to give the crude product which was purified by flash column chromatography (EtOAc/Hex=1/3) to give the pentasaccharide 20 (0.11 g, 88%). $^1$H NMR (600 MHz, CDCl$_3$) δ 7.82-7.80 (m, 2H, Ar—H), 7.78-7.76 (m, 3H, Ar—H), 7.74-7.72 (m, 3H, Ar—H), 7.69-7.761 (m, 19H, Ar—H), 7.57-7.55 (m, 1H, Ar—H), 7.49-7.45 (m, 8H, Ar—H), 7.42-7.16 (m, 59H, Ar—H), 7.15-7.13 (m, 6H, Ar—H), 7.02-6.98 (m, 3H, Ar—H), 5.61 (d, J=3.8 Hz, 1H), 5.25 (t, J=10.0 Hz, 1H), 5.20 (dd, J=9.3, 8.3 Hz, 1H), 5.05 (d, J=2.7 Hz, 1H), 5.02 (d, J=3.7 Hz, 1H), 4.91-4.75 (m, 11H), 4.70-4.66 (m, 3H), 4.64 (d, J=11.1 Hz, 1H), 4.59-4.57 (m, 3H), 4.46 (d, J=11.1 Hz, 1H), 4.13-4.05 (m, 4H), 4.00-3.86 (m, 14H), 3.85-3.75 (m, 9H), 3.72-3.65 (m, 4H), 3.60-3.56 (m, 2H), 3.55-3.54 (m, 1H), 3.45 (d, J=9.9 Hz, 1H), 3.36-3.29 (m, 4H), 3.25-3.21 (m, 3H), 3.20-3.10 (m, 3H), 2.78-2.66 (m, 3H), 2.61-2.45 (m, 8H), 2.30-2.25 (m, 1H), 2.10 (s, 3H, CH$_3$), 2.07 (s, 3H, CH$_3$), 1.07 (s, 9H, t-Bu), 1.03 (s, 9H, t-Bu), 0.97 (s, 9H, t-Bu).

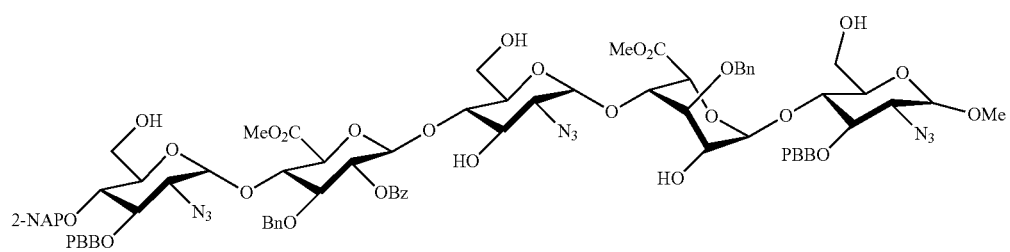

21

Methyl O-[2-azido-3-O-(p-bromobenzyl)-2-deoxy-4-O-(2-naphthylmethyl)-α-D-glucopyranosyl]-(1→4)-O-[methyl 2-O-benzoyl-3-O-benzyl-β-D-glucopyranosiduronate]-(1→4)-O-[2-azido-2-deoxy-β-D-glucopyranosyl]-(1→4)-O-[methyl 3-O-benzyl-α-L-idopyranosiduronate]-(1→4)-2-azido-3-O-(p-bromobenzyl)-2-deoxy-α-D-glucopyranoside (21)

BAIB (32.0 mg, 0.10 mmol) was added to a solution of the compound 20 (50.0 mg, 19.0 μmol) in a mixed solvent (CH$_2$Cl$_2$/H$_2$O=2/1, 0.75 mL) at room temperature. After 5 min, TEMPO (1.22 mg, 7.60 μmol) was placed into the mixture which was then kept stirring for 24 h. To quench the reaction, 10% Na$_2$S$_2$O$_{3(aq)}$ was added, and the desired material was extracted with CH$_2$Cl$_2$. The combined organic layer was washed with brine, dried over anhydrous MgSO$_4$, filtered, and concentrated under reduced pressure. Then, hydrazine monohydrate (1 M solution in pyridine/AcOH=1.4/1, 0.2 mL, 0.06 mmol) was added to a solution of the residue in CH$_2$Cl$_2$ (1.0 mL) at room temperature. After stirring for 2 h, the reaction was quenched by acetone, and the solvents were evaporated under reduced pressure. To the crude uronate solution in CH$_2$Cl$_2$ (1.0 mL) was added an ethereal solution of diazomethane (0.6 mmol), and the reaction mixture was stirred at room temperature for 16 h. The reaction solution was quenched by acetic acid and the resulting mixture was concentrated in vacuo to yield the crude residue. A 70% solution of HF in pyridine (0.25 mL) was added to an ice-cooled solution of the crude residue in pyridine (1.0 mL). The mixture was allowed to warm to room temperature and stirred for 3 days. The mixture solution was concentrated in vacuo, and the residue was purified by flash column chromatography (MeOH/CH$_2$Cl$_2$=1/9) to afford the desilylated compound 21 (28.0 mg, 82%). $^1$H NMR (600 MHz, CDCl$_3$) δ 7.91-7.90 (m, 2H, Ar—H), 7.73-7.67 (m, 4H, Ar—H), 7.58-7.56 (m, 1H, Ar—H), 7.51-7.48 (m, 1H, Ar—H), 7.40-7.34 (m, 5H, Ar—H), 7.32-7.30 (m, 2H, Ar—H), 7.28-7.19 (m, 12H, Ar—H), 7.16 (s, 1H, Ar—H), 7.10-7.04 (m, 10H, Ar—H), 6.92-6.89 (m, 2H), 5.37 (d, J=3.7 Hz, 1H), 5.22 (t, J=6.9 Hz, 1H), 5.11 (m, 1H), 4.81-4.66 (m, 10H), 4.60-4.57 (m, 6H), 4.46-4.39 (m, 4H), 4.28 (dd, J=9.0, 8.4 Hz, 1H), 4.15-4.13 (m, 2H), 3.86 (t, J=7.5 Hz, 1H), 3.82-3.68 (m, 16H), 3.66-3.61 (m, 5H), 3.59-3.50 (m, 7H), 3.42 (s, 2H), 3.38-3.34 (m, 3H), 3.31-3.25 (m, 8H), 3.15-3.12, (m, 1H), 3.00 (s, 3H, CH$_3$), 2.33 (brs, 2H, OH), 1.79-1.73 (m, 3H, OH).

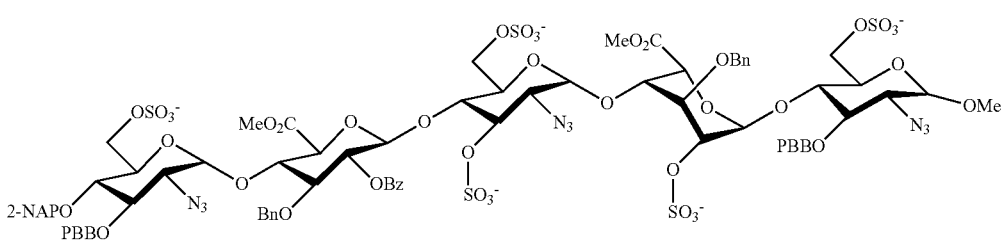

22

Methyl O-[2-azido-3-O-(p-bromobenzyl)-2-deoxy-4-O-(2-naphthylmethyl)-6-O-sulfonato-α-D-glucopyranosyl]-(1→4)-O-[methyl 2-O-benzoyl-3-O-benzyl-β-D-glucopyranosiduronate]-(1→4)-O-[2-azido-2-deoxy-3,6-di-O-sulfonato-α-D-glucopyranosyl]-(1→4)-O-[methyl 3-O-benzyl-2-O-sulfonato-α-L-idopyranosiduronate]-(1→4)-2-azido-3-O-(p-bromobenzyl)-2-deoxy-6-O-sulfonato-α-D-glucopyranoside (22)

A solution of the pentaol 21 (40.0 mg, 23.0 μmol) and sulfur trioxide-triethylamine complex (0.21 g, 1.15 mmol) in DMF (2 mL) was kept stirring at 60° C. under nitrogen for 3 d. The reaction flask was cooled down to room temperature, a solution of phosphate buffer (pH=7, 2.0 mL) was added and the mixture was kept stirring for another 30 min. The resulting solution was concentrated in vacuo and the residue was purified by flash column chromatography (MeOH/CH$_2$Cl$_2$=1/7) to give the O-sulfonated compound 22 (36.0 mg, 73%). $^1$H NMR (600 MHz, CDCl$_3$) δ 8.22 (d, J=7.8 Hz, 2H, Bz-H), 7.80-7.76 (m, 3H, Ar—H), 7.73 (s, 1H, Ar—H), 7.69-7.65 (m, 1H, Ar—H), 7.57-7.54 (m, 2H, Ar—H), 7.45-7.42 (m, 5H, Ar—H), 7.36-7.27 (m, 8H, Ar—H), 7.17 (d, J=8.2 Hz, 1H, Ar—H), 7.11-7.10 (m, 3H, Ar—H), 7.05-7.04 (m, 2H, Ar—H), 6.94 (d, J=8.2 Hz, 1H, Ar—H), 5.42-5.39 (m, 2H), 5.33 (s, 1H), 5.14 (d, J=8.1 Hz, 1H), 5.11 (d, J=3.5 Hz, 1H), 4.99 (d, J=11.0 Hz, 1H), 4.91-4.86 (m, 3H), 4.82-4.77 (m, 4H), 4.71 (s, 1H), 4.62-4.52 (m, 4H), 4.40-4.12 (m, 13H), 3.91-3.79 (m, 7H), 3.75-3.60 (m, 6H), 3.48-3.34 (m, 7H), 3.16 (d, J=9.9 Hz, 1H), 2.73 (s, 2H).

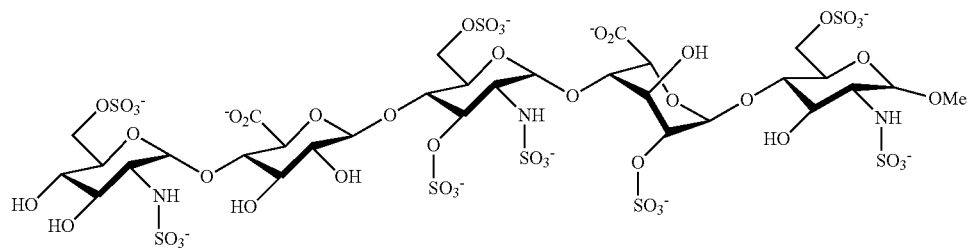

Methyl O-(2-deoxy-2-sulfamido-6-O-sulfonato-α-D-glucopyranosyl)-(1→4)-O-(β-D-glucopyranosyluronic acid)-(1→4)-O-(2-deoxy-2-sulfamido-3,6-di-O-sulfonato-α-D-glucopyranosyl)-(1→4)-O-(2-O-sulfonato-α-L-idopyranosyluronic acid)-(1→4)-2-deoxy-2-sulfamido-6-O-sulfonato-α-D-glucopyranoside decasodium salt (25)

1.0 M solution of LiOH in water (1.2 mL, 1.2 mmol) and 37% $H_2O_2$ (0.21 mL, 2.5 mmol) were added to a solution of the compound 22 (10.0 mg, 4.5 μmol) in THF (0.3 mL) and MeOH (0.3 mL) at room temperature. The mixture was kept stirring at 37° C. for 5 days, and the reaction solution was neutralized by acetic acid. The mixture was concentrated in vacuo, and the residue was purified by column chromatography on Sephadex LH-20 using MeOH as an eluent. The appropriate fractions were pooled and passed through a column of Bio-rad 50×8 $Na^+$ resin with MeOH to give the uronate compound 23. A solution of the uronate compound and 20% $Pd(OH)_2$ on carbon (100 mg) in phosphate buffer (pH=7.0, 2 mL) was equipped with a hydrogen balloon, and the mixture was stirred at room temperature for 2 d. The whole mixture was filtered through Celite, and the filtrate was concentrated in vacuo. The residue was dissolved in $H_2O$ (1 mL), and purified through a Sephadex G-25 column eluted with water. After concentration, the residue was passed through a column of Bio-rad 50×8 $Na^+$ resin using water as eluent to give the amino-alcohol compound 24. The above amino-alcohol residue was dissolved in water (2 mL), and the solution was adjusted to pH=9.5 through addition of 1.0 N $NaOH_{(aq)}$. Sulfur trioxide-pyridine complex (0.1 g) was added to the mixture in four equal portions with half-hour intervals at room temperature, and the pH value was maintained at 9.5 via calibration of 1.0 N $NaOH_{(aq)}$. After stirring for 18 h, the reaction mixture was concentrated in vacuo, and the residue was purified by column chromatography on Sephadex G-25 using water as an eluent. The appropriate fractions were pooled and passed through a column of Dowex 50WX8-$Na^+$ with water. The product portion was lyophilized to give the target molecule 25 (4.5 mg, 60%). $^1H$ NMR (600 MHz, $CDCl_3$) δ 5.64 (d, J=3.7 Hz, 1H), 5.55 (d, J=3.4 Hz, 1H), 5.19 (d, J=4.0 Hz, 1H), 5.04 (d, J=3.5 Hz, 1H), 4.76-4.74 (m, 1H), 4.63 (d, J=7.8 Hz, 1H), 4.50-4.49 (m, 2H), 4.43-4.35 (m, 7H), 4.32-4.30 (m, 2H), 4.28-4.26 (m, 2H), 4.18-4.15 (m, 7H), 4.00-3.96 (m, 4H), 3.91-3.89 (m, 2H), 3.86-3.82 (m, 2H), 3.80-3.77 (m, 4H), 3.68-3.57 (m, 5H), 3.47-3.41 (m, 8H), 3.30-3.25 (m, 3H).

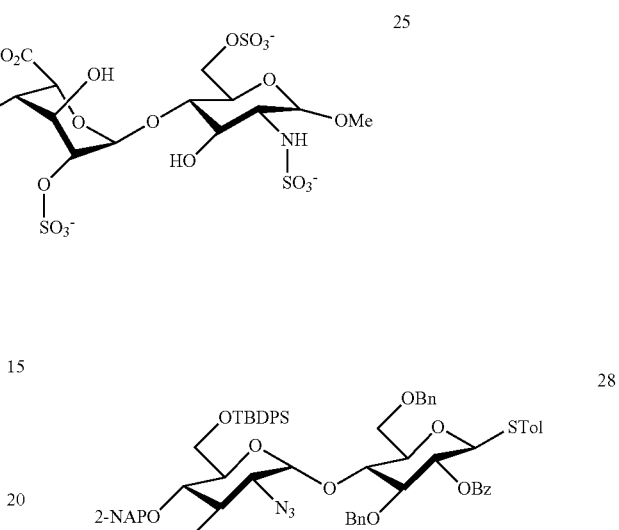

p-Methylphenyl 4-O-[2-azido-3-O-(p-bromobenzyl)-6-O-tert-butyl-diphenylsilyl-2-deoxy-4-O-(2-naphthylmethyl)-α-D-glucopyranosyl]-2-O-benzoyl-3,6-di-O-benzyl-1-thio-β-D-glucopyranoside A mixture of the compound 27 (2.20 g, 2.64 mmol) and acceptor 26 (1.25 g, 2.20 mmol) in dry $CH_2Cl_2$ (60 mL) was added to a reaction flask containing freshly dried 4 Å molecular sieves under nitrogen. The mixture was stirred at room temperature for 1 h, and the solution was cooled to −40° C. and AgOTf (2.80 g, 11.0 mmol) were added to the reaction flask, and the mixture was gradually warmed up to −20° C. The resulting solution was kept stirring for 4 h, and $Et_3N$ was added to quench the reaction. The whole mixture was filtered through celite followed by washing with $CH_2Cl_2$, and the filtrate was sequentially washed with brine. The organic layer was dried over anhydrous $MgSO_4$. The residue was filtered and concentrated in vacuo to give the crude product which was purified by flash column chromatography (EtOAc/Hex=1/7) to give the disaccharide 28 (2.01 g, 72%).

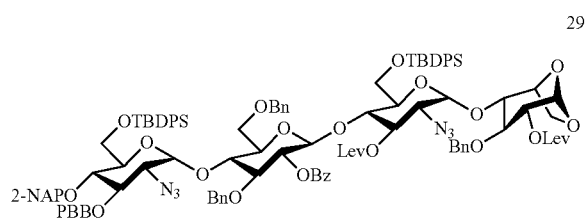

O-[2-Azido-3-O-(p-bromobenzyl)-6-O-tert-butyldiphenyl-2-deoxy-4-O-(2-naphthylmethyl)-α-D-glucopyranosyl]-(1→4)-O-[6-O-acetyl-2-O-benzoyl-3-O-benzyl-β-D-glucopyranosyl]-(1→4)-O-[2-azido-6-O-tert-butyldiphenylsilyl-2-deoxy-3-O-levulinyl-α-D-glucopyranosyl]-(1→4)-O-1,6-anhydro-3-O-benzyl-2-O-levulinyl-β-L-idopyranose xy-4-O-(2-naphthylmethyl)-α-D-glucopyranosyl]-2-O-benzoyl-3,6-di-O-benzyl-1-thio-β-D-glucopyranoside A mixture of the thioglycoside 28 (80.0 mg, 0.06 mmol) and acceptor 14 (44.0 g, 0.05 mmol) in dry $CH_2Cl_2$ (2 mL)

was added to a reaction flask containing freshly dried AW 300 molecular sieves under nitrogen. The mixture was stirred at room temperature for 1 h, and the solution was cooled to −40° C. N-Iodosuccinimide (17.0 mg, 0.08 mmol) and trifluoromethanesulfonic acid (1.00 µL, 10.0 µmol) were added to the reaction flask, and the mixture was gradually warmed up to −20° C. The resulting solution was kept stirring for 4 h and Et$_3$N was added to quench the reaction. The whole mixture was filtered through celite followed by washing with CH$_2$Cl$_2$, and was sequentially washed with 10% Na$_2$S$_2$O$_{3(aq)}$ and brine. The organic layer was dried over anhydrous MgSO$_4$. The residue was filtered and concentrated in vacuo to get the crude product which was purified by flash column chromatography (EtOAc/Hex=1/3) to get the tetrasaccharide 29 (150 mg, 60%).

Other Embodiments

This application refers to various issued patents, published patent applications, journal articles, books, manuals, and other publications, all of which are incorporated herein by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A compound of Formula (I):

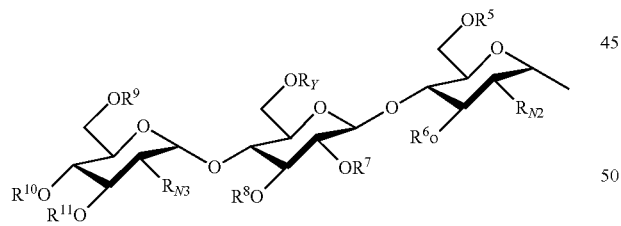

(I)

-continued

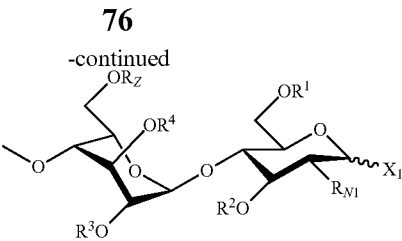

wherein:

$X_1$ is —OR$^A$ or —SR$^A$, wherein R$^A$ is hydrogen, an oxygen or sulfur protecting group, optionally substituted C$_{1-10}$ alkyl, optionally substituted aryl, optionally substituted acyl, or optionally substituted imidoyl;

R$^2$ and R$^{11}$ are independently optionally substituted arylalkyl;

R$_{N1}$, R$_{N2}$, and R$_{N3}$ are independently —N$_3$ or —N(R$^W$)$_2$, wherein each R$^W$ is independently hydrogen or a nitrogen protecting group;

R$^3$ and R$^6$ are independently —C(O)R$^D$, wherein each occurrence of R$^D$ is independently optionally substituted alkyl or optionally substituted aryl;

R$^1$, R$^5$, and R$^9$ are independently selected from the group consisting of optionally substituted arylalkyl and —Si(R$^B$)$_3$, wherein each R$^B$ is independently alkyl or aryl;

R$^{10}$ is optionally substituted arylalkyl;

R$_Y$ and R$_Z$ are independently hydrogen or an oxygen protecting group;

R$^7$ is selected from the group consisting of —Si(R$^B$)$_3$, optionally substituted arylalkyl, and —C(O)R$^C$, wherein R$^C$ is optionally substituted alkyl, optionally substituted aryl, or optionally substituted arylalkyl; and R$^4$ and R$^8$ are independently optionally substituted arylalkyl;

or a salt thereof.

2. The compound of claim 1, wherein the compound is of Formula (I-a) or (I-b):

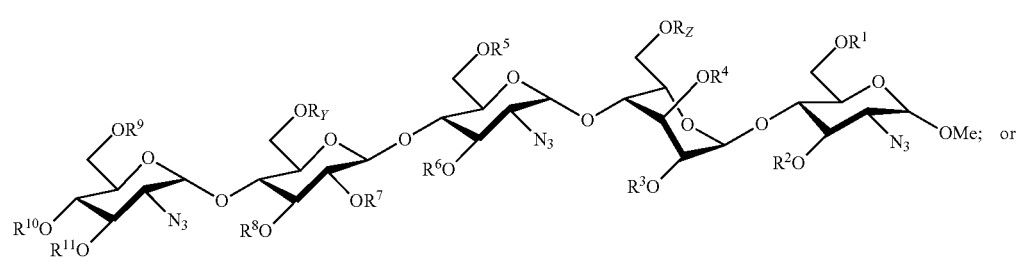

(I-a)

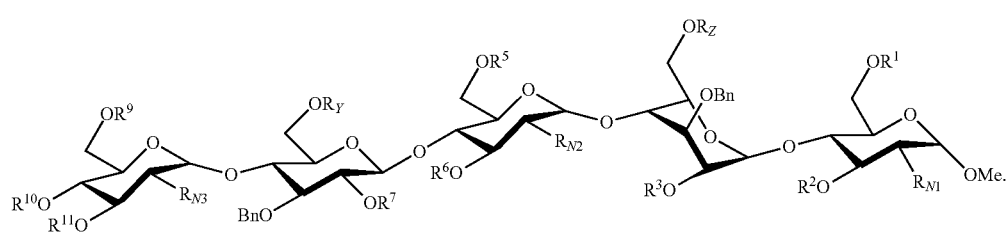

(I-b)

3. The compound of claim 1, wherein the compound is of the formula:

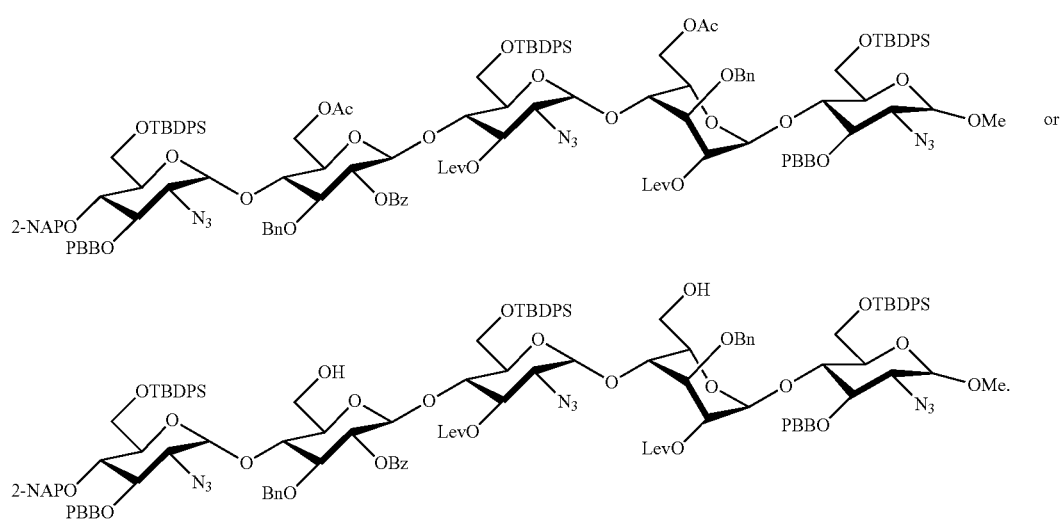

4. The compound of claim 1, wherein $X_1$ is in the alpha configuration or the beta configuration.

5. The compound of claim 1, wherein $X_1$ is $C_{1-10}$ alkoxy.

6. The compound of claim 1, wherein $R_{N1}$, $R_{N2}$, and $R_{N3}$ are independently selected from the group consisting of —$N_3$, —NH(Cbz), —NH(Boc), —NH(Fmoc), —NHC(O)CCl$_3$, —NHC(O)CH$_3$, and —N(C(O)CH$_3$)$_2$.

7. The compound of claim 1, wherein $R^1$, $R^5$, and $R^9$ are each —Si($R^B$)$_3$.

8. The compound of claim 7, wherein $R^1$, $R^5$ and $R^9$ are t-butyldiphenylsilyl.

9. The compound of claim 1, wherein $R^2$ and $R^{11}$ are each substituted benzyl.

10. The compound of claim 1, wherein $R^1$, $R^5$ and $R^9$ are t-butyldiphenylsilyl; and $R^2$ and $R^{11}$ are p-bromobenzyl.

11. The compound of claim 1, wherein $R^3$ and $R^6$ are levulinyl.

12. The compound of claim 1, wherein $R^1$, $R^5$ and $R^9$ are t-butyldiphenylsilyl; and $R^3$ and $R^6$ are levulinyl.

13. The compound of claim 1, wherein $R^7$ is —Si($R^B$)$_3$ or —C(O)$R^C$; wherein $R^C$ is optionally substituted alkyl or optionally substituted aryl.

14. The compound of claim 1, wherein $R^1$, $R^5$ and $R^9$ are t-butyldiphenylsilyl; and $R^7$ is benzoyl.

15. The compound of claim 1, wherein $R_Y$ and $R_Z$ are each hydrogen or each an oxygen protecting group.

16. The compound of claim 1, wherein $R^1$, $R^5$ and $R^9$ are t-butyldiphenylsilyl; and $R_Y$ and $R_Z$ are acetyl.

17. The compound of claim 1, wherein $X_1$ is selected from the group consisting of alpha-thiomethyl, beta-thiomethyl, alpha-thiocresyl, beta-thiocresyl, alpha-t-butyldiphenylsilyloxy, beta-t-butyldiphenylsilyloxy, and alpha-methoxy.

18. A compound of Formula (II):

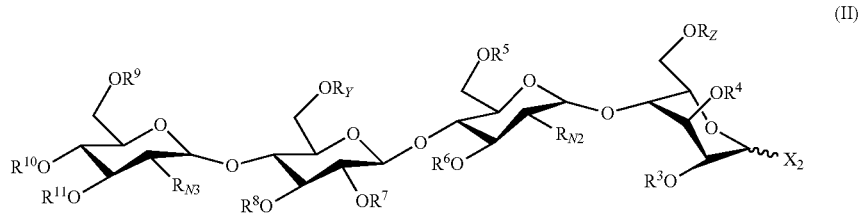

(II)

wherein:

- $X_2$ is —$OR^A$ or —$SR^A$, wherein $R^A$ is hydrogen, an oxygen or sulfur protecting group, optionally substituted $C_{1-10}$ alkyl, optionally substituted aryl, optionally substituted acyl, or optionally substituted imidoyl;
- $R^{11}$ is optionally substituted arylalkyl;
- $R_{N2}$ and $R_{N3}$ are independently —$N_3$ or —$N(R^W)_2$, wherein each $R^W$ is independently hydrogen or a nitrogen protecting group;
- $R^3$ and $R^6$ are independently —$C(O)R^D$, wherein each occurrence of $R^D$ is independently optionally substituted alkyl or optionally substituted aryl;
- $R^5$ and $R^9$ are independently selected from the group consisting of optionally substituted arylalkyl and —$Si(R^B)_3$, wherein each $R^B$ is independently alkyl or aryl;
- $R^{10}$ is optionally substituted arylalkyl;
- $R_Y$ and $R_Z$ are independently hydrogen or an oxygen protecting group;
- $R^7$ is selected from the group consisting of —$Si(R^B)_3$, optionally substituted arylalkyl, and —$C(O)R^C$, wherein $R^C$ is optionally substituted alkyl, optionally substituted aryl, or optionally substituted arylalkyl; and
- $R^4$ and $R^8$ are independently optionally substituted arylalkyl;

or a salt thereof.

19. The compound of claim 18, wherein $X_2$ is selected from the group consisting of halogen, optionally substituted thioalkyl, optionally substituted thioaryl, —$OC(=N)CCl_3$, —$OP(O)(OR^F)_2$, and n-pentenyl, wherein $R^F$ is hydrogen, optionally substituted alkyl, or optionally substituted acyl.

20. The compound of claim 18, wherein $X_2$ is —S-tolyl, —OH, or —OAc.

21. The compound of claim 18, wherein $R_{N2}$ and $R_{N3}$ are independently selected from the group consisting of —$N_3$, —NH(Cbz), —NH(Boc), —NH(Fmoc), —$NHC(O)CCl_3$, —$NHC(O)CH_3$, and —$N(C(O)CH_3)_2$.

22. The compound of claim 18, wherein $R^5$ and $R^9$ are each —$Si(R^B)_3$.

23. The compound of claim 18, wherein $R^{11}$ is optionally substituted benzyl.

24. The compound of claim 18, wherein $R^5$ and $R^9$ are t-butyldiphenylsilyl; and $R^{11}$ is p-bromobenzyl.

25. The compound of claim 18, wherein $R^3$ and $R^6$ are levulinyl.

26. The compound of claim 18, wherein $R^5$ and $R^9$ are t-butyldiphenylsilyl; and $R^3$ and $R^6$ are levulinyl.

27. The compound of claim 18, wherein $R^7$ is —$Si(R^B)_3$.

28. The compound of claim 18, wherein $R^7$ is —$C(O)R^D$, wherein $R^C$ is optionally substituted alkyl or optionally substituted aryl.

29. The compound of claim 18, wherein $R^5$ and $R^9$ are t-butyldiphenylsilyl; and $R^7$ is benzoyl.

30. The compound of claim 18, wherein $R_Y$ and $R_Z$ are each hydrogen or each an oxygen protecting group.

31. The compound of claim 18, wherein $R^5$ and $R^9$ are t-butyldiphenylsilyl; and $R_Y$ and $R_Z$ are acetyl.

32. The compound of claim 18, wherein the compound is of Formula (II-a) or Formula (II-b):

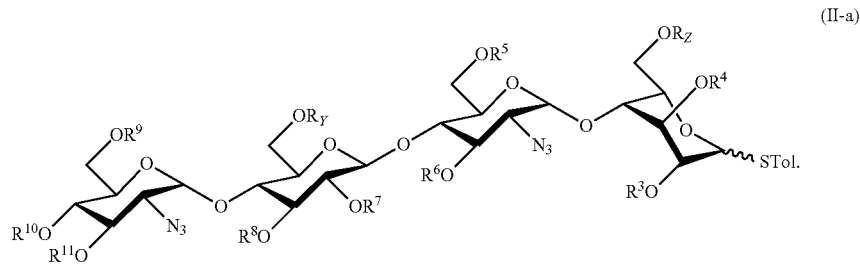

(II-a)

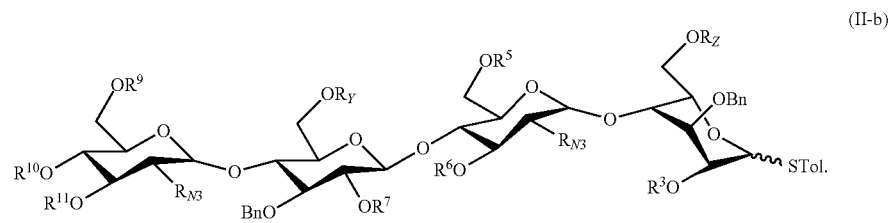

(II-b)

33. The compound of claim 18, wherein the compound is of the formula:

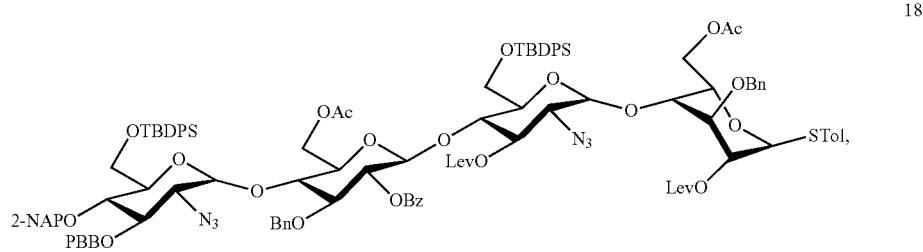

-continued

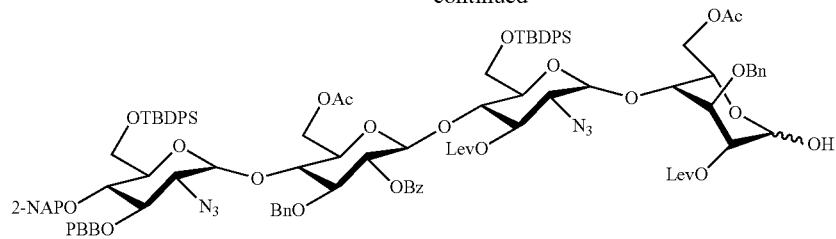

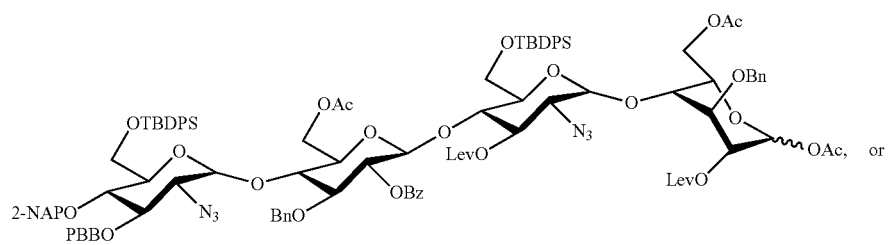

17

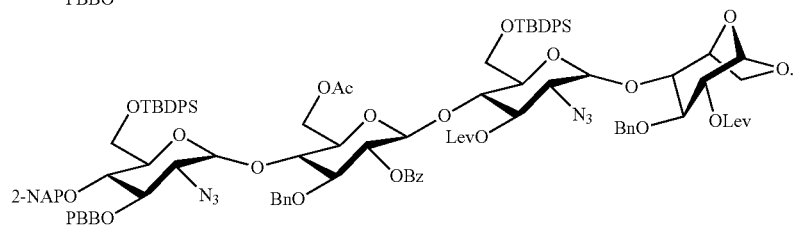

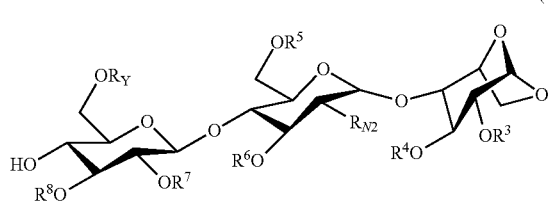

34. A compound of Formula (III):

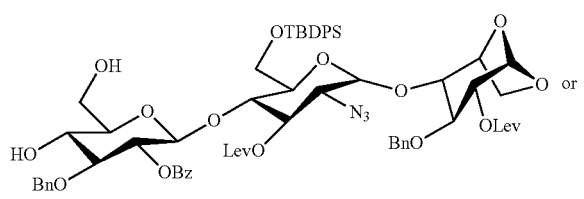

(III)

wherein:

R$_{N2}$ is —N$_3$ or —N(R$^W$)$_2$, wherein each R$^W$ is independently hydrogen or a nitrogen protecting group;

R$^3$ and R$^6$ are independently —C(O)R$^D$, wherein each occurrence of R$^D$ is independently optionally substituted alkyl or optionally substituted aryl;

R$^5$ is selected from the group consisting of optionally substituted arylalkyl and —Si(R$^B$)$_3$, wherein each R$^B$ is independently alkyl or aryl;

R$_Y$ is hydrogen or an oxygen protecting group;

R$^7$ is selected from the group consisting of —Si(R$^B$)$_3$, optionally substituted arylalkyl, and —C(O)R$^C$, wherein R$^C$ is optionally substituted alkyl, optionally substituted aryl, or optionally substituted arylalkyl; and R$^4$ and R$^8$ are independently optionally substituted arylalkyl;

or a salt thereof.

35. The compound of claim 34, wherein R$_{N2}$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$.

36. The compound of claim 34, wherein R$^5$ is a silyl protecting group.

37. The compound of claim 34, wherein R$^5$ is t-butyldiphenylsilyl; and R$^3$ and R$^6$ are levulinyl.

38. The compound of claim 34, wherein R$^7$ is —Si(R$^B$)$_3$ or —C(O)R$^C$, wherein R$^C$ is optionally substituted alkyl or optionally substituted aryl.

39. The compound of claim 34, wherein R$^5$ is t-butyldiphenylsilyl; and R$^7$ is benzoyl.

40. The compound of claim 34, wherein R$_Y$ is hydrogen or an oxygen protecting group.

41. The compound of claim 34, wherein R$^5$ is t-butyldiphenylsilyl; and R$_Y$ is acetyl.

42. The compound of claim 34, wherein the compound is of the formula:

15

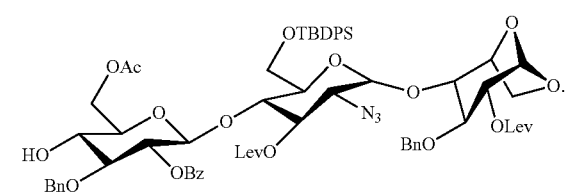

16

43. A method for for synthesizing fondaparinux 25:

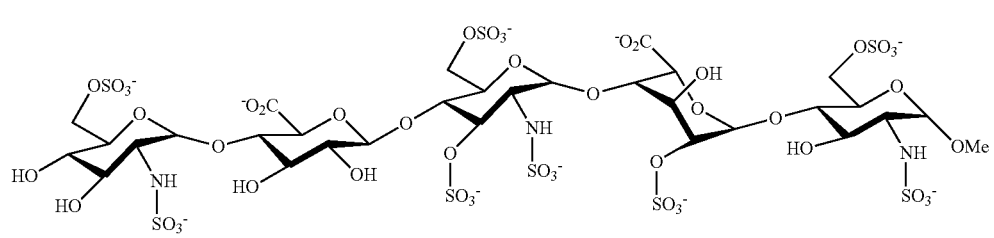

or a salt thereof;

the method comprising:
(a) deprotecting a pentasaccharide of formula (I) or a salt thereof:

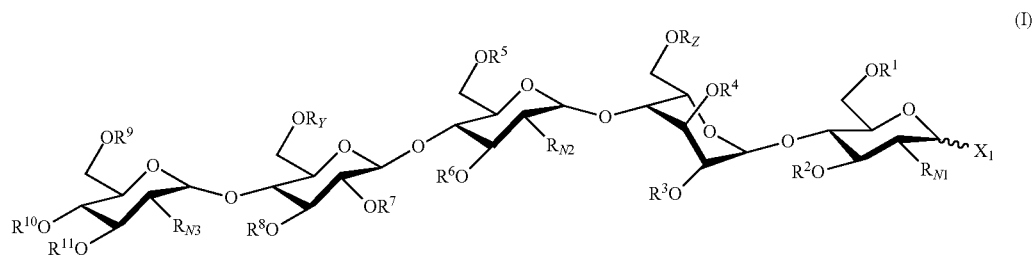

wherein:
$X_1$ is alpha-methoxy;
$R^2$ and $R^{11}$ are independently optionally substituted arylalkyl;
$R_{N1}$, $R_{N2}$, and $R_{N3}$ are independently —$N_3$ or —$N(R^W)_2$, wherein each $R^W$ is independently hydrogen or a nitrogen protecting group;
$R^3$ and $R^6$ are independently —$C(O)R^D$, wherein each occurrence of $R^D$ is independently optionally substituted alkyl or optionally substituted aryl;
$R^1$, $R^5$, and $R^9$ are independently selected from the group consisting of optionally substituted arylalkyl and —$Si(R^B)_3$, wherein each $R^B$ is independently alkyl or aryl;

$R^{10}$ is optionally substituted arylalkyl;
$R_Y$ and $R_Z$ are independently hydrogen or an oxygen protecting group;
$R^7$ is selected from the group consisting of —$Si(R^B)_3$, optionally substituted arylalkyl, and —$C(O)R^C$, wherein $R^C$ is optionally substituted alkyl, optionally substituted aryl, or optionally substituted arylalkyl; and
$R^4$ and $R^8$ are independently optionally substituted arylalkyl;

under suitable conditions to form a compound of formula (IX):

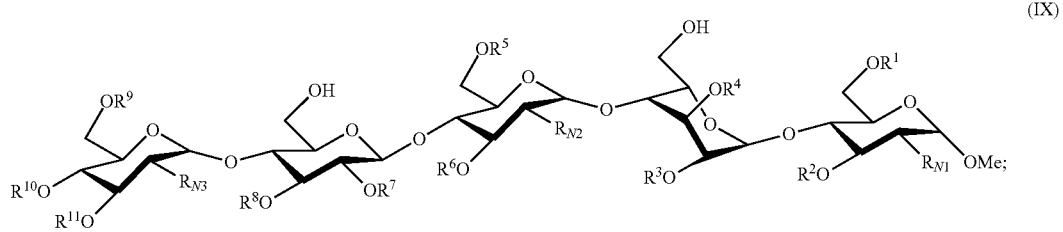

wherein $R^1$, $R^2$, $R^3$, $R^4$, $R^5$, $R^6$, $R^7$, $R^8$, $R^9$, $R^{10}$, $R^{11}$, $R_{N1}$, $R_{N2}$, and $R_{N3}$ are as defined above;

(b) oxidizing, deprotecting, and esterifying the compound of formula (IX) under suitable conditions to form a compound of formula (X):

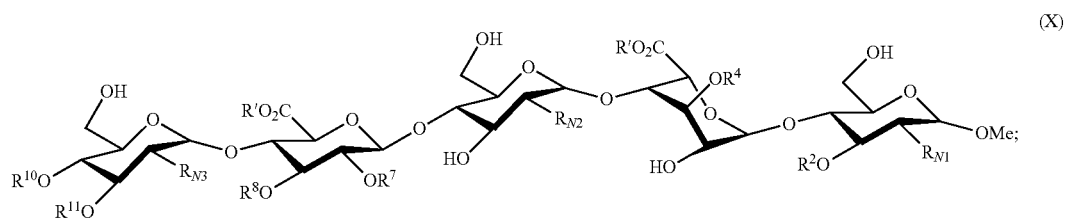
(X)

wherein R' is $C_{1-6}$ alkyl or optionally substituted benzyl; and wherein $R^2$, $R^4$, $R^7$, $R^8$, $R^{10}$, $R^{11}$, $R_{N1}$, $R_{N2}$, and $R_{N3}$ are as defined above;

(c) sulfonating the compound of formula (X) under suitable conditions to form a compound of formula (XI):

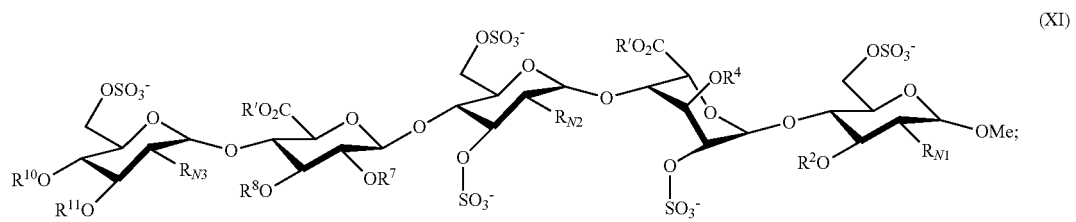
(XI)

wherein $R^2$, $R^4$, $R^7$, $R^8$, $R^{10}$, $R^{11}$, $R_{N1}$, $R_{N2}$, and $R_{N3}$ are as defined above;

(d) converting the compound of formula (XI) to a compound of formula (XII) under suitable conditions:

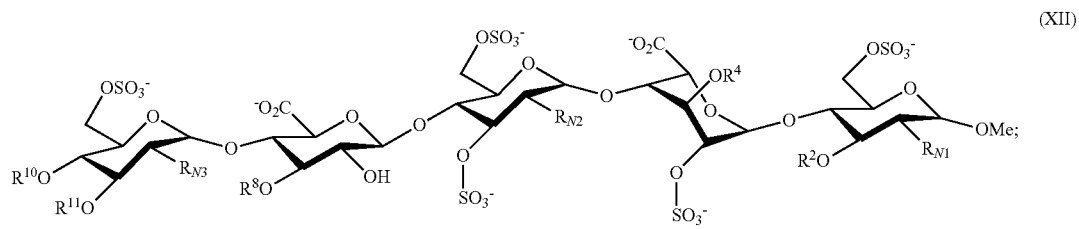
(XII)

(e) deprotecting the compound of formula (XII) under suitable conditions to form a compound of formula (XIII):

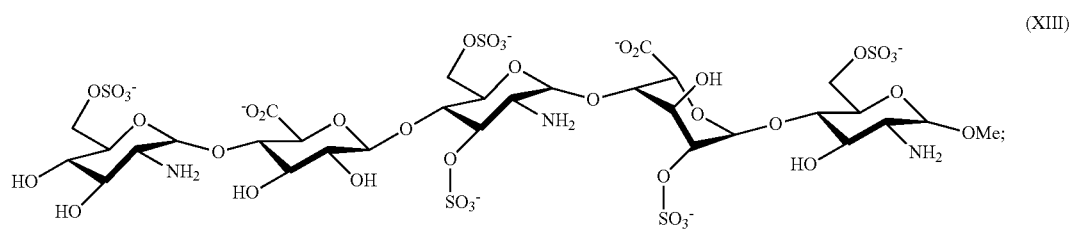
(XIII)

and (f) sulfonating the compound of formula (XIII) under suitable conditions to form fondaparinux 25 or a salt thereof.

44. The method of claim 43, further comprising a second process for synthesizing the pentasaccharide of formula (I), the second process comprising: reacting a tetrasaccharide of formula (II):

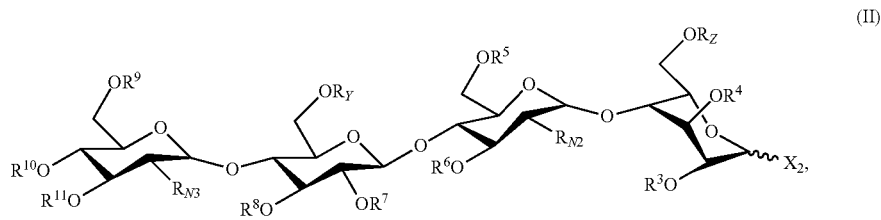
(II)

wherein $X_2$ is —$OR^A$ or —$SR^A$, in which $R^A$ is hydrogen, an oxygen or sulfur protecting group, optionally substituted $C_{1-10}$ alkyl, optionally substituted aryl, optionally substituted acyl, or optionally substituted imidoyl; and $R^3$, $R^4$, $R^5$, $R^6$, $R^7$, $R^8$, $R^9$, $R^{10}$, $R^{11}$, $R_Y$, $R_Z$, $R_{N2}$, and $R_{N3}$ are as defined in claim 43;

with monosaccharide E:

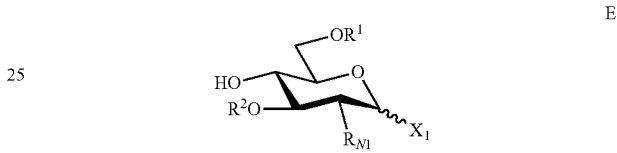
E under suitable conditions to form a pentasaccharide of formula (I), wherein $X_1$, $R^1$, $R^2$, and $R_{N1}$ are as defined in claim 43.

45. The method of claim 44, further comprising a third process for synthesizing the tetrasaccharide of formula (II): the process comprising:

(a) reacting a trisaccharide of formula (III):

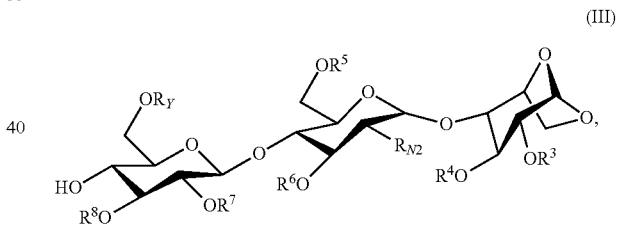
(III)

wherein $R^{N2}$, $R^3$, $R^4$, $R^5$, $R^6$, $R^8$, and $R^Y$ are as defined in claim 44;

with a monosaccharide of formula A:

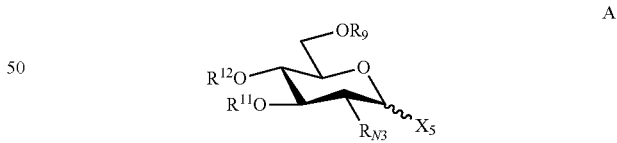
A wherein $X_5$ is a leaving group and $R_{N3}$, $R^9$, $R^{11}$, and $R^{12}$ are as defined in claim 44;

in the presence of an activating agent under suitable conditions to form a compound of formula (VIIIa):

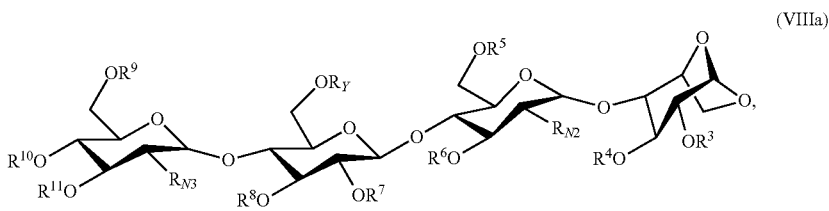
(VIIIa)

wherein $R^3$, $R^4$, $R^5$, $R^6$, $R^7$, $R^8$, $R^9$, $R^{10}$, $R^{11}$, $R_Y$, $R_{N2}$, and $R_{N3}$ are as defined in claim 44;

(b) ring-opening and protecting the compound of formula (VIIIa) under suitable conditions to form a compound of formula (VIII):

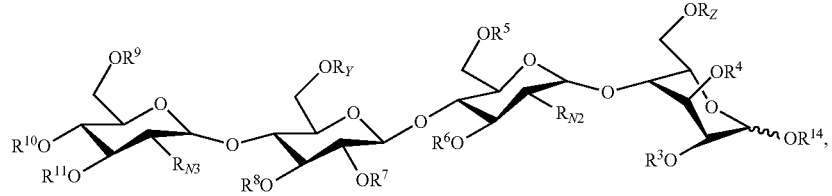

wherein $R^{14}$ is an oxygen protecting group and $R^3$, $R^4$, $R^5$, $R^6$, $R^7$, $R^8$, $R^9$, $R^{10}$, $R^{11}$, $R^{14}$, $R_Y$, $R_Z$, $R_{N2}$, and $R_{N3}$ are as defined in claim 44; and (c) converting the —$OR^{14}$ group of the compound of formula (VIII) to the group $X_2$ under suitable conditions to form the compound of formula (II).

46. A method of synthesizing fondaparinux

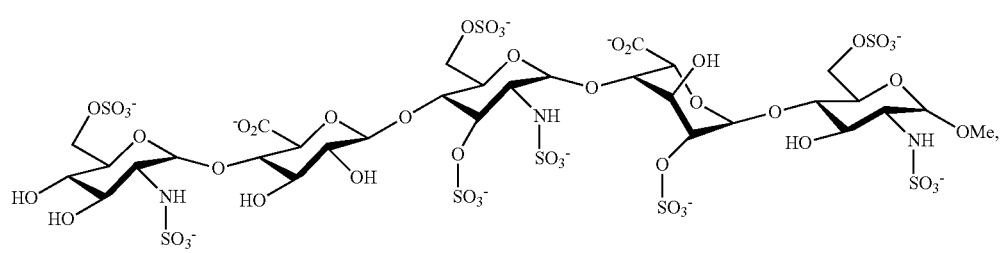

or a salt thereof,
the method comprising:
(1) a first process for synthesizing a trisaccharide of formula (III):

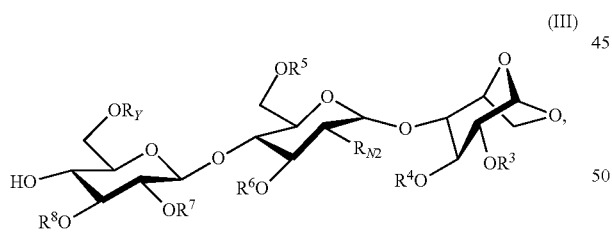

in which
  $R_{N2}$ is —$N_3$ or —$N(R^W)_2$, wherein each $R^W$ is independently hydrogen or a nitrogen protecting group;
  $R^3$ and $R^6$ are independently —$C(O)R^D$, wherein each occurrence of $R^D$ is independently optionally substituted alkyl or optionally substituted aryl;
  $R^5$ is selected from the group consisting of optionally substituted arylalkyl and —$Si(R^B)_3$, wherein each $R^B$ is independently alkyl or aryl;
  $R_Y$ is hydrogen or an oxygen protecting group;
  $R^7$ is selected from the group consisting of —$Si(R^B)_3$, optionally substituted arylalkyl, and —$C(O)R^C$, wherein $R^C$ is optionally substituted alkyl, optionally substituted aryl, or optionally substituted arylalkyl; and $R^4$ and $R^8$ are independently optionally substituted arylalkyl;
or a salt thereof;
the first process comprising:
(a) reacting monosaccharides of formulae C and D;

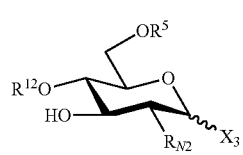

-continued

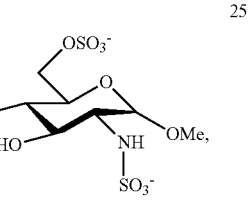

wherein $R^{12}$ and $R^{13}$ are each independently an oxygen protecting group;
$X_3$ is a leaving group; and
$R^4$, $R^5$, and $R_{N2}$ are as defined above;
  in the presence of an activating agent under suitable conditions to form a disaccharide of formula (IV):

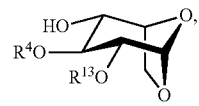

wherein $R^{N2}$, $R^4$, $R^5$, $R^{12}$, and $R^{13}$ are as defined above;
(b) deprotecting the disaccharide of formula (IV) under suitable conditions to form a compound of formula (V):

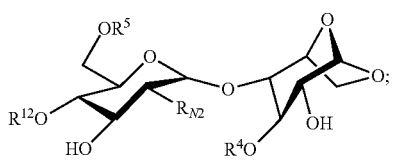

(V)

wherein $R^{N2}$, $R^4$, $R^5$, and $R^{12}$ are as defined above;

(c) protecting and deprotecting the compound of formula (V) under suitable conditions to form a compound of formula (VI):

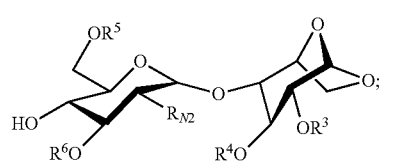

(VI)

wherein $R^{N2}$, $R^3$, $R^4$, $R^5$, and $R^6$ are as defined above;

(d) reacting the compound of formula (VI) with a monosaccharide of formula B:

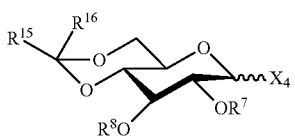

B wherein $R^{15}$ and $R^{16}$ are independently hydrogen, alkyl or aryl, wherein at least one of $R^{15}$ and $R^{16}$ is not hydrogen;
$X_4$ is a leaving group; and
$R^7$ and $R^8$ are as defined above;
in the presence of an activating agent under suitable conditions to form a trisaccharide of formula (VII):

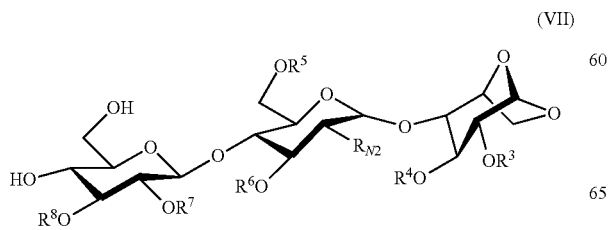

(VII)

wherein $R^{N2}$, $R^3$, $R^4$, $R^5$, $R^6$, $R^7$, and $R^8$ are as defined above;

(e) protecting the trisaccharide of formula (VII) under suitable conditions to form the trisaccharide of formula (III);

(2) a second process for synthesizing a tetrasaccharide of formula (II):

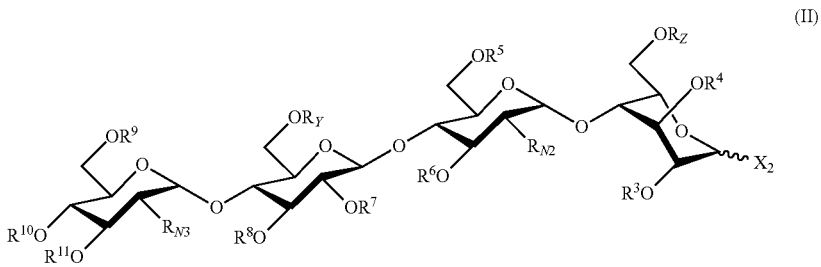

(II)

or a salt thereof;

wherein:

$X_2$ is —$OR^A$ or —$SR^A$, wherein $R^A$ is hydrogen, an oxygen or sulfur protecting group, optionally substituted $C_{1-10}$ alkyl, optionally substituted aryl, optionally substituted acyl, or optionally substituted imidoyl;

$R^{11}$ is optionally substituted arylalkyl;

$R_{N3}$ is —$N_3$ or —$N(R^W)_2$, wherein each $R^W$ is independently hydrogen or a nitrogen protecting group;

$R^9$ is selected from the group consisting of optionally substituted arylalkyl and —$Si(R^B)_3$, wherein each $R^B$ is independently alkyl or aryl;

$R^{10}$ is optionally substituted arylalkyl;

$R_Z$ is hydrogen or an oxygen protecting group; and $R_{N2}$, $R^3$, $R^4$, $R^5$, $R^6$, $R^7$, $R^8$, and $R_Y$ are as defined above;

the second process comprising:

(a) reacting the trisaccharide of formula (III):
with a monosaccharide of formula A:

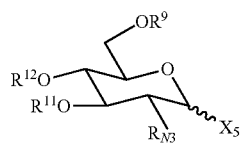

A wherein $X_5$ is a leaving group; and $R^{N3}$, $R^9$, $R^{11}$, and $R^{12}$ are as defined above;

in the presence of an activating agent under suitable conditions to form a compound of formula (VIIIa):

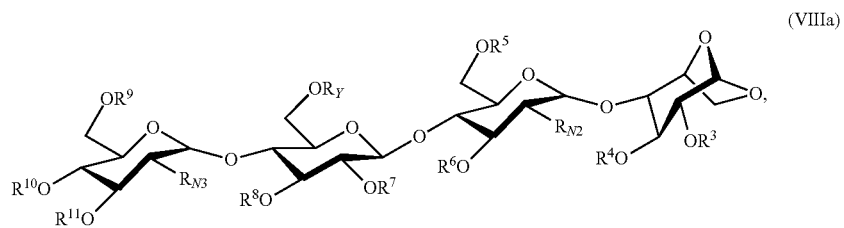

wherein $R^3$, $R^4$, $R^5$, $R^6$, $R^7$, $R^8$, $R^9$, $R^{10}$, $R^{11}$, $R_Y$, $R_{N2}$, and $R_{N3}$ are as defined above;
(b) ring-opening and protecting the compound of formula (VIIIa) under suitable conditions to form a compound of formula (VIII):

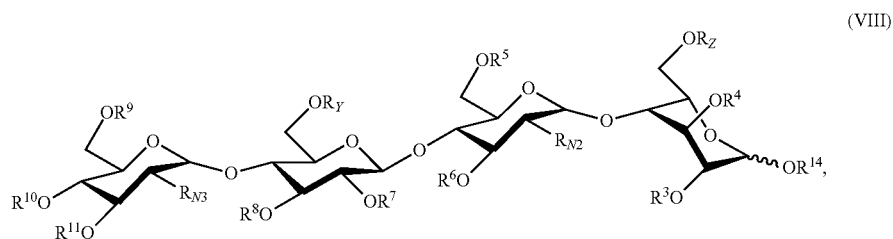

wherein $R^{14}$ is an oxygen protecting group; and $R^3$, $R^4$, $R^5$, $R^6$, $R^7$, $R^8$, $R^9$, $R^{10}$, $R^{11}$, $R^{14}$, $R_Y$, $R_Z$, $R_{N2}$, and $R_{N3}$ are as defined above; and
(c) converting the —$OR^{14}$ group of the compound of formula (VIII) to the group $X_2$ under suitable conditions to form the tetrasaccharide of formula (II);
(3) a third process for synthesizing a pentasaccharide of formula (I):

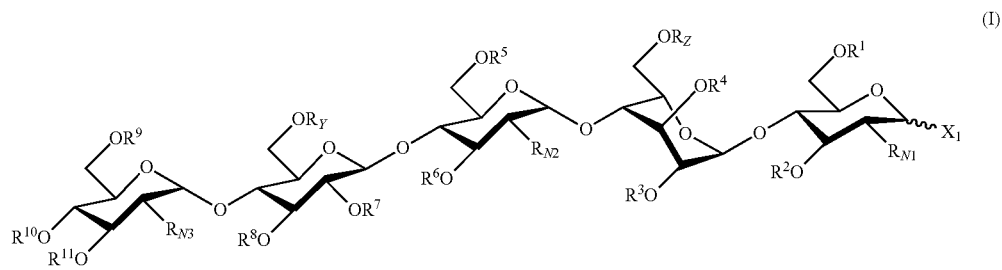

or a salt thereof;
wherein:
$X_1$ is alpha-methoxy;
$R^2$ is optionally substituted arylalkyl;
$R_{N1}$ is —$N_3$ or —$N(R^W)_2$, wherein each $R^W$ is independently hydrogen or a nitrogen protecting group;

$R^1$ is selected from the group consisting of optionally substituted arylalkyl and —$Si(R^B)_3$, wherein each $R^B$ is independently alkyl or aryl; and
$R_{N2}$, $R_{N3}$, $R_3$, $R_4$, $R_5$, $R_6$, $R_7$, $R_8$, $R_9$, $R_Y$, and $R_Z$ are as defined above;
the third process comprising:
reacting the tetrasaccharide of formula (II):

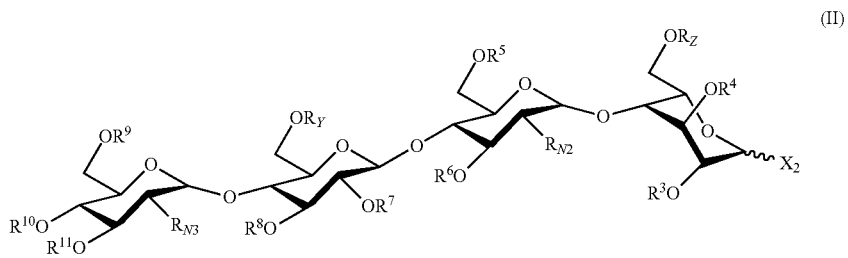

wherein $X_2, R^3, R^4, R^5, R^6, R^7, R^8, R^9, R^{10}, R^{11}, R_Y, R_Z, R_{N2}$, and $R_{N3}$ are as defined above;

with monosaccharide E:

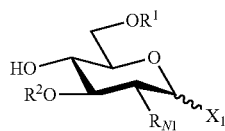

under suitable conditions to form the pentasaccharide of formula (I);

wherein $X_1, R^1, R^2$ and $R_{N1}$ are as defined above;

(4) a fourth process for synthesizing fondaparinux 25:

or a salt thereof;

the fourth process comprising:

(a) deprotecting the pentasaccharide of formula (I):

under suitable conditions to form a compound of formula (IX):

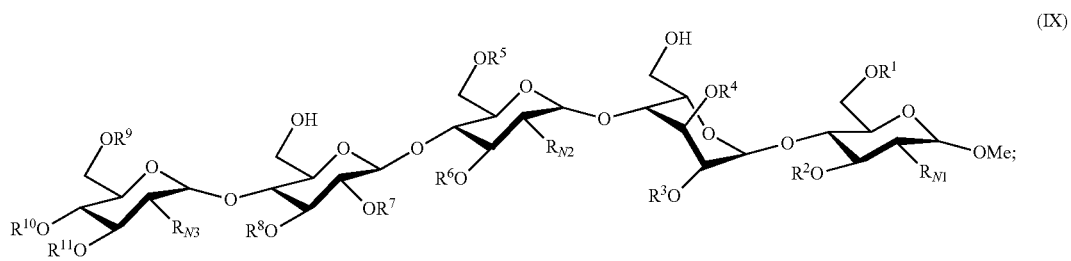

wherein $R^1, R^2, R^3, R^4, R^5, R^6, R^7, R^8, R^9, R^{10}, R^{11}, R_{N1}, R_{N2}$, and $R_{N3}$ are as defined above;

(b) oxidizing, deprotecting, and esterifying the compound of formula (IX) under suitable conditions to form a compound of formula (X):

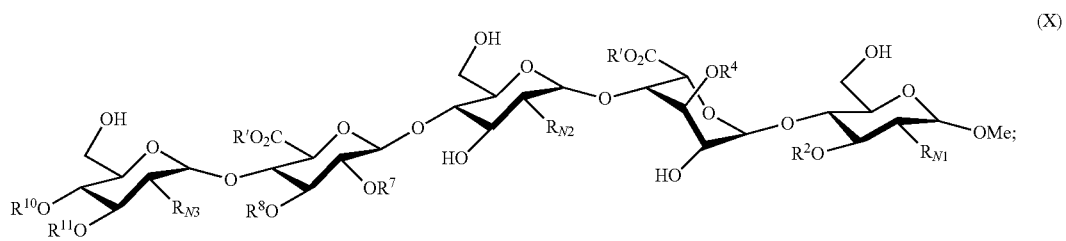

wherein R' is $C_{1-6}$ alkyl or optionally substituted benzyl; and wherein $R^2, R^4, R^7, R^8, R^{10}, R^{11}, R_{N1}, R_{N2}$, and $R_{N3}$ are as defined above;

(c) sulfonating the compound of formula (X) under suitable conditions to form a compound of formula (XI):

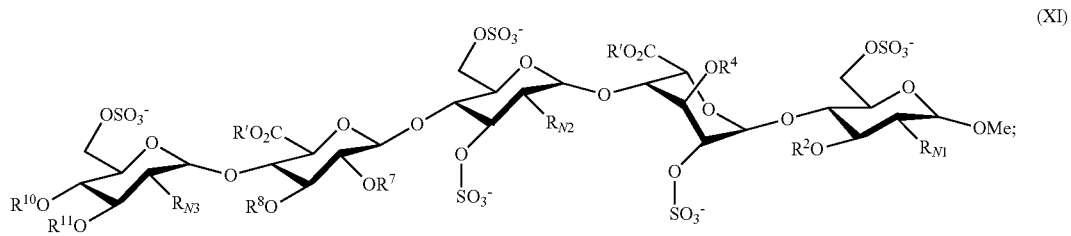

wherein $R^2, R^4, R^7, R^8, R^{10}, R^{11}, R_{N1}, R_{N2}$, and $R_{N3}$ are as defined above;

(d) converting the compound of formula (XI) to a compound of formula (XII) under suitable conditions:

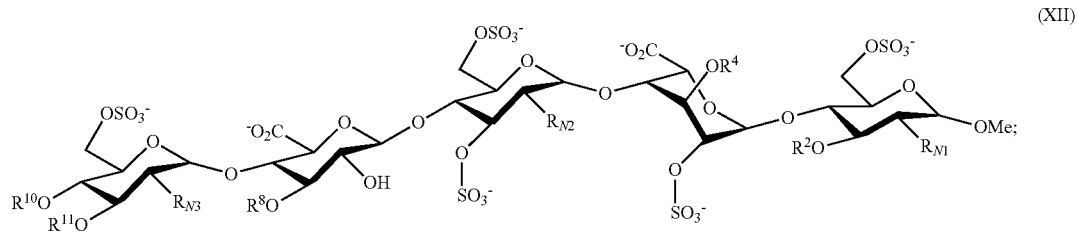
(XII)

wherein $R^2$, $R^4$, $R^8$, $R^{10}$, $R^{11}$, $R_{N1}$, $R_{N2}$, and $R_{N3}$ are as defined above;

(e) deprotecting the compound of formula (XII) under suitable conditions to form a compound of formula (XIII):

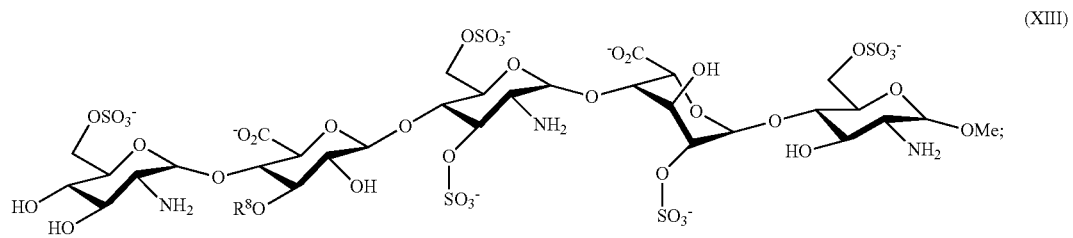
(XIII)

24 and (f) sulfonating the compound of formula (XIII) under suitable conditions to form fondaparinux 25, or a salt thereof.

47. The method of claim 46, wherein the trisaccharide of formula (III) is compound 16:

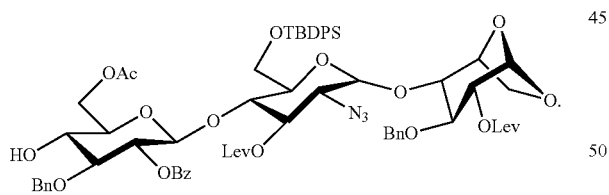
16

48. The method of claim 46, wherein the disaccharide of formula (IV) is compound 12:

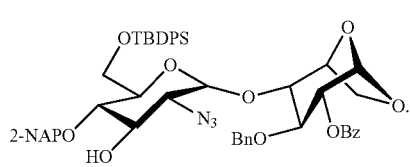
12

49. The method of claim 46, wherein the compound of formula (V) is compound 13:

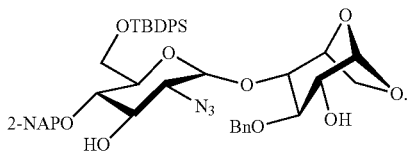
13

50. The method of claim 46, wherein the compound of formula (VI) is compound 14:

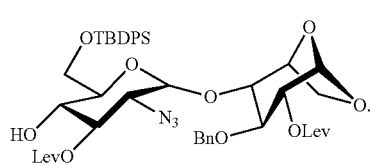
14

51. The method of claim 46, wherein the trisaccharide of formula (VII) is compound 15:

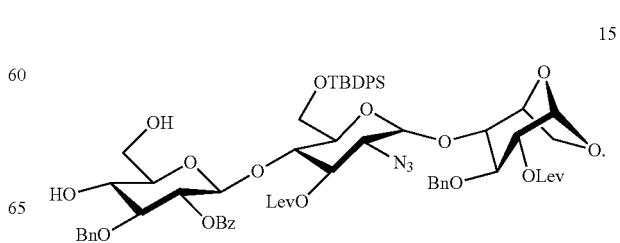
15

52. The method of claim 46, wherein the deprotection step (b) comprises treating the disaccharide of (IV) with base.

53. The method of claim 46, wherein $R_Y$ is acetyl.

54. The method of claim 46, wherein $R^3$ is levulinyl.

55. The method of claim 46, wherein step (c) comprises protecting the compound of formula (V) with EDC, DMAP, and 4-oxopentanoic acid.

56. The method of claim 46, wherein $R^{12}$ is 2-napththylmethyl.

57. The method of claim 56, wherein step (c) comprises deprotecting the compound of formula (V) with 2,3-dichloro-5,6-dicyano-1,4-benzoquinone (DDQ).

58. The method of claim 46, wherein $R^4$ and $R^8$ are benzyl.

59. The method of claim 46, wherein $R_{N2}$ is $-N_3$.

60. A method of synthesizing a tetrasaccharide of formula (II):

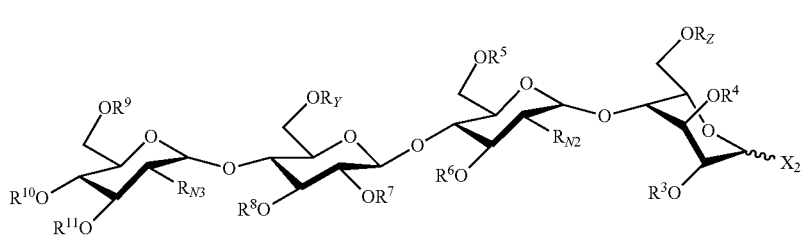

(II)

or a salt thereof;
wherein:
- $X_2$ is $-OR^A$ or $-SR^A$, wherein $R^A$ is hydrogen, an oxygen or sulfur protecting group, optionally substituted $C_{1-10}$ alkyl, optionally substituted aryl, optionally substituted acyl, or optionally substituted imidoyl;
- $R^{11}$ is optionally substituted arylalkyl;
- $R_{N2}$ and $R_{N3}$ are independently $-N_3$ or $-N(R^W)_2$, wherein each $R^W$ is independently hydrogen or a nitrogen protecting group;
- $R^3$ and $R^6$ are independently $-C(O)R^D$, wherein each occurrence of $R^D$ is independently optionally substituted alkyl or optionally substituted aryl;
- $R^5$ and $R^9$ are independently selected from the group consisting of optionally substituted arylalkyl and $-Si(R^B)_3$, wherein each $R^B$ is independently alkyl or aryl;
- $R^{10}$ is optionally substituted arylalkyl;
- $R_Y$ and $R_Z$ are independently hydrogen or an oxygen protecting group;
- $R^7$ is selected from the group consisting of $-Si(R^B)_3$, optionally substituted arylalkyl, and $-C(O)R^C$, wherein $R^C$ is optionally substituted alkyl, optionally substituted aryl, or optionally substituted arylalkyl; and $R^4$ and $R^8$ are independently optionally substituted arylalkyl;

the method comprising:
(a) reacting a trisaccharide of formula (III):

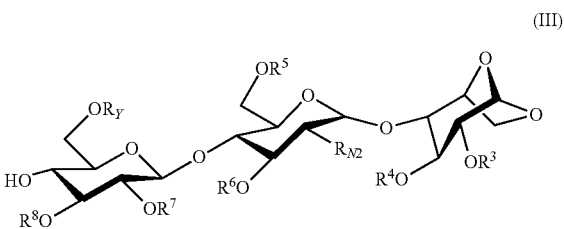

(III)

wherein $R^{N2}$, $R^3$, $R^4$, $R^5$, $R^6$, $R^8$, and $R^Y$ are as defined above;

with a monosaccharide of formula A:

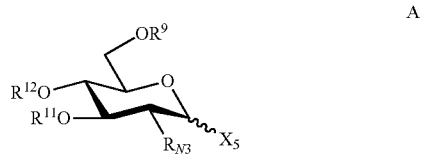

A wherein $X_5$ is a leaving group; and wherein $R_{N3}$, $R^9$, $R^{11}$, and $R^{12}$ are as defined above;

in the presence of an activating agent under suitable conditions to form a compound of formula (VIIIa):

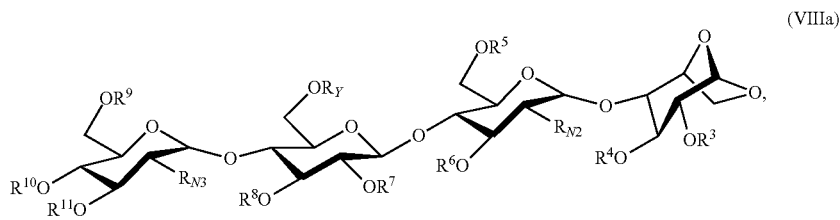

(VIIIa)

wherein $R^3$, $R^4$, $R^5$, $R^6$, $R^7$, $R^8$, $R^9$, $R^{10}$, $R^{11}$, $R_Y$, $R_{N2}$, and $R_{N3}$ are as defined above;

(b) ring-opening and protecting the compound of formula (VIIIa) under suitable conditions to form a compound of formula (VIII):

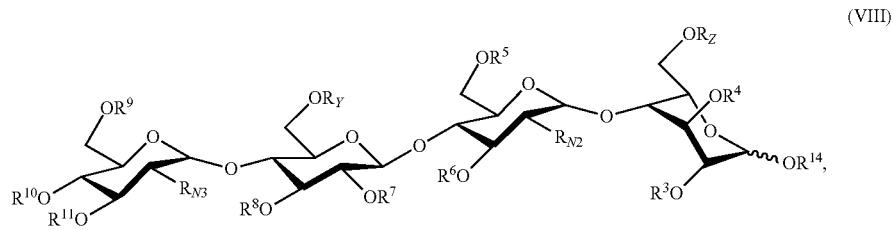

(VIII)

wherein $R^{14}$ is an oxygen protecting group; and wherein $R^3$, $R^4$, $R^5$, $R^6$, $R^7$, $R^8$, $R^9$, $R^{10}$, $R^{11}$, $R^{14}$, $R_Y$, $R_Z$, $R_{N2}$, and $R_{N3}$ are as defined above; and (c) converting the —$OR^{14}$ group of the compound of formula (VIII) to the group $X_2$ under suitable conditions to form the tetrasaccharide of formula (II), or a salt thereof.

61. The method of claim 60, wherein the tetrasaccharide of formula (II) is compound 18:

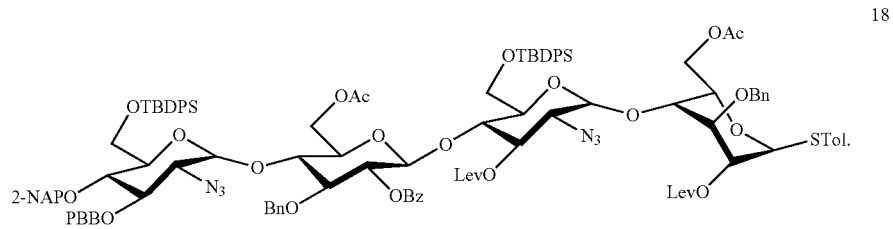

18

62. The method of claim 60, wherein the trisaccharide of formula (III) is compound 16:

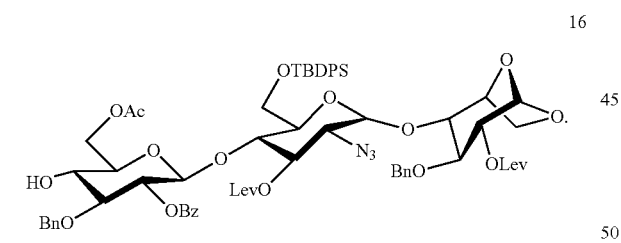

16

63. The method of claim 60, wherein the trisaccharide of formula (III) is prepared by a process comprising:

(a) reacting monosaccharides of formulae C and D;

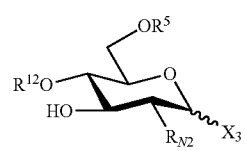

C

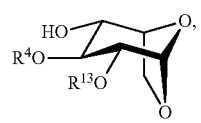

D wherein $R^{12}$ and $R^{13}$ are each independently an oxygen protecting group; $X_3$ is a leaving group; and $R^4$, $R^5$, and $R_{N2}$ are as defined above in claim 60;

in the presence of an activating agent under suitable conditions to form a disaccharide of formula (IV):

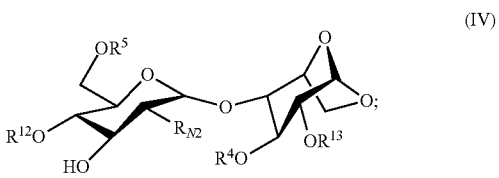

(IV)

wherein $R^{N2}$, $R^4$, $R^5$, $R^{12}$, and $R^{13}$ are as defined above in claim 60;

(b) deprotecting the disaccharide of formula (IV) under suitable conditions to form a compound of formula (V):

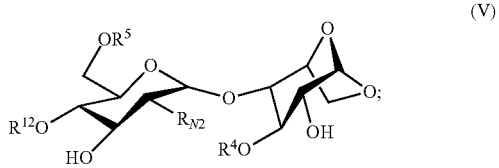

(V)

wherein $R^{N2}$, $R^4$, $R^5$, and $R^{12}$ are as defined above in claim 60;

(c) protecting and deprotecting the compound of formula (V) under suitable conditions to form a compound of formula (VI):

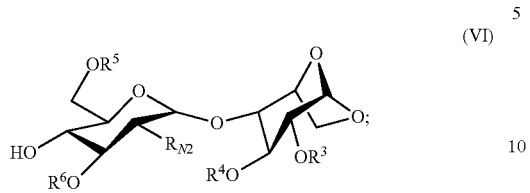
(VI)

wherein $R^{N2}$, $R^3$, $R^4$, $R^5$, and $R^6$ are as defined above in claim 60;

(d) reacting the compound of formula (VI) with a monosaccharide of formula B:

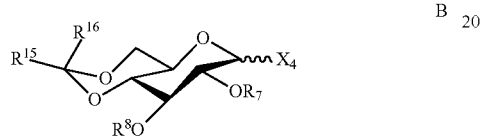
B wherein $R^{15}$ and $R^{16}$ are independently hydrogen, alkyl or aryl, wherein at least one of $R^{15}$ and $R^{16}$ is not hydrogen; $X_4$ is a leaving group; and $R^7$ and $R^8$ are as defined above in claim 60;

in the presence of an activating agent under suitable conditions to form a trisaccharide of formula (VII):

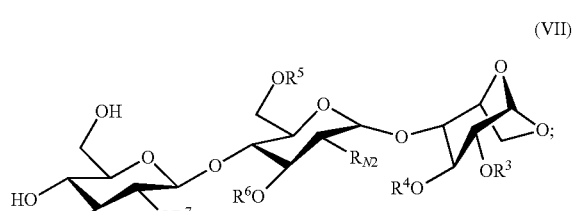
(VII)

wherein $R^{N2}$, $R^3$, $R^4$, $R^5$, $R^6$, $R^7$, and $R^8$ are as defined above in claim 60;

(e) protecting the trisaccharide of formula (VII) under suitable conditions to form the trisaccharide of formula (III).

64. The method of claim 60, wherein the compound of formula (VIII) is compound 17:

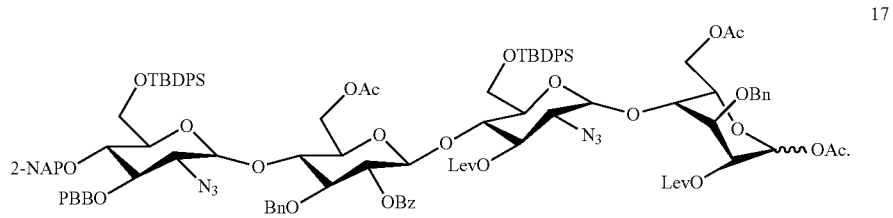
17

65. The method of claim 60, wherein $R^{14}$, $R_Y$, and $R_Z$ are acetyl.

* * * * *

UNITED STATES PATENT AND TRADEMARK OFFICE
CERTIFICATE OF CORRECTION

PATENT NO. : 9,822,140 B2
APPLICATION NO. : 14/406074
DATED : November 21, 2017
INVENTOR(S) : Shang-Cheng Hung et al.

It is certified that error appears in the above-identified patent and that said Letters Patent is hereby corrected as shown below:

In the Claims

In Claim 28, at Column 80, Line 19, the phrase: "$R^7$ is $-C(O)R^D$" should be replaced with: --$R^7$ is $-C(O)R^C$--.

In Claim 43, at Column 83, Lines 1-2, wherein the phrase: "A method for for synthesizing fondaparinux 25" should be replaced with: --A method for synthesizing fondaparinux 25--.

Signed and Sealed this
Twenty-fourth Day of April, 2018

Andrei Iancu
*Director of the United States Patent and Trademark Office*